US006919424B2

(12) United States Patent
Rondon et al.

(10) Patent No.: US 6,919,424 B2
(45) Date of Patent: Jul. 19, 2005

(54) BINDING PEPTIDES FOR CARCINOEMBRYONIC ANTIGEN (CEA)

(75) Inventors: Isaac Jesus Rondon, Boston, MA (US); Robert Charles Ladner, Ijamsville, MD (US)

(73) Assignee: Dyax Corp., Cambridge, MA (US)

( * ) Notice: Subject to any disclaimer, the term of this patent is extended or adjusted under 35 U.S.C. 154(b) by 0 days.

(21) Appl. No.: 09/825,517

(22) Filed: Apr. 3, 2001

(65) Prior Publication Data

US 2003/0203415 A1 Oct. 30, 2003

Related U.S. Application Data

(63) Continuation-in-part of application No. 09/541,345, filed on Apr. 3, 2000, now Pat. No. 6,774,209.

(51) Int. Cl.[7] .......................... C07K 5/00; C07K 14/00; C07K 16/00; C07K 7/00

(52) U.S. Cl. ...................... 530/300; 530/326; 530/350; 530/387.1

(58) Field of Search ................................ 530/300, 326, 530/350, 387.1, 327, 328

(56) References Cited

U.S. PATENT DOCUMENTS

| 5,047,507 A | 9/1991 | Buchegger et al. |
|---|---|---|
| 5,223,409 A | 6/1993 | Ladner et al. |
| 5,872,215 A | 2/1999 | Osbourne et al. |
| 5,912,334 A | 6/1999 | Kato et al. |
| 5,977,315 A | 11/1999 | Chatterjee et al. |

FOREIGN PATENT DOCUMENTS

| EP | 1074617 A2 | 2/2001 |
|---|---|---|
| JP | 9131191 | 5/1997 |
| JP | 2000191697 | 7/2000 |
| WO | WO 92/21364 | 12/1992 |
| WO | WO 95/06067 | 3/1995 |
| WO | WO 96/41172 | 12/1996 |
| WO | WO 99/26961 | 6/1999 |
| WO | WO 99/54436 | 10/1999 |
| WO | WO 00/44908 | 8/2000 |
| WO | WO 01/18250 A2 | 3/2001 |
| WO | WO 01/25427 A1 | 4/2001 |
| WO | WO 01/36632 A2 | 5/2001 |
| WO | WO 01/51512 A2 | 7/2001 |
| WO | WO 01/57270 A2 | 8/2001 |
| WO | WO 01/57274 A2 | 8/2001 |
| WO | WO 01/57275 A2 | 8/2001 |
| WO | WO 01/75068 A2 | 10/2001 |

OTHER PUBLICATIONS

Inal, J.M., et al., "Schistosoma TOR (Trispanning Orphan Receptor), a Novel, Antigenic Surface Receptor of the Blood–Dwelling, Schistosoma Parasite," Biochim. Biophys. Acta. 1445:283–298 (1999).

Lawler, J. and Hynes, R.O., "The Structure of Human Thrombospondin, an Adhesive Glycoprotein with Multiple Calcium–Binding Sites and Homologies with Several Different Proteins," J. Cell Biol. 103:1635–1648 (1986).

Imbach, T., et al., A Mutatuion in the Human Ortholog of the Saccharomyces cerevisiae ALG 6 Gene Causes Carbohydrate–Deficient Glycoprotein Syndrome Type–Ic, Proc. Natl. Acad. Sci. USA 96:6982–6987 (1999).

Chatterjee, S.K., et al., "Molecular Mimicry of Carcinoembryonic Antigen by Peptides Derived from the Structure of an Anti–Idiotype Antibody," Cancer Res. 58:1217–1224 (1998).

Hammarström, S., "The Carcinoembryonic Antigen (CEA) Family: Structures, Suggested Functions and Expression in Normal and Malignant Tissues," Sem. Cancer Biol., (9):67–81 (1999).

Beauchemin et al., Mol. Cell. Biol., 7:3221–3230 (1987).

Berche et al., Br. Med. J., 285: 1447–1451 (1982).

Gold and Freedman, J. Exp. Med., 121: 439–462 (1965).

Hengerer et al., Biotechniques, 26(5): 956–964 (1999).

Mach et al., Immun. Today, 2: 239–349 (1981).

Merrifield, J. Am. Chem. Soc., 85:2149–2154 (1963).

Aljinovic, G., and Pohl, T.M., "Sequence and Analysis of 24 kb on Chromosome II of Saccharomyces cerevisiae," Yeast, 11(5):475–479 (1995).

Amerik, A.Y., et al., "In vivo Disassembly of Free Polyubiquitin Chains by Yeast Ubp14 Modulates Rates of Protein Degradation by the Proteasome," EMBO J., 16(16):4826–4838 (1997).

Brown, D.D., et al., "The Thyroid Hormone–induced Tail Resorption Program During Xenopus laevis Metamorphosis," Proc. Natl. Acad. Sci. U.S.A., 93(5):1924–1929 (1996).

Cheret, G., et al., "DNA Sequence Analysis of the VPHI–SNF2 Region on Chromosome XV of Saccharomyces cerevisiae," Yeast, 12:1059–1064 (1996).

Duharcourt, S., et al., "Homology–Dependent Maternal Inhibition of Developmental Excision of Internal Eliminated Sequences in Paramecium tetraurelia," Mol. Cell Biol., 18(12):7075–7085 (1998).

Hennessy, S.W., et al., "Complete Thrombospondin mRNA Sequence Includes Potential Regulatory in the 3' Untranslated Region," J. Cell Biol., 108(2):729–736 (1989).

(Continued)

Primary Examiner—Karen A. Canella
(74) Attorney, Agent, or Firm—Fish & Richardson P.C.

(57) ABSTRACT

The present invention provides binding moieties for CEA, which have a variety of uses wherever detecting, isolating or localizing CEA, and particularly CEA as opposed to cross-reactive antigens such as NCA, is advantageous. Particularly disclosed are synthetic, isolated polypeptides capable of binding CEA, which is overexpressed in adenocarcinomas of endodermally derived digestive system epithelia and fetal colon. Such polypeptides and disclosed derivatives are useful, e.g., as imaging agents for CEA-expressing tumors.

13 Claims, 8 Drawing Sheets

OTHER PUBLICATIONS

Hiromoto, K., et al., "Molecular Cloning of Equine Interlukin-1 α and -β cNDAs," *Vet. Immunol. Immunopathol.*, 48:221–231 (1995).

Huang, D., et al., "Structural Organization and Splice Variants of the *POLE1* Gene Encoding the Catalytic Subunit of Human DNA Polymerase ε," *Biochem. J.*, 339(3):657–665 (1999).

Huang, D., et al., "cDNA and Structural Organization of the gene *Pole1* for the mouse DNA Polymearse ε Catalytic Subunit," *Biochim. Biophys. Acta*, 1445(3):363–371 (1999).

Kato, H., et al., "Identification of an Alternatively Spliced Transcript of Equine Interleukin-1 β," *Gene*, 177:11–16 (1996).

Kawano, T., et al., "Structures of Insulin–like Peptides of the Nematode *Caenorhabditis elegans*," *Peptide Science*, 35:117–120 (1998).

Kawano, T., et al., "Molecular Cloning and Characterization of a New Insulin/IGF–like Peptide of the Nematode *Caenorhabditis elegans*," *Biochem. Biophys. Res. Commun.*, 273(2):431–436 (2000).

Kesti, T., et al., "Molecular Cloning of the cDNA for the Catalytic Subunit of Human DNA Polymerase ε," *J. Biol. Chem.*, 268(14):10238–10245 (1993).

Li, Y., et al., "Purification, cDNA Cloning, and Gene Mapping of the Small Subunit of Human DNA Polymerase ε," *J. Biol. Chem.*, 272(51):32337–32344 (1997).

Nielsen, E., et al., "Cysteine Residue Periodicity is a Conserved Structural Feature of Variable Surface Proteins from *Paramecium tetraurelia*," *J. Mol. Biol.*, 222(4):835–841 (1991).

Okinaka, R.T., et al., "Sequence and Organization of pX01, the Large *Bacillus anthracis* Plasmid Harboring the Anthrax Toxin Genes," *J. Bacteriol.*, 181(20):6509–6515 (1999).

Prat, A., "Conserved Sequences Flank Variable Tandem Repeats in two Alleles of the G Surface Protein of *Paramecium primaurelia*," *J. Mol. Biol.*, 211(3):521–535 (1990).

Prat, A., et al., "Nucleotide Sequence of the *Paramecium primaurelia* G Surface Protein," *J. Mol. Biol.*, 189(1):47–60 (1986).

Tachikawa, H., et al., "Isolation and Characterization of a Yeast Gene, *MPD1*, the Overexpress of Which Suppresses Inviability Caused by Protein Disulfide Isomerase Depletion," *FEBS Lett.*, 369:212–216 (1995).

Thébault, S., et al., "Molecular Cloning of a Novel Human I–mfa Domain–containing Protein That Differently Regulates Human T–cell Leukemia Virus Type I and HIV–1 Expression," *J. Biol. Chem.*, 275(7):4848–4857 (2000).

Ueno, A., et al., "cDNA Cloning of Bovine Thrombospondin 1 and its Expression in Odontoblasts and Predentin," *Biochim. Biophys. Acta*, 1382(1):17–22 (1998).

Wang, H., et al., "Genetic Diversity of Hantaviruses Isolated in China and Characterization of Novel Hantaviruses Isolated from *Niviventer confucianus* and *Rattus rattus*," *Virology*, 278(2):332–345 (2000).

BINDING PEPTIDES FOR CARCINOEMBRYONIC ANTIGEN (CEA)

CROSS-REFERENCE TO RELATED APPLICATION

This application is a continuation-in-part of and claims priority to U.S. application Ser. No. 09/541,345, filed 3 Apr. 2000 now U.S. Pat. No. 6,774,209.

FEDERAL FUNDING

The present invention was partly supported by STTR grant no. 1R41CA79230-01. As a result, the U.S. government may retain certain rights in the invention.

FIELD OF THE INVENTION

The present invention relates to CEA binding polypeptides and compositions for detection and treatment of cancer. More particularly, the invention relates to materials useful for and methods of detecting, imaging, localizing, and targeting tumors exhibiting CEA. The invention provides binding polypeptides capable of associating specifically with CEA and of distinguishing between CEA and known cross-reactive antigens, such as NCA (non-specific cross-reacting antigen). Such binding polypeptides are useful for the detection, imaging, localization, and targeting of CEA-containing tissues or solutions, e.g., by radioimaging, magnetic resonance imaging, or x-ray imaging, and are also useful in the diagnosis and treatment of cancers associated with CEA.

BACKGROUND OF THE INVENTION

Carcinoembryonic antigen, or CEA, is a complex immunoreactive glycoprotein with a molecular weight of 180,000 found in adenocarcinomas of endodermally derived digestive system epithelia and fetal colon. Tumor cells at many sites, including colon, breast, lung, cervix, ovary, stomach, bladder, pancreas and esophagus express large amounts of carcinoembryonic antigen and/or the closely related immunoglobulin supergene family member, nonspecific cross-reactive antigen, or NCA, on their surfaces. The expression of these glycoproteins, especially CEA, in normal cells is very limited in mature individuals (as opposed to prenatal infants), and this antigen has been used as a target in immunoassays for diagnosis and for serially monitoring cancer patients for recurrent disease or response to therapy. (See, Mach et al., *Immun. Today,* 2: 239, 1981; Berche et al., *Br. Med. J.,* 285: 1447, 1982.) Anti-CEA antibodies also have been proposed for cancer therapy and for use in forming immunoconjugates, which in turn can be used in cancer therapy. (See, e.g., Buchegger et al., U.S. Pat. No. 5,047,507 (1991); Osbourne et al. U.S. Pat. No. 5,872,215 (1999).)

CEA was as first described by Gold and Freedman, *J. Exp. Med.,* 121: 439, 1965, and has now been completely sequenced and characterized (see, Beauchemin et al., *Mol. Cell. Biol.,* 7:3221–30, 1987; WO 95/06067). CEA has a domain structure of N-A1-B1-A2-B2-A3-B3-GPI where GPI is a glycophosphatidylinositol membrane anchor. A significant degree of sequence homology exists between the domains of CEA and other members of the immunoglobulin supergene family, and immunological cross-reactivity between CEA and as many as sixteen other homologous antigens, such as NCA and biliary glycoprotein-1 (BGP-1), has been reported.

One of the major drawbacks of the use of anti-CEA antibodies for clinical purposes has been the cross-reactivity of these antibodies with some apparently normal adult tissues. Previous studies have shown that most conventional hyperimmune antisera raised against different immunogenic forms of CEA cross-react with CEA-related antigens found in normal colonic mucosa, spleen, liver, lung, sweat glands, polymorphonuclear leukocytes and monocytes of normal individuals, as well as many different types of carcinomas.

Accordingly, there is a great need for binding moieties that bind to CEA but do not cross-react with other antigens such as NCA. This and other objects are accomplished herein with the discovery of novel peptide binders of CEA.

SUMMARY OF THE INVENTION

The present invention addresses the need for improved materials and methods for detecting, localizing, measuring and treating CEA-expressing cells by providing a group of non-naturally occurring polypeptides that bind specifically to CEA. Appropriate labeling of such polypeptides provides detectable imaging agents that bind at high concentration to a CEA-expressing tumor, providing excellent tumor-specific imaging agents. Conjugation or fusion of such polypeptides with effective agents such as cytokines, chemotherapeutic agents, radionuclides or other cancer therapeutics produce conjugates that can be used for cancer therapy, i.e., by causing the conjugate to target the site of a tumor that is producing CEA. Recombinant bacteriophage displaying the CEA-binding polypeptides of the invention have been identified and isolated, and such phage products are also valuable reagents for effective detection and diagnosis of cancers associated with the expression of CEA in cells and tissues. The CEA binding moieties of the instant invention can be used in the detection, diagnosis, and therapy of such CEA-related disorders.

This invention pertains to CEA binding moieties. Binding moieties according to this invention are useful in any application where binding, detecting or isolating CEA or its fragments is advantageous. A particularly advantageous use of the binding moieties disclosed herein is in a method of imaging cells or tissues expressing CEA in vivo. The method entails the use of CEA specific binding moieties according to the invention for detecting CEA-expressing cells, where the binding moieties have been detectably labeled for use as imaging agents, including magnetic resonance imaging (MRI) contrast agents, x-ray imaging agents, radiopharmaceutical imaging agents, ultrasound imaging agents, and optical imaging agents.

Preferred CEA binding moieties according to the invention are isolated, synthetic polypeptides having a high affinity for CEA. This invention provides a new class of CEA binding polypeptides having an amino acid sequence comprising:

Cys-$X_4$-$X_5$-$X_6$-$X_7$-$X_8$-$X_9$-$X_{10}$-$X_{11}$-Cys,  (SEQ ID NO:110)
wherein $X_4$ is Asn, Glu, Asp, or Met;

$X_5$ is Leu, Phe, Tyr, Trp, Val, Met, Ile, or Asn;

$X_6$ is Phe, Leu, Asp, Glu, Ala, Ile, Lys, Asn, Ser, Val, Trp, Tyr, Gly, or Thr;

$X_7$ is Lys, Phe, Asp, Gly, Leu, Asn, Trp, Ala, Gln, or Thr;

-continued $X_8$ is Asn, Pro, Phe, Gly, Asp, Ala, Ser, Glu, Gln, Trp, His, Arg, Met, Val, or Leu;

$X_9$ is Gln, Lys, Leu, or Gly;

$X_{10}$ is Trp, Ala, or Tyr; and $X_{11}$ is Phe, Thr, Met, Ser, Ala, Asn, Val, His, Ile, Pro, Trp, Tyr, Gly, Leu, or Glu.

Preferred CEA binding polypeptides of the above formula include polypeptides having the amino acid sequence:

$X_1$-$X_2$-$X_3$-Cys-$X_4$-$X_5$-$X_6$-$X_7$-$X_8$-$X_9$-$X_{10}$-$X_{11}$-Cys-$X_{12}$-$X_{13}$-$X_{14}$, wherein  (SEQ ID NO:111)

$X_1$ is Asp, Asn, Ala, or Ile;

$X_2$ is Trp;

$X_3$ is Val, Ile, Met, Tyr, Phe, Pro, or Asp;

$X_4$ is Asn, Glu, Asp, or Met;

$X_5$ is Leu, Phe, Tyr, Trp, Val, Met, Ile, or Asn;

$X_6$ is Phe, Leu, Asp, Glu, Ala, Ile, Lys, Asn, Ser, Val, Trp, Tyr, Gly, or Thr;

$X_7$ is Lys, Phe, Asp, Gly, Leu, Asn, Trp, Ala, Gln, or Thr;

$X_8$ is Asn, Pro, Phe, Gly, Asp, Ala, Ser, Glu, Gln, Trp, His, Arg, Met, Val, or Leu;

$X_9$ is Gln, Lys, Leu, or Gly;

$X_{10}$ is Trp, Ala, or Tyr;

$X_{11}$ is Phe, Thr, Met, Ser, Ala, Asn, Val, His, Ile, Pro, Trp, Tyr, Gly, Leu, or Glu;

$X_{12}$ is Asn, Asp, Glu, Pro, Gln, Ser, Phe, or Val;

$X_{13}$ is Val, Leu, Ile, Pro, Ala, Gln, Ser, Met, Glu, Thr, Lys, Trp, or Arg; and $X_{14}$ is Leu, Met, Val, Tyr, Ala, Ile, Trp, His, Pro, Gln, Glu, Phe, Lys, Arg, or Ser.

Other preferred CEA binding polypeptides of the above formula will have the amino acid sequence:

$X_1$-$X_2$-$X_3$-Cys-$X_4$-$X_5$-$X_6$-$X_7$-$X_8$-$X_9$-$X_{10}$-  (SEQ ID NO:1)

$X_{11}$-Cys-$X_{12}$-$X_{13}$-$X_{14}$, wherein $X_1$ is Asn, Asp, or is absent;

$X_2$ is Trp;

$X_3$ is Asp, Phe, or Val;

$X_4$ is Asn, Glu, or Met;

$X_5$ is Asn, Leu, Met or Phe;

$X_6$ is Asp, Gly, Ile, Lys, Phe or Thr;

$X_7$ is Ala, Gln, Gly, Lys, or Thr;

$X_8$ is Arg, Asn, Asp, Glu, or Gly;

$X_9$ is Gln, Gly, or Leu;

$X_{10}$ is Ala, Trp or Tyr;

$X_{11}$ is Ala, Gly, His, Phe, Thr, or Val;

$X_{12}$ is Asn, Gln, Phe, Ser or Val;

$X_{13}$ is Arg, Leu, Pro or Ser; and $X_{14}$ is Leu, Ser, Trp or Tyr;

and wherein said polypeptide has the ability to bind CEA. Said polypeptide may have additional amino acids attached at either end. Peptides having a serine at the N-terminus (before $X_1$) are preferred embodiments.

Still other preferred CEA binding polypeptides of the above formula will have the amino acid sequence:

$X_1$-Trp-Val-Cys-Glu-$X_5$-$X_6$-Lys-$X_8$-Gln-  (SEQ ID NO:2)

Trp-$X_{11}$-Cys-Asn-$X_{13}$-$X_{14}$, wherein $X_1$ is Asn or Asp;

$X_5$ is Asn, Leu, Met or Phe;

$X_6$ is Asp, Gly, Ile, Lys, Phe or Thr;

$X_8$ is Arg, Asn, Asp, Glu, Gly or Trp;

$X_{11}$ is Ala, Gly, His, Phe, Thr, Tyr or Val;

$X_{13}$ is Arg, Leu, Pro or Ser; and $X_{14}$ is Leu, Ser, Trp or Tyr;

In particular, a stable binding domain having a high affinity for CEA is disclosed, having the formula:

Cys-$X_4$-$X_5$-$X_6$-$X_7$-$X_8$-$X_9$-$X_{10}$-$X_{11}$-Cys,  (SEQ ID NO:3)

wherein $X_4$ is Asn, Glu, or Met;

$X_5$ is Asn, Leu, Met or Phe;

$X_6$ is Asp, Gly, Ile, Lys, Phe or Thr;

$X_7$ is Ala, Gln, Gly, Lys, or Thr;

$X_8$ is Arg, Asn, Asp, Glu, or Gly;

$X_9$ is Gln, Gly, or Leu;

$X_{10}$ is Ala, Trp or Tyr;

$X_{11}$ is Ala, Gly, His, Phe, Thr, or Val;

and wherein it is preferred that $X_4$ is Glu;

$X_5$ is Asn, Leu, Met or Phe;

$X_6$ is Asp, Gly, Ile, Lys, Phe or Thr;

$X_7$ is Lys;

$X_8$ is Arg, Asn, Asp, Glu, or Gly;

-continued

X$_9$ is Gln;

X$_{10}$ is Trp; and

X$_{11}$ is Ala, Gly, His, Phe, Thr, or Val.

Preferred polypeptides according to the invention comprise an amino acid sequence:
Asn-Trp-Val-Cys-Asn-Leu-Phe-Lys-Asn-Gln-Trp-Phe-Cys-Asn-Ser-Tyr (SEQ ID NO:4)(also referred to herein as FX-G08 or simply G08, and as peptide DX207),
Asp-Trp-Val-Cys-Glu-Asn-Lys-Lys-Asp-Gln-Trp-Thr-Cys-Asn-Leu-Leu (SEQ ID NO:5)(also referred to herein as AB-A07 or simply A07, and as peptide DX208),
Asn-Trp-Asp-Cys-Met-Phe-Gly-Ala-Glu-Gly-Trp-Ala-Cys-Ser-Pro-Trp (SEQ ID NO:6)(also referred to herein as TN10/9-E01, and DX210),
Asp-Trp-Val-Cys-Glu-Lys-Thr-Thr-Gly-Gly-Tyr-Val-Cys-Gln-Pro-Leu (SEQ ID NO:7)(also referred to herein as TN10/9-B09),
Asn-Trp-Phe-Cys-Glu-Met-Ile-Gly-Arg-Gln-Trp-Gly-Cys-Val-Pro-Ser (SEQ ID NO:8)(also referred to herein as TN10/9-F11), and
Asp-Trp-Val-Cys-Asn-Phe-Asp-Gln-Gly-Leu-Ala-His-Cys-Phe-Pro-Ser (SEQ ID NO:9)(also referred to herein as TN10/9-D04).

The most preferred CEA binding moieties according to the invention are isolated, synthetic polypeptides having a high affinity for CEA. This invention provides a new class of CEA binding polypeptides having an amino acid sequence comprising:
X$_1$-X$_2$-X$_3$-Cys-X$_4$-X$_5$-X$_6$-X$_7$-X$_8$-X$_9$-X$_{10}$-X$_{11}$-Cys-X$_{12}$-X$_{13}$-X$_{14}$ (SEQ ID NO:1), wherein
X$_1$ is Asp, Asn, Ala, or Ile, with Asp most preferred;
X$_2$ is Trp;
X$_3$ is Val, Ile, Met, Tyr, Phe, Pro, or Asp, with Val most preferred;
X$_4$ is Asn, Glu, or Asp, with Asn and Glu most preferred;
X$_5$ is Leu, Phe, Tyr, Trp, Val, Met, Ile, or Asn, with Leu most preferred;
X$_6$ is Phe, Leu, Asp, Glu, Ala, Ile, Lys, Asn, Ser, Val, Trp, or Tyr, with Phe most preferred;
X$_7$ is Lys, Phe, Asp, Gly, Leu, Asn, or Trp, with Lys most preferred;
X$_8$ is Asn, Pro, Phe, Gly, Asp, Ala, Ser, Glu, Gln, or Trp, with Asn most preferred;
X$_9$ is Gln, or Lys, with Gln most preferred;
X$_{10}$ is Trp;
X$_{11}$ is Phe, Thr, Met, Ser, Ala, Asn, Val, His, Ile, Pro, Trp, or Tyr, with Phe most preferred;
X$_{12}$ is Asn, Asp, Glu, Pro, Gln, or Ser, with Asn and Asp most preferred;
X$_{13}$ is Val, Leu, Ile, Pro, Ala, Gln, Ser, Met, Glu, Thr, Lys, or Trp, with Val and Leu most preferred; and
X$_{14}$ is Leu, Met, Val, Tyr, Ala, Ile, Trp, His, Pro, Gln, Glu, Phe, Lys, or Arg, with Leu most preferred.

The polypeptides listed in Tables 5, 8, and 9 (infra) are preferred embodiments of the present invention. Polypeptides 304A-12-H12 (SEQ ID NO:59), 304A-14-B02 (SEQ ID NO:74), 304A-14-A12 (SEQ ID NO:83), and 304A-15-E04 (SEQ ID NO:92) are especially preferred embodiments of the present invention.

Another aspect of the present invention relates to modifications of the foregoing polypeptides to provide CEA specific imaging agents, wherein the binding moieties are modified by radiolabeling, enzymatic labeling, or labeling with MR paramagnetic chelates; or wherein the binding moieties are incorporated in microparticles, ultrasound bubbles, microspheres, emulsions, or liposomes; or wherein the binding moieties are conjugated with optical dyes.

In another aspect of the present invention, methods for isolating CEA binding moieties are provided. Such methods will be useful for isolating additional reagents for detection, localization, quantification, and treatment of neoplastic disorders associated with upregulated CEA expression.

In another aspect of the invention, methods of diagnosing CEA-associated disorders and methods for localizing CEA-expressing cells or tissues, are provided, and methods for treating cancers indicated by increased CEA expression are provided.

In another aspect of the invention, therapeutic agents comprising a combination, conjugation or fusion of an anticancer drug or other therapeutic agent with a CEA binding moiety according to the invention is provided. Such compositions will be useful in the treatment of CEA-associated disorders and conditions.

In another aspect of the invention, recombinant bacteriophage displaying CEA binding polypeptides on their surfaces are also provided. Such phage are useful as screening reagents and reagents for detecting CEA.

Another aspect of the invention relates to forming molecules containing multiple CEA-binding moieties to increase the residence time of these molecules on CEA targets. These multimeric molecules can be altered to provide CEA specific imaging agents by radiolabeling, enzymatic labeling, or labeling with MR paramagnetic chelates or microparticles; ultrasound bubbles, microparticles, microspheres, emulsions, or liposomes; or optical dyes.

Another aspect of the invention relates to introducing DNA that encodes one or more CEA-binding moieties into the coat protein of a virus to cause the virus to bind and preferentially infect CEA-bearing cells. Such alteration will make the virus target CEA-expressing (tumor) cells.

These and other aspects of the present invention will become apparent with reference to the following detailed description.

DEFINITIONS

Figure 1:
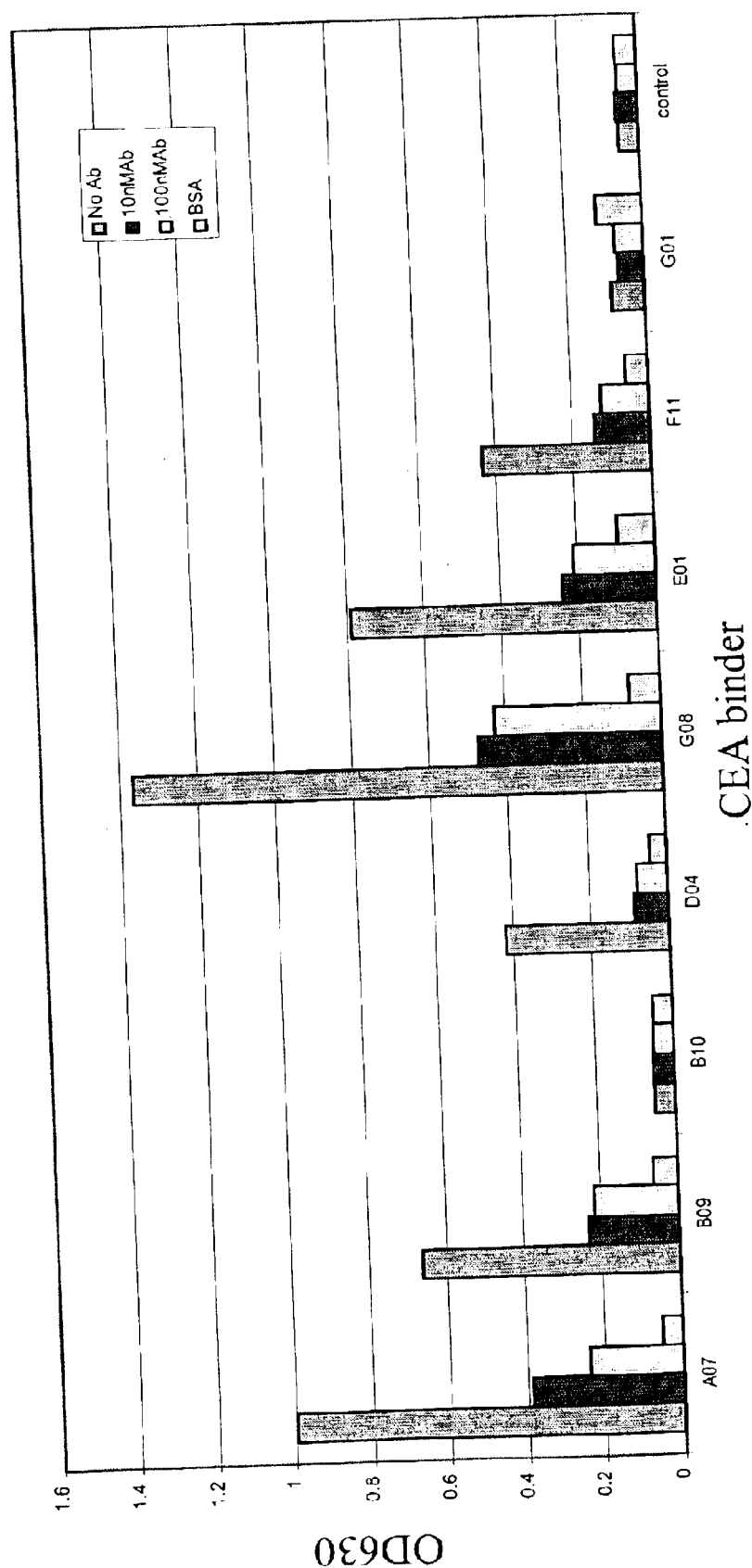
FIG. 1 shows results of a competition ELISA with CEA-binding phage initially isolated from the TN10/9 phage display library. The phage bearing CEA binding polypeptides are shown to compete for the same binding site (A3 domain) as the α-CEA(A3) chimeric antibody, cT84.66.

In the following sections, the term "recombinant" is used to describe non-naturally altered or manipulated nucleic acids, host cells transfected with exogenous (non-native) nucleic acids, or polypeptides expressed non-naturally, through manipulation of isolated DNA and transformation of host cells. Recombinant is a term that specifically encompasses DNA molecules which have been constructed in vitro using genetic engineering techniques, and use of the term "recombinant" as an adjective to describe a molecule, construct, vector, cell, polypeptide or polynucleotide specifically excludes naturally occurring such molecules, constructs, vectors, cells, polypeptides or polynucleotides.

The term "bacteriophage" is defined as a bacterial virus containing a DNA core and a protective shell built up by the aggregation of a number of different protein molecules. The terms "bacteriophage" and "phage" are used herein interchangeably.

The term "binding moiety" as used herein refers to any molecule, polypeptide, peptidomimetic or transformed cell ("transformant") capable of forming a binding complex with another molecule, polypeptide, peptidomimetic or cell. "CEA binding moiety" is a binding moiety that forms a complex with carcinoembryonic antigen (CEA) or a portion thereof, whether naturally expressed or synthetic or recombinant, soluble or membrane bound. Included among the portions of CEA specifically contemplated are the N-terminal domain (N), and intact domains A1, B1, A2, B2, A3, or B3, or combinations of two or more such domains in a single conjugate or fusion protein. Particular mention is made of the construct N-A3, which is a construct fusing the N-terminal domain of CEA with domain A3 of CEA. The A3 domain does not exhibit determinants having structural cognates in proteins known to be immunologically cross-reactive with CEA, and therefore binders to domain A3 may be capable of differentially binding to CEA and not those known structurally related antigens, such as, especially, NCA. Specific examples of CEA binding moieties are the polypeptides mentioned above (SEQ ID NOs:1–9, 24–27, and 36–151), hybrid polypeptides incorporating such polypeptides, and recombinant cells or bacteriophage displaying any of such polypeptides. Also included within the definition of CEA binding moieties are polypeptides derived from a polypeptide having an amino acid sequence according to SEQ ID NOs:110 and 111, above, which have been modified for particular results (in addition to CEA or like polypeptide binding ability). Specific examples of modifications contemplated are C- or N-terminal amino acid substitutions or elongations, e.g., for the purpose of linking the binding moiety to a detectable imaging label or other substrate. In addition to the detectable labels described further herein, other suitable substrates include anticancer drugs or other chemotherapeutic agents, enzymes, toxins, liposomes (e.g., loaded with a detectable label or chemotheraeutic agent), or a solid support, well, plate, bead, tube, slide, filter, or dish. Also specifically contemplated are substitutions of one or more cysteine residues that normally form disulfide links, for example substitution with non-naturally occurring amino acid residues having reactive side chains, for the purpose of forming a more stable bond between those amino acid positions than the former disulfide bond. All such modified CEA binding moieties are also considered CEA binding moieties so long as they retain the ability to bind CEA or a fragment or domain of CEA.

The term "binding" refers to the determination by standard techniques that a binding moiety recognizes and binds reversibly to a given target. Such standard techniques include equilibrium dialysis, gel filtration, and the monitoring of spectroscopic changes that result from binding, e.g., using flourescence anisotropy, either by direct binding measurements or competition assays with another binder.

The term "specificity" refers to a binding moiety having a higher binding affinity for one target over another. The term "CEA specificity" refers to a CEA binding moiety having a higher affinity for CEA as compared with another target, such as a serum protein (e.g., bovine serum albumin (BSA), human serum albumin (HSA)) or gelatin.

The term "polypeptide" refers to a linear polymer of two or more amino acid residues linked with amide bonds, and the term "peptide" is used herein to refer to relatively short polypeptides, e.g., having fewer than about 30 amino acids.

In the present application, a CEA binding moiety is said to "target" CEA-expressing cells if the binding moiety accumulates in or near the CEA-expressing cells or if the binding moiety is selectively taken up by the CEA-expressing cells or if the binding moiety is selectively taken up by and metabolized by the CEA-expressing cells. Substances that are not CEA binding moieties may be "targeted" to CEA-expressing cells by conjugation with CEA binding moieties of the present invention.

The term "cross-reactive" is used herein to describe binding associations between molecules akin to the binding of antibodies to antigens. It is to be understood to refer to non-covalent binding, not to the formation of covalent bonds.

The term "detectably labeled" is to be understood as including linking a molecule to a dye (such as fluorescein), a radionuclide (such as $^{131}$I), an enzyme (such as horseradish peroxidase), or detectable metal (such as a paramagnetic ion), which dye, radionuclide, enzyme or metal can thereafter be detected by appropriate means. The term "detectably labeled" also includes a binding moiety that has been synthesized to incorporate a radionuclide (such as $^{32}$P, $^{35}$S, or $^{14}$C) in place of a non-radioactive isotope of the same element.

DETAILED DESCRIPTION OF THE PREFERRED EMBODIMENTS

The present invention provides novel binding moieties for CEA. Such binding moieties make possible the efficient detection, imaging, localization, and targeting of CEA or CEA-related polypeptides in tissues or in a solution or system that contains CEA or CEA-related polypeptides. In particular, the binding moieties of this invention, when appropriately labeled, are useful for detecting, imaging, localizing, and targeting CEA-expressing cells or for diagnosing CEA specific pathophysiologies. The CEA binding polypeptides disclosed herein can thus be used to form a variety of diagnostic and therapeutic agents for diagnosing and treating CEA associated diseases, such as colon cancer and other cancers characterized by overexpression of CEA in cells, as compared with levels of CEA expression in corresponding cells of normal individuals. The preferred binding moieties of the present invention bind CEA with high affinity, i.e., acting at low, physiologically relevant concentrations, comparable to known anti-CEA antibodies and other CEA-binding proteins.

Preferred CEA binding polypeptides according to the invention will bind to CEA or a fragment thereof, but will not bind to other proteins that are known to be immunologically cross-reactive with CEA, such as NCA.

Specific CEA binding polypeptides according to the present invention were isolated initially by screening of phage display libraries, that is, populations of recombinant bacteriophage transformed to express an exogenous peptide loop on their surface. In order to isolate new polypeptide binding moieties for a particular target, such as CEA, screening of large peptide libraries, for example using phage display techniques, is especially advantageous, in that very large numbers (e.g., $5 \times 10^9$) of potential binders can be tested and successful binders isolated in a short period of time.

In order to prepare a phage library of potential binding polypeptides to screen for members of the library that might be CEA binding peptides, a candidate binding domain is selected to serve as a structural template for the peptides to be displayed in the library. The phage library is made up of analogues of this template or "parental domain". The binding domain template may be a naturally occurring or synthetic protein, or a region or domain of a protein. The binding domain template may be selected based on knowledge of a known interaction between the binding domain template and CEA, but this is not critical. In fact, it is not essential that the domain selected to act as a template for the library have any affinity for the target at all: Its purpose is to provide a structure from which a multiplicity (library) of similarly structured polypeptides (analogues) can be generated, which multiplicity of analogues will hopefully include one or more analogues that exhibit the desired binding properties (and any other properties screened for).

In selecting the parental binding domain or template on which to base the variegated amino acid sequences of the library, the most important consideration is how the variegated peptide domains will be presented to the target, i.e., in what conformation the peptide analogues will come into contact with the target. In phage display methodologies, for example, the analogues will be generated by insertion of synthetic DNA encoding the analogues into phage, resulting in display of the analogue on the surfaces of the phage. Such libraries of phage, such as M13 phage, displaying a wide variety of different polypeptides, can be prepared using techniques as described, e.g., in Kay et al., *Phage Display of Peptides and Proteins: A Laboratory Manual* (Academic Press, Inc., San Diego 1996) and U.S. Pat. No. 5,223,409 (Ladner et al.), both incorporated herein by reference.

The phage libraries used in the present invention are constructed in derivatives of the filamentous phage M13. The displayed peptides are fused to the amino terminus of protein III through a linker peptide which contains the recognition site for Factor Xa (the activated form of Factor X). Factor Xa can cleave the displayed peptide from the phage without injuring the phage or reducing its infectivity.

For formation of phage display libraries, it is preferred to use a structured polypeptide as the binding domain template, as opposed to an unstructured, linear peptide. Mutation of surface residues in a protein will usually have little effect on the overall structure or general properties (such as size, stability, and temperature of denaturation) of the protein; while at the same time mutation of surface residues may profoundly affect the binding properties of the protein. The more tightly a polypeptide segment is constrained, the less likely it is to bind to any particular target; however if the polypeptide does bind, the binding is likely to be of higher affinity and of greater specificity. Thus, it is preferred to select a parental domain and, in turn, a structure for the potential polypeptide binders, that is constrained within a framework having some degree of rigidity. In isolating the specific polypeptides according to this invention, four phage libraries were screen, each displaying a short, variegated exogenous peptide loop of 11, 12 or 16 amino acids on the surface of M 13 phage, at the amino terminus of protein III. The libraries were designated TN6/6 (having a potential $3.3 \times 10^{12}$ amino acid sequence diversity), TN7/1 (having a potential $5.6 \times 10^9$ amino acid sequence diversity), TN8/6 (having a potential $6.3 \times 10^9$ amino acid sequence diversity), and TN10/9 (having a potential $3 \times 10^{16}$ amino acid sequence diversity).

The TN6/6 library was constructed to display a single microprotein binding loop contained in a 12-amino acid template. The TN6/6 library utilized a template sequence of Xaa-Xaa-Xaa-Cys-Xaa-Xaa-Xaa-Xaa-Cys-Xaa-Xaa-Xaa (SEQ ID NO:10). The amino acids at the first and last positions in the template (amino acid positions 1 and 12) were varied to permit any amino acid selected from a group of 14 amino acids (i.e., Pro, Ala, Phe, Ser, Asp, Arg, Leu, Gly, His, Gln, Asn, Val, Trp, or Tyr); the amino acids at amino acid positions 2, 3, 5–8, 10, and 11 in the template were varied to permit any amino acid except cysteine (Cys). The number of potential designed sequences is $3.3 \times 10^{12}$; at least about $2.0 \times 10^8$ independent transformants were included in the library.

The TN7/1 library was constructed to display a single microprotein binding loop contained in an 11-amino acid template. The TN7/1 library utilized a template sequence of Xaa-Xaa-Cys-Xaa-Xaa-Xaa-Xaa-Xaa-Cys-Xaa-Xaa (SEQ ID NO:11). The amino acids at the first and last positions in the template (amino acid positions 1 and 11) were varied to permit any amino acid selected from a group of seven amino acids (i.e., Phe, His, Pro, Leu, Ala, Asp, or Arg); the amino acids at amino acid positions 2 and 10 in the template were varied to permit any amino acid selected from a group of nine amino acids (i.e., Leu, Gly, His, Ser, Asp, Arg, Pro, Ala, or Phe); the amino acids at amino acid positions 4, 5, 6, 7, and 8 (i.e., between the invariant cysteine residues in the template) were varied to permit any amino acid selected from a group of seventeen amino acids (i.e., Thr, Ile, Trp, Glu, Tyr, Gln, Asn, Val, Leu, Gly, His, Ser, Asp, Arg, Pro, Ala, or Phe). The number of potential designed sequences is $5.6 \times 10^9$; at least about $8.0 \times 10^7$ independent transformants were included in the library.

The TN8/6 library was constructed to display a single microprotein binding loop contained in a 12-amino acid template. The TN8/6 library utilized a template sequence of Xaa-Xaa-Cys-Xaa-Xaa-Xaa-Xaa-Xaa-Xaa-Cys-Xaa-Xaa (SEQ ID NO:12). The amino acids at the first and last positions in the template (amino acid positions 1 and 12) were varied to permit any amino acid selected from a group of four amino acids (i.e., Ala, Asp, Arg, or His); the amino acids at amino acid positions 2 and 11 in the template were varied to permit any amino acid selected from a group of nine amino acids (i.e., Pro, Ala, Phe, Ser, Asp, Arg, Leu, Gly, or His); the amino acids at amino acid positions 4, 5, 6, 7, 8 and 9 (i.e., between the invariant cysteine residues in the template) were varied to permit any amino acid selected from a group of thirteen amino acids (i.e., Pro, Ala, Phe, Ser, Asp, Arg, Leu, Gly, His, Gln, Asn, Val, or Trp). The number of potential designed sequences is $6.3 \times 10^9$; at least about $1.3 \times 10^8$ independent transformants were included in the library.

The TN10/9 library was constructed to display a single microprotein binding loop contained in a 16-amino acid template. The TN10/9 library utilized a template sequence Xaa-Xaa-Xaa-Cys-Xaa-Xaa-Xaa-Xaa-Xaa-Xaa-Xaa-Xaa-Cys-Xaa-Xaa-Xaa (SEQ ID NO:13). The amino acids amino acid positions 1, 2, 15 and 16 of the template were varied to permit any amino acid selected from a group of ten amino acids (i.e., Tyr, Arg, Ser, Trp, Leu, Asn, Pro, Asp, Phe, or His); the amino acids at amino acid positions 3 and 14 in the template were varied to permit any amino acid selected from a group of fourteen amino acids (i.e., Trp, Tyr, Arg, Ser, Val, Asn, Pro, Gln, Gly, His, Leu, Ala, Asp, or Phe); the amino acids at amino acid positions 5, 6, 7, 8, 9, 10, 11 and 12 (i.e., between the invariant cysteine residues in the template) were varied to permit any amino acid except cysteine. The number of potential designed sequences is $3.3 \times 10^{16}$; at least about $2.5 \times 10^8$ independent transformants were included in the library.

Such small binding loop peptides offer several advantages over large proteins: First, the mass per binding site is reduced, e.g., such highly stable and low molecular weight polypeptide domains can show much higher binding per gram than do antibodies (150 kDa) or single-chain antibodies (30 kDa). Second, the possibility of non-specific binding is reduced because there is less surface available. Third, small proteins or polypeptides can (because they are chemically synthesizable) be engineered to have unique tethering sites such as terminal polylysine segments in a way that is impracticable for larger proteins or antibodies. Fourthly, small peptides can be combined into homo- or heteromultimers to give either hybrid binding or avidity effects. Fifthly, a constrained polypeptide structure is more likely to retain its functionality when transferred with the structural domain intact from one framework to another, that is, the binding domain structure is likely to be transferable from the framework used for presentation in a library (e.g., displayed on a phage) to an isolated protein removed from the presentation framework or immobilized on a chromatographic or other substrate.

Each of the peptide loop libraries was created by making a designed series of mutations or variations within a coding sequence for the microprotein template, each mutant sequence encoding a binding loop analogue peptide corresponding in overall structure to the template except having one or more amino acid variations in the sequence of the template. The novel variegated (mutated) DNA provides sequence diversity, and each transformant phage displays one variant of the initial template amino acid sequence encoded by the DNA, leading to a phage population (library) displaying a vast number of different but structurally related amino acid sequences. The phage display libraries screened for CEA binders contained from 100 million to 1 billion variants of the respective parental domain peptides. The amino acid variations are expected to alter the binding properties of the binding loop or domain without significantly altering its structure, at least for most substitutions. It is preferred that the amino acid positions that are selected for variation (variable amino acid positions) will be surface amino acid positions, that is, positions in the amino acid sequence of the domains which, when the domain is in its most stable conformation, appear on the outer surface of the domain (i.e., the surface exposed to solution). Most preferably the amino acid positions to be varied will be adjacent or close together, so as to maximize the effect of substitutions.

As indicated previously, the techniques discussed in Kay et al., *Phage Display of Peptides and Proteins: A Laboratory Manual* (Academic Press, Inc., San Diego 1996) and U.S. Pat. No. 5,223,409 are particularly useful in preparing a library of potential binders corresponding to the selected parental template. The four libraries described above were prepared according to such techniques, and they was screened for CEA binding polypeptides against an immobilized CEA-relevant target (i.e., a synthetic fusion peptide target composed of a hexahistidine leader, the N domain of CEA and the A3 domain of CEA, designated "H6NA3").

In a typical screen, a phage library is contacted with and allowed to bind the target, in this case, CEA or a particular subcomponent(s), such as NA3, preferably presenting structures unique to CEA (i.e., structures not cross-reactive with NCA or other CEA-like antigens). The H6NA3 target was selected because the A3 domain was believed to be unique to CEA; antibodies that bind A3 do not cross-react with other CEA-related antigens, such as NCA.

To facilitate separation of binders and non-binders, it is convenient to immobilize the target on a solid support. When incubated in the presence of the target, phage bearing a target-binding moiety form a complex with the target on the solid support whereas non-binding phage remain in solution and may be washed away with buffer. Bound phage may then be liberated from the target by a number of means, such as changing the buffer to an extreme pH (pH 2 or pH 10), changing the ionic strength of the buffer, adding denaturants, or other known means. In the present case, CEA binders associating with immobilized target NA3 were eluted either by competition with a known CEA binding antibody (cT84.66, a chimeric mouse/human anti-A3 antibody supplied by The City of Hope, Duarte Calif.) or by cleavage with Factor Xa.

The recovered phage may then be amplified through infection of bacterial cells and the screening process repeated with the new pool that is now depleted in non-binders and enriched in binders. The recovery of even a few binding phage is sufficient to carry the process to completion. After a few rounds of selection, the gene sequences encoding the binding moieties derived from selected phage clones in the binding pool are determined by conventional methods, described below, revealing the peptide sequence that imparts binding affinity of the phage to the target. When the selection process works, the sequence diversity of the population falls with each round of selection until only good binders remain. The sequences converge on a small number of related binders, typically 10–50 out of the more than 100 million original candidates. An increase in the number of phage recovered at each round of selection, and of course, the recovery of closely related sequences are good indications that convergence of the library has occurred in a screen. After a set of binding polypeptides is identified, the sequence information may be used to design other secondary phage libraries, biased for members having additional desired properties. Once CEA binders have been initially isolated and characterized, further screening for additional ("improved") CEA binders can be performed, for example, by creating a "biased" library derived from a consensus amino acid sequence of initial Isolates and/or by increasing the stringency of the screen (see infra).

After analysis of the sequences isolated from the library screening, a family of particular CEA binders was defined. In addition, important consensus motifs were observed. The following sequences conforming to the TN10/9 template were found to bind a CEA target:

```
Asn-Trp-Val-Cys-Asn-Leu-Phe-Lys-Asn-Gln-Trp-Phe-Cys-Asn-Ser-Tyr   (SEQ ID NO:4)
(FX-G08)

Asp-Trp-Val-Cys-Glu-Asn-Lys-Lys-Asp-Gln-Trp-Thr-Cys-Asn-Leu-Leu   (SEQ ID NO:5)
(AB-A07);

Asn-Trp-Asp-Cys-Met-Phe-Gly-Ala-Glu-Gly-Trp-Ala-Cys-Ser-Pro-Trp   (SEQ ID NO:6)
(TN10/9-E01);

Asp-Trp-Val-Cys-Glu-Lys-Thr-Thr-Gly-Gly-Tyr-Val-Cys-Gln-Pro-Leu   (SEQ ID NO:7)
(TN10/9-B09);

Asn-Trp-Phe-Cys-Glu-Met-Ile-Gly-Arg-Gln-Trp-Gly-Cys-Val-Pro-Ser   (SEQ ID NO:8)
(TN10/9-F11); and Asp-Trp-Val-Cys-Asn-Phe-Asp-Gln-Gly-Leu-Ala-His-Cys-Phe-Pro-Ser   (SEQ ID NO:9)
(TN10/9-G01).
```

When displayed on the phage, these peptides are expected to form a disulfide bond between the Cys residues. In the synthetic peptides, the cysteines are preferably oxidized to form a disulfide.

This series of CEA binders defines a family of polypeptides including the amino acid sequence:

$X_1$-$X_2$-$X_3$-Cys-$X_4$-$X_5$-$X_6$-$X_7$-$X_8$-$X_9$-$X_{10}$-$X_{11}$-Cys-$X_{12}$-$X_{13}$-$X_{14}$ (SEQ ID NO:111), wherein:

```
X1 is Asn, Asp, Ala, Ile, or is absent;

X2 is Trp;

X3 is Val, Ile, Met, Tyr, Phe, Pro, or Asp;

X4 is Asn, Glu, Asp, or Met;

X5 is Leu, Phe, Tyr, Trp, Val, Met, Ile, or Asn;

X6 is Phe, Leu, Asp, Glu, Ala, Ile, Lys, Asn, Ser,
Val, Trp, Tyr, Gly, or Thr;

X7 is Lys, Phe, Asp, Gly, Leu, Asn, Trp, Ala, Gln,
or Thr;

X8 is Asn, Pro, Phe, Gly, Asp, Ala, Ser, Glu, Gln,
Trp, His, Arg, Met, Val, or Leu;

X9 is Gln, Lys, Leu, or Gly;
```

-continued

```
X10 is Ala, Trp or Tyr;

X11 is Phe, Thr, Met, Ser, Ala, Asn, Val, His, Ile,
Pro, Trp, Tyr, Gly, Leu, or Glu;

X12 is Asn, Asp, Glu, Pro, Gln, Ser, Phe, or Val;

X13 is Val, Leu, Ile, Pro, Ala, Gln, Ser, Met, Glu,
Thr, Lys, Trp, or Arg; and

X14 is Leu, Met, Val, Tyr, Ala, Ile, Trp, His, Pro,
Gln, Glu, Phe, Lys, Arg, or Ser;
``` and wherein said polypeptide has the ability to bind CEA.

The cysteine residues of the microprotein are believed to form a disulfide bond, which causes the microprotein to form a stable loop structure under non-reducing conditions. Thus, the invention relates to the discovery of a CEA binding loop comprising a polypeptide having the amino acid sequence: Cys-$X_4$-$X_5$-$X_6$-$X_7$-$X_8$-$X_9$-$X_{10}$-$X_{11}$-Cys (SEQ ID NO:110), wherein:

```
X4 is Asn, Glu, Asp, or Met;

X5 is Leu, Phe, Tyr, Trp, Val, Met, Ile, or Asn;

X6 is Phe, Leu, Asp, Glu, Ala, Ile, Lys, Asn, Ser,
Val, Trp, Tyr, Gly, or Thr;

X7 is Lys, Phe, Asp, Gly, Leu, Asn, Trp, Ala, Gln,
or Thr;

X8 is Asn, Pro, Phe, Gly, Asp, Ala, Ser, Glu, Gln,
Trp, His, Arg, Met, Val, or Leu;

X9 is Gln, Lys, Leu, or Gly;

X10 is Ala, Trp or Tyr; and

X11 is Phe, Thr, Met, Ser, Ala, Asn, Val, His, Ile,
Pro, Trp, Tyr, Gly, Leu, or Glu.
```

Recurrent sequences among Isolates recovered in screens and recurrence of certain amino acids at the same positions within the isolate peptides gives rise to a preferred family of CEA binding peptides and a sequence that may be useful for designing a secondary, directed library for obtaining even higher affinity CEA binders. The preferred family of peptides have amino acid sequences of the formula:

```
X1-Trp-Val-Cys-Glu-X5-X6-Lys-X8-    (SEQ ID NO:2)
Gln-Trp-X11-Cys-Asn-X13-X14,
wherein X1 is Asn or Asp;

X5 is Asn, Leu, Met or Phe;

X6 is Asp, Gly, Ile, Lys, Phe or
Thr;

X8 is Arg, Asn, Asp, Glu, or Gly;

X11 is Ala, Gly, His, Phe, Thr or
Val;

X13 is Arg, Leu, Pro or Ser; and

X14 is Leu, Ser, Trp or Tyr.
```

The invention also involves a library of phage focused on improved binders to CEA. This library was constructed from seven sublibraries, each sublibrary allowing five amino acid positions to vary while holding constant nine of the amino acid positions that were varied in the initial library (TN10/9). The template structure of the seven sublibraries allowed variegation in the forms:

Var1: $X_1$-$X_2$-$X_3$-Cys-$X_4$-$X_5$-Lys-Lys-Asp-Gln-Trp-Thr-Cys-Asn-Leu-Leu (SEQ ID NO:14)

Var2: Asp-Trp-Val-Cys-$X_4$-$X_5$-$X_6$-$X_7$-$X_8$-Gln-Trp-Thr-Cys-Asn-Leu-Leu (SEQ ID NO:15)

Var3: Asp-Trp-Val-Cys-Glu-Asn-Lys-$X_7$-$X_8$-$X_9$-$X_{10}$-$X_{11}$-Cys-Asn-Leu-Leu (SEQ ID NO:16)

Var4: Asp-Trp-Val-Cys-Glu-Asn-Lys-Lys-Asp-Gln-$X_{10}$-$X_{11}$-Cys-$X_{12}$-$X_{13}$-$X_{14}$ (SEQ ID NO:17)

Var5: Asp-Trp-Val-Cys-Glu-$X_5$-$X_6$-Lys-$X_8$-Gln-Trp-$X_{11}$-Cys-Asn-$X_{13}$-Leu (SEQ ID NO:18)

Var6: Asn-Trp-Val-Cys-$X_4$-$X_5$-$X_6$-Lys-$X_8$-Gln-Trp-$X_{11}$-Cys-Asn-Ser-Tyr (SEQ ID NO:19)

Var7: $X_1$-Trp-$X_3$-Cys-Asn-Leu-Phe-Lys-Asn-Gln-Trp-Phe-Cys-$X_{12}$-$X_{13}$-$X_{14}$ (SEQ ID NO:20), wherein each X residue was allowed to be, with approximately equal likelihood, each of the genetically encodable amino acids except cysteine. The invariant portions of sequences Var1 through Var5 were based on the most frequently observed CEA binder sequence in the initial screening of TN10/9 (see, SEQ ID NO:5, Isolate AB-A07). The invariant portions of sequences Var6 through Var7 were based on the binding peptide observed to have the best dissociation constant (see, SEQ ID NO:4, Isolate FX-G08).

Additional, preferred CEA binding peptides were isolated from this focused library having the sequences as shown in Tables 5, 8, and 9 (infra).

Direct synthesis of the peptides of the invention disclosed herein may be accomplished using conventional techniques including, preferably, solid-phase peptide synthesis, although solution-phase synthesis may also be used. In solid-phase synthesis, for example, the synthesis is commenced from the carboxy-terminal end of the peptide using an α-amino protected amino acid. t-Butyloxycarbonyl (Boc) protective groups can be used for all amino groups, though other protective groups are suitable. See, Stewart et al., *Solid-Phase Peptide Synthesis* (1989), W. H. Freeman Co., San Francisco; and Merrifield, *J. Am. Chem. Soc.*, 85:2149–2154 (1963).

Polypeptides according to the invention may also be prepared commercially by companies providing peptide synthesis as a service (e.g., BACHEM Bioscience, Inc., King of Prussia, Pa.; Quality Controlled Biochemicals, Inc., Hopkinton, Mass.).

Automated peptide synthesis machines, such as manufactured by Perkin-Elmer Applied Biosystems, also are available.

The polypeptide compound is preferably purified once it has been isolated or synthesized by either chemical or recombinant techniques. For purification purposes, there are many standard methods that may be employed including reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can also be used to separate peptides based on their charge. The degree of purity of the polypeptide may be determined by various methods, including identification of a major large peak on HPLC. A polypeptide that produces a single peak that is at least 95% of the input material on an HPLC column is preferred. Even more preferable is a polypeptide that produces a single peak that is at least 97%, at least 98%, at least 99% or even 99.5% of the input material on an HPLC column.

In order to ensure that the peptide obtained using any of the techniques described above is the desired peptide for use in compositions of the present invention, analysis of the peptide composition may be carried out. Such composition analysis may be conducted using high resolution mass spectrometry to determine the molecular weight of the peptide. Alternatively, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

The new class of CEA binding polypeptides is designed to be conformationally restrained by disulfide linkages between the two cysteine residues in their sequence. This conformational restraint ensures that the peptides have a stable binding structure that contributes to the peptides' affinity for CEA and their specificity for CEA over non-CEA proteins. Other methods for constraining peptides which would retain a similar conformation and CEA specificity for the peptide have been described in the art and are contemplated herein, including the substitution of one or more of the cysteine residues with non-naturally occurring amino acids or peptidomimetics for the purpose of forming a more stable or conformationally preferred linkage between the two positions on the peptide. All such modified CEA binding moieties are also considered CEA binding moieties so long as they retain the ability to bind CEA or a portion thereof. Non-cyclized, or linear, versions of the peptides may also retain moderate binding ability and specificity for CEA and could also be employed in the present invention.

Homologues of the CEA binding polypeptides described herein, as well as homologues to any subsequently discovered CEA binding polypeptides, may be formed by substitution, addition or deletion of one or more amino acids employing methods well known in the art and for particular purposes known in the art, such as addition of a polyhistidine "tail" in order to assist in purification or substitution of one up to several amino acids in order to obliterate an enzyme cleavage site. Other specifically contemplated homologues include polypeptides having N-terminal or C-terminal modifications or linkers, such as polyglycine or polylysine segments, and alterations to include functional groups, notably hydrazide (—NH—NH$_2$) functionalities, to assist in immobilization of binding peptides according to this invention on solid supports.

Such homologous polypeptides will be understood to fall within the scope of the present invention so long as the substitution, addition or deletion of amino acids does not eliminate its ability to bind CEA.

The term "homologous", as used herein, refers to the degree of sequence similarity between two polymers (i.e., polypeptide molecules or nucleic acid molecules). When the same nucleotide or amino acid residue occupies a sequence position in the two polymers under comparison, then the polymers are homologous at that position. The percent homology between two polymers is the mathematical relationship of the number of homologous positions shared by the two polymers divided by the total number of positions compared, the product multiplied by 100. For example, if the amino acid residues at 60 of 100 amino acid positions in two polypeptide sequences match or are homologous then the two sequences are 60% homologous. The homology percentage figures referred to herein reflect the maximal homology possible between the two polymers, i.e., the percent homology when the two polymers are so aligned as to have the greatest number of matched (homologous) positions. Polypeptide homologues within the scope of the present invention will be at least 85% and preferably greater than 90% homologous to at least one of the CEA binding sequences disclosed herein.

CEA binding polypeptides according to the present invention also may be produced using recombinant DNA techniques, utilizing nucleic acids (polynucleotides) encoding the polypeptides according to this invention and then expressing them recombinantly, i.e., by manipulating host cells by introduction of exogenous nucleic acid molecules in known ways to cause such host cells to produce the desired CEA binding polypeptides. Recombinant production of short peptides (e.g., 16-mers) such as those described herein may not be advantageous in comparison to direct synthesis, however recombinant means of production may be very advantageous where a CEA binding motif of this invention are desired to be incorporated in a hybrid polypeptide or fusion protein.

The polynucleotides of the present invention may be in the form of RNA or in the form of DNA, which DNA includes cDNA and synthetic DNA. The DNA may be double-stranded or single-stranded, and if single stranded may be the coding strand or non-coding (anti-sense) strand. The coding sequences for CEA binding polypeptides according to the present invention may be manipulated or varied in known ways to yield alternative coding sequences that, as a result of the redundancy or degeneracy of the genetic code, encode the same polypeptide.

The polypeptides and polynucleotides of the present invention are preferably provided in an isolated form, and preferably are purified to homogeneity.

Where recombinant production of CEA binding polypeptides is desired, the present invention also contemplates vectors that include polynucleotides of the present invention, host cells that are genetically engineered with vectors of the invention, and recombinant polypeptides produced by culturing such genetically engineered host cells. Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the CEA binder-encoding polynucleotides. The culture conditions, such as temperature, pH and the like, are those suitable for use with the host cell selected for expression and will be apparent to the skilled practitioner in this field. The polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host. The appropriate DNA sequence may be inserted into the vector by a variety of procedures. In general, the DNA sequence is inserted into an appropriate restriction endonuclease site(s) by procedures known in the art. Such procedures and others are within the capability of those skilled in the art.

The DNA sequence in the expression vector is operatively linked to an appropriate expression control sequence(s) (promoter) to direct mRNA synthesis. As representative examples of such promoters, there may be mentioned LTR or SV40 promoter, the *E. coli* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression. In addition, expression vectors preferably will contain one or more selectable marker genes to provide a phenotypic trait for selection of transformed host cells, such as dihydrofolate reductase or neomycin resistance for eukaryotic cell culture, or such as tetracycline or ampicillin resistance for bacterial cell cultures such as *E. coli*.

The vector containing the appropriate DNA sequence as hereinabove described, as well as an appropriate promoter or control sequence, may be employed to transform an appropriate host to permit the host to express the protein. As representative examples of appropriate host cells, there may be mentioned bacterial cells, such as *E. coli, Streptomyces, Salmonella typhimurium*; fungal cells, such as yeast; insect cells such as *Drosophila* and Sf9; animal cells such as CHO, COS or Bowes melanoma; plant cells, etc. The selection of an appropriate host for this type of CEA binder production is also within the capability of those skilled in the art from the teachings herein. Many suitable vectors and promoters useful in expression of proteins according to this invention are known to those of skill in the art, and many are commercially available. The following vectors are provided by way of example. Bacterial: pQE70, pQE60, pQE-9 (Qiagen), pBS(+ or −), pD10, pHagescript, psiX174, pBluescript SK, pBSKS, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). Any other plasmid or vector may be used as long as it is replicable and viable in the selected host cell.

Introduction of the vectors into the host cell can be effected by any known method, including calcium phosphate transfection, DEAE-Dextran mediated transfection, or electroporation (see Davis et al., *Basic Methods in Molecular Biology* (1986); Sambrook et al., *Molecular Cloning*, ISBN 0-87969-309-6, (1987)).

In the practice of the present invention, a determination of the affinity of the CEA binding moiety for CEA relative to other components of a sample is a useful measure, and is referred to as specificity for CEA. Standard assays for quantitating binding and determining affinity include equilibrium dialysis, equilibrium binding, gel filtration, surface plasmon resonance, microbalances (Hengerer et al., Biotechniques, 26(5):956–60, 962, 964 (1999)) or the monitoring of numerous spectroscopic changes (such as fluorescence) that may result from the interaction of the binding moiety and its target. These techniques measure the concentration of bound and free ligand as a function of ligand (or protein) concentration. The concentration of bound polypeptide ([Bound]) is related to the concentration of free polypeptide ([Free]) and the concentration of binding sites for the polypeptide, i.e., on CEA, (N=total CEA), as described in the following equation:

$$[Bound]=N\times[Free]/((K_D)+[Free]).$$

A solution of the data to this equation yields the dissociation constant, $K_D$, a quantitative measure of the binding affinity. The association constant, $K_a$ is the reciprocal of the dissociation constant, $K_D$. A peptide having a $K_D$ 2 times higher for HSA (or some other non-CEA target such as NCA) than for CEA would be considered as a weak CEA binder. A peptide having a $K_D$ 10 times greater for HSA than CEA would be a moderate CEA binder, and a peptide having a $K_D$ 100 times or more greater for HSA than for CEA would be termed highly specific for CEA. Preferably the peptides and agents of the present invention have a $K_D$ at least 2 times higher for HSA than for CEA, more preferably at least 10 times higher, even more preferably at least 100 times, and most preferably at least 1000 times higher.

For most uses, the lower the dissociation constant, the better. Preferred CEA binders according to the invention will have a $K_d$ for CEA of less than 10 µM, more preferred CEA binders will have a $K_d$ for CEA of less than 1 µM, and most preferred CEA binders will have a $K_d$ for CEA less than 0.1 µM or lower. The first set of CEA binders isolated from the TN10/9 library had a $K_d$ for CEA in the range of 1 µM to 7 µM.

Uses for CEA Binding Polypeptides

The CEA binding moieties according to this invention will be useful for detecting the presence of CEA in blood or other biological fluids and/or for localizing or imaging of CEA expression in vitro or in vivo, and particularly for detection and/or imaging of CEA-expressing cells and tissues. Any suitable method of assaying or imaging CEA may be employed.

Detection of CEA

Assays for CEA using the CEA binding moieties of the present invention can be direct binding, competitive binding, or sandwich assays. The CEA binding moiety can be attached to a surface and used in a surface-plasmon resonance or microbalance to detect the binding of CEA directly.

Alternatively, bacteriophage that display a CEA binding peptide can be incubated with cells to be tested for CEA expression. The cells can be spun down in a manner that does not sediment the phage, and the presence of phage in the cell pellet can then be detected with labeled antibodies that bind to the phage. Another useful detection assay utilizes detectably labeled CEA binding moiety, which is mixed with cells to be tested for surface expression of CEA. After incubation, the cells are spun down and the presence (or absence) of CEA is detected by the presence (or absence) of the label in the cell pellet.

In a further detection method, a CEA binding moiety can be immobilized, a sample to be tested is contacted with the immobilized CEA binding moiety, and after incubation, the sample is removed and the container washed. The presence of CEA is detected with a detectably labeled antibody that binds CEA. This antibody need not distinguish between CEA and other cross-reactive antigens where preferred polypeptides according to this invention are used, because only CEA will have been captured by the immobilized binding moiety (which, in preferred features, is specific for CEA and not for cross-reactive species such as NCA).

In another method, a CEA binding moiety of the present invention is immobilized in a well; detectably labeled CEA is bound to the CEA binding moiety; a sample is then added, and the presence or absence of CEA is detected by the release of the labeled CEA or the retention of the labeled CEA.

For detection or purification of CEA or CEA-expressing cells in or from a solution, a binding moiety of the invention can be immobilized on a solid substrate such as a chromatographic support or other porous material, then the immobilized binding moiety can be loaded or contacted with the solution under conditions suitable for formation of a binding moiety/CEA complex. The non-binding portion of the solution can be removed and the complex may be detected, e.g., using an anti-CEA or anti-binding moiety antibody, or the CEA target may be released from the binding moiety at appropriate elution conditions.

Tumor Imaging

A particularly preferred use for the polypeptides according to the present invention is for creating visually readable images of tumors including neoplastic cells expressing high levels of CEA, to aid in the diagnosis, monitoring and treatment of CEA associated cancers or other disorders.

The CEA binding moieties disclosed herein may be converted to imaging reagents for detecting CEA-expressing tumors by conjugating the polypeptides with a label appropriate for diagnostic detection. Preferably, a CEA binding polypeptide exhibiting much greater specificity for CEA than for NCA is used. A polypeptide according to this invention may be conjugated or linked to a label appropriate for the detection methodology to be employed. For example, the CEA binder may be conjugated with a paramagnetic chelate suitable for magnetic resonance imaging (MRI), with a radiolabel suitable for x-ray imaging, with an ultrasound microsphere or liposome suitable for ultrasound detection, or with an optical imaging dye.

Suitable linkers for conjugating the polypeptide binder to a detectable label can be substituted or unsubstituted alkyl chains, amino acid chains (e.g., polyglycine), polyethylene glycols, polyamides, and other simple polymeric linkers known in the art. Many heterobifunctional linkers are also known and are commercially available. Detectable labels may also be bound directly to the CEA binding moieties, e.g., at a lysine side chain or other reactive site that does not interfere with CEA/binding moiety interaction.

Molecules that contain multiple copies of a CEA-binding moiety are likely to have longer residence times both at the tumor and in circulation. It is desirable to have an agent that is intended to bind CEA for either imaging or therapy to remain in circulation for at least a few hours so that it has time to reach the tumor. Once the agent has reached the tumor, it is desirable that it stay there as long as possible.

Many techniques are known for preparing multimeric forms of binding molecules, and such techniques may be used to prepared CEA binding multimers having increased serum half life and higher avidity for CEA. For example, one of the CEA binding peptides of the present invention can be synthesized with a C-terminal extension of Gly-Gly-Lys. The side groups of the other residues are protected in one way and the terminal Lys side group and carboxyl groups are protected in an orthogonal manner. The terminal Lys amine group is deprotected and a chelator group is attached. The carboxyl groups is deprotected and two copies are joined using bifunctional polyethylene glycol reagents. The other protecting groups are removed. Just before use, a suitable radionuclide is added. For imaging $^{99M}$Tc is a preferred radionuclide and HYNIC is a preferred chelator. Alternatively, moieties other than chelators could be coupled to the lysine extension. Whole antibodies show detectable avidity effects when binding to CEA. Thus comparable avidity effects are expected in a dimerized binding peptide according to the invention.

Preferably, the peptide moieties of a multimer (e.g., homo- and hetero-dimers, trimers, and tetramers) are separated by a linker, more preferably a hydrophilic linker. For example, the peptide moieties of one molecule may be separated by a distance similar to the separation between the combining sites of an antibody (i.e., on the order of 100 Å). One preferred linker contains from about 1 to about 100 units of —(CH$_2$—CH$_2$—O)—, to allow separation and to increase the serum residence time. Preferably, the linker contains from about 50 to about 80 units of —(CH$_2$—CH$_2$—O)—.

In general, the technique of using a detectably labeled CEA binding moiety in vivo for diagnosis is based on the premise that the label generates a signal that is detectable outside the patient's body. When the detectably labeled CEA binding moiety is administered to the patient suspected of having a CEA-expressing tumor, the high affinity of the CEA binding moiety for CEA on a tumor causes the CEA binding moiety to bind to the tumor and accumulate label at the site of the tumor. Sufficient time is allowed for the labeled peptide to localize at the site of the tumor. The signal generated by the labeled peptide may then be detected by a scanning device that will vary according to the type of label used, and the signal is then converted to an image of the tumor.

Therapeutic Applications

The CEA binding moieties of the present invention can be used to improve the activity of anti-cancer drugs or tumor-killing agents by providing or improving their affinity for CEA. In this aspect of the invention, hybrid anti-tumor agents are provided by conjugating a CEA binding moiety according to the invention with a drug or other agent lethal to the tumor. The CEA binding moiety component of the conjugate causes the anti-tumor agent to target the sites of CEA-expressing cells, and to improve the affinity of the conjugate for the cells, so that the anti-tumor activity of the conjugate is more localized and concentrated at the sites of tumors. Such conjugates will be useful in treating CEA associated diseases, especially colon cancer, in humans and animals, which method comprises administering to a human or animal in need thereof an effective amount of a CEA binding moiety according to the invention conjugated with an appropriate therapeutic agent. The invention also provides the use of such conjugates in the manufacture of a medicament for the treatment of diseases associated with the overexpression of CEA by cells in humans and animals.

A CEA binding moiety of the present invention may be advantageously used to target a toxin, radioactivity, cytolytic T cells, cytokines, chemotherapeutic agents or other molecules to a tumor expressing CEA.

In the above treatment method, the compounds may be administered by any convenient route customary for anti-tumor treatments, for example by infusion or bolus injection. In a preferred embodiment, the composition may be formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anaesthetic such as lignocaine to ease pain at the site of the injection. Generally, the ingredients will be supplied either separately or mixed together in unit dosage form, for example, as a dry lyophilized powder or water free concentrate in a hermetically sealed container such as an ampoule or sachette indicating the quantity of active agent in activity units. Where the composition is to be administered by infusion, it can be dispensed with an infusion bottle containing sterile pharmaceutical grade "water for injection" or saline. Where the composition is to be administered by injection, an ampoule of sterile water for injection or saline may be provided so that the ingredients may be mixed prior to administration.

The quantity of material administered will depend on the seriousness of the condition and position and size of the tumor. The precise dose to be employed and mode of administration must per force in view of the nature of the complaint be decided according to the circumstances by the physician supervising treatment. In general, dosages of the CEA binder/anti-tumor agent conjugate will follow the dosages that are routine for the anti-tumor agent alone, although the improved affinity for CEA added by the CEA binder component may allow a decrease in the standard dosage.

Isolation of CEA binding moieties in accordance with this invention will be further illustrated in the following examples. The specific parameters included in the following examples are intended to illustrate the practice of the invention, and they are not presented to in any way limit the scope of the invention.

EXAMPLE 1

Preparation of a CEA Target for Library Screening

For screening libraries to isolate binding moieties for CEA, a truncated target protein, i.e., H6NA3, consisting of a hexahistidine leader and the N and A3 domains of CEA, was used, based on a presumption that binders directed at the A3 domain would not be cross-reactive with other antigens, such as NCA, having a high degree of homology to CEA. The recombinantly produced H6NA3 protein was dispersed in PBS and added to the wells of a 96-well polystyrene microtiter plate, at 1 µg/well. The plate was allowed to stand overnight at 4° C., which was effective to immobilize target H6NA3 antigen on the plate.

EXAMPLE 2

Screening of Phage Display Libraries

Four phage display libraries were used in the initial screening for CEA binding moieties. The libraries were designated TN6/6, TN7/1, TN8/6 and TN10/9.

The TN6/6 phage display library was composed of recombinant M13 phage displaying variegated exogenous single-loop peptides based on a microprotein template having the structure Xaa-Xaa-Xaa-Cys-Xaa-Xaa-Xaa-Xaa-Cys-Xaa-Xaa-Xaa (SEQ ID NO:10). 2.0×10$^8$ transformants (at 6.0× 10$^9$ pfu/ml) were screened.

The TN7/1 phage display library was composed of recombinant M13 phage displaying variegated exogenous single-loop peptides based on a microprotein template having the structure Xaa-Xaa-Cys-Xaa-Xaa-Xaa-Xaa-Xaa-Cys-Xaa-Xaa (SEQ ID NO:11). $8.0 \times 10^7$ transformants (at $7.0 \times 10^9$ pfu/ml) were screened.

The TN8/6 phage display library was composed of recombinant M13 phage displaying variegated exogenous single-loop peptides based on a microprotein template having the structure Xaa-Xaa-Cys-Xaa-Xaa-Xaa-Xaa-Xaa-Xaa-Cys-Xaa-Xaa (SEQ ID NO:12). $1.3 \times 10^8$ transformants (at $7.5 \times 10^9$ pfu/ml) were screened.

The TN10/9 phage display library was composed of recombinant M13 phage displaying variegated exogenous single-loop peptides based on a microprotein template having the structure Xaa-Xaa-Xaa-Cys-Xaa-Xaa-Xaa-Xaa-Xaa-Xaa-Xaa-Xaa-Cys-Xaa-Xaa-Xaa (SEQ ID NO:13). $2.5 \times 10^8$ transformants (at $7.0 \times 10^9$ pfu/ml) were screened.

All of the libraries were constructed so that the phage expressed a variegated peptide at the amino terminus of protein III, and a constant Factor Xa cleavage site was provided between the display peptide and mature protein III. Each library was separately diluted into 100 $\mu$L of binding buffer (50 mM Tris, 150 mM NaCl, 2 mM $CaCl_2$, 0.05% Tween-20) before addition to H6NA3-coated wells.

Each library was allowed to interact with the target separately. After a 2-hour incubation with the target to allow binding, the wells of the plate were washed extensively (minimum 10 times) to remove unbound or weakly bound phage. Bound phage were recovered by elution under two conditions: first, by competitive binding with a second CEA ligand, namely, a chimeric mouse/human anti-A3 monoclonal antibody, cT84.66 (added at 333 nM), followed by a Factor Xa cleavage elution. Phage fractions of the competitive antibody elution (AbE) and the Factor X elution (FXE) were recovered and propagated separately overnight.

The amplified phage were concentrated (AbE and FXE separately), re-exposed to the target and eluted with antibody or Factor Xa (respectively). This procedure was repeated two more times. A progressive increase in the elution titer following each of the four rounds of screening indicated selection of phage having affinity for the NA3 target.

EXAMPLE 3

Analysis of Individual Isolates

After four rounds of selection, the eluted phage were propagated and a portion plated to isolate phage plaques arising from individual clones. Ninety-four such clones were selected randomly, propagated, and tested individually for binding to NA3 in a dried H6NA3 plate ELISA. Dried H6NA3 plates were prepared as described above for the library screening. Phage samples (~$10^9$ phage each) were incubated in the H6NA3 plate wells in binding buffer (50 mM Tris, 150 mM NaCl, 2 mM $CaCl_2$, 0.05% Tween-20) containing 0.1% HSA. After 1 hour, the plates were washed 5 times with binding buffer. Polyclonal anti-M13 antibody conjugated to horseradish peroxidase (Pharmacia) was added at 1/5000 dilution in binding buffer to the wells and incubated for 1 hour. The wells were again washed 5 times with binding buffer and the presence of the antibody/phage/NA3 complex was measured with HRP calorimetric reagents (3,3',5,5'-tetramethylbenzidine (TMB) and $H_2O_2$). A high absorbance at 630 nm (due to oxidized TMB) was indicative of a tight phage/NA3 interaction, and phage clones corresponding to those wells were identified as bearing CEA-binding moieties.

ELISAs to assay binding to immobilized HSA (passively bound to the polystyrene plate) and a target-free microtiter plate were controls to eliminate phage that bound promiscuously or nonspecifically.

The amino acid sequences of the phage-displayed polypeptides from the ELISA positive clones (those positive for NA3 but negative for HSA and the polystyrene plate) were deduced by DNA sequencing. The amino acid sequence data from these phage Isolates were sorted according to the degree of similarity and response in the H6NA3 plate ELISA. The results of the screen from the TN10/9 library are set forth in Table 1.

TABLE 1

Amino acid sequences of CEA-binding polypeptides from the TN10/9 library

| TN10/9 Isolate | sequence | competition elution (AbE) | cleavage elution (FXE) | overall fraction (94) | SEQ ID NO: |
|---|---|---|---|---|---|
| G08 | NWVCNLFKNQWFCNSY | 0/46 (0.00) | 6/48 (0.125) | 6/94 (0.064) | 4 |
| A07 | DWVCENKKDQWTCNLL | 42/46 (0.91) | 33/48 (0.69) | 75/94 (0.80) | 5 |
| E01 | NWDCMFGAEGWACSPW | 2/46 (0.04) | 0/48 (0.00) | 2/94 (0.043) | 6 |
| B09 | DWVCELTTGGYVCQPL | 1/46 (0.022) | 0/48 (0.00) | 1/94 (0.011) | 7 |
| F11 | NWFCEMIGRQWGCVPS | 0/46 (0.00) | 4/48 (0.083) | 4/94 (0.043) | 8 |
| D04 | DWVCNFDQGLAHCFPS | 0/46 (0.00) | 1/48 (0.021) | 1/94 (0.011) | 9 |
| G01 | NWRCKLFPRYPYCSSW | 0/46 (0.00) | 1/48 (0.021) | 1/94 (0.011) | 21 |
| B10 | -RYCEFFPWSLHCGRP | 1/46 (0.022) | 3/48 (0.063) | 4/94 (0.043) | 22 |

The screens of the TN6/6, TN7/1 and TN8/6 libraries did not result in recovery of any high affinity CEA binders. Peptides G01 (SEQ ID NO:21) and B10 (SEQ ID NO:22) were later found not to bind CEA with useful affinity.

EXAMPLE 4

Sequence Conservation Among TN10/9 Isolates

The polypeptide sequences binding to the H6NA3 target define a cysteine-bracketed CEA binding loop of ten amino acids (including the cysteines), viz., $Cys-X_4-X_5-X_6-X_7-X_8-X_9-X_{10}-X_{11}-Cys$ (SEQ ID NO:3), wherein $X_4$ is Asn, Glu or Met;

$X_5$ is Asn, Leu, Met or Phe;

$X_6$ is Asp, Gly, Ile, Lys, Phe or Thr;

$X_7$ is Ala, Gln, Gly, Lys or Thr;

$X_8$ is Arg, Asn, Asp, Glu or Gly;

-continued

X₉ is Gln, Gly, Leu or Ser;

X₁₀ is Ala, Trp or Tyr; and

X₁₁ is Ala, Gly, His, Phe, Thr or Val, which forms a stable binding site for CEA.

It is also clear from the selected Isolates that one particular sequence, that of A07 (SEQ ID NO:5), recurs with high frequency (75/94) and was recovered by both elution methods: competition with cT84.66 (AbE) and Factor Xa cleavage (FXE). Because this polypeptide occurred with such high frequency among the Isolates, it was regarded as a preferential binder, and the other sequences were compared against the A07 sequence to determine whether any amino acid positions in the 16-mer were conserved. A position was considered conserved if one of the other Isolates exhibited the same amino acid at the same position relative to the invariant cysteine residues; a position was considered highly conserved if two or more of the other Isolates exhibited the same amino acid at the same position relative to the invariant cysteine residues. From this analysis, the following conserved sequence (SEQ ID NO:23) was observed:

AA position:
1 2 3 4 5 6 7 8 9 10 11 12 13 14 15 16
conserved:
D W V C E X X K X Q W X C N X L In this conserved sequence (SEQ ID NO:23), the positions designated "X" showed no conservation of an A07 amino acid, the specified amino acid residues (at positions 8, 14 and 16) were conserved, and the underscored amino acid residues were highly conserved. The conserved sequence was used as a parental template in the design of an additional, secondary library (Lib2) to be screened for additional high affinity binders of CEA (see Example 7).

EXAMPLE 5

Epitope Mapping of Phage Isolates

Several of the phage Isolates were tested to determine whether binding occurred in the CEA A3 domain, by performing an ELISA with different concentrations of the anti-A3 chimeric antibody, cT84.66. Isolates G08, A07, E01, B09, F11 and D04 were tested. In each assay, H6NA3 (100 ng/well) was coated on microtiter plate wells, blocked with 2% non-fat dry milk (Carnation), and peptide displaying phage were added (5×10¹⁰/well) in the presence or absence of cT84.66. After washing, binding to H6NA3 was detected using horseradish peroxidase-labeled anti-M13 antibody. Where cT84.66 was used, it was added at 10 nM or 100 nM in separate trials. Addition of BSA was performed as a control; and assays using non-CEA-binding phage B10 (SEQ ID NO:22) and G01 (SEQ ID NO:21) were also performed as negative controls. The results of the mapping ELISA are shown in FIG. 1. These results show that in each case, the previously isolated CEA binding phage competed for the same binding site with the antibody cT84.66, which recognizes the A3 domain of CEA.

EXAMPLE 6

Binding Studies

The affinity of the peptides displayed by the four highest affinity phage Isolates (FIG. 1) were further tested in direct binding studies. 27-mer peptides including the binding loops of the G08, A07, E01 and B09 Isolates were synthesized by solid-phase synthesis. The peptides thus prepared are shown in Table 2.

TABLE 2

Amino acid sequences of CEA-binding polypeptides for binding studies

| Peptide | Synthesized Polypeptide<br>1　　　5　　　10　　　15　　　20　　　25 | SEQ ID NO: |
|---|---|---|
| P-G08 | SNWVCNLFKNQWFCNSYAPGGEGGGSK-CONH₂ | 24 |
| P-A07 | SDWVCENKKDQWTCNLLAPGGEGGGSK-CONH₂ | 25 |
| P-E01 | SNWDCMFGAEGWACSPWAPGGEGGGSK-CONH₂ | 26 |
| P-B09 | SDWVCELTTGGYVCQPLAPGGEGGGSK-CONH₂ | 27 |

As seen from Table 2, each of the peptides had an added N-terminal serine residue, replicating part of the context of the phage-display peptides. Each peptide was also provided with a C-terminal amide-functional linker useful for immobilizing peptides to various chromatographic substrates: -Ala₁₈-Pro₁₉-Gly₂₀-Gly-Glu-Gly-Gly-Gly-Ser-Lys-CONH₂ (SEQ ID NO:28). The tripeptide -Ala₁₈-Pro₁₉-Gly₂₀- replicates part of the context of the phage-displayed peptides, and the remainder of the C-terminus is a synthetic linker for immobilization. Aliquots of each peptide were fluorescently labeled using NHS-fluorescein reacted with the ε-amino side group of the C-terminal lysine.

Dissociation constants were determined using fluorescence anisotropy, through direct binding measurements and competition experiments. In direct binding assays, the concentration of the fluorescein-labeled peptide is held constant and the concentration of H6NA3 is varied. In the competition experiment, the concentration of the fluorescein-labeled peptide and the H6NA3 target are held constant and the concentration of a competitor (cT84.66, unlabeled) is varied. The change in anisotropy is fit to the appropriate equation via nonlinear regression to obtain the apparent $K_d$. The dissociation constants that describe binding of the four synthetic peptides for H6NA3 are set forth in Table 3.

TABLE 3

Dissociation constants ($K_D$) for CEA binding peptides

| Polypeptide | SEQ ID NO: | $K_D$ ($\mu$M) direct binding | $K_D$ ($\mu$M) competition |
|---|---|---|---|
| P-G08 | 24 | 1.9 | (not done) |
| P-A07 | 25 | 5.9 | 3.6 |
| P-E01 | 26 | 6.9 | 5.3 |
| P-B09 | 27 | 6.0 | 1.0 |

These experiments show that the peptides bind CEA domain A3 with dissociation constants ranging from 1 to 7 $\mu$M. From these tests, the polypeptide containing the G08 sequence appears to be the highest affinity binder isolated.

EXAMPLE 7

A Library Focused on Improved CEA Binding

A second TN10 library, focused on improved binding peptides for CEA, was constructed, using sequence and binding information obtained in the previous examples.

From the prevalence of sequences, the polypeptide A07 (SEQ ID NO:5) appeared to be the best binder. Using this sequence as a secondary parental domain or template, 5 amino acid positions within the A07 sequence were variegated. Five oligonucleotides were constructed that used A07 as the parental sequence and allowed five positions at a time to vary through all sequences that exclude cysteine. The oligonucleotide sequences thus encoded peptides having the designed sequences Var1 through Var5 shown in Table 4, below. After observing that the peptide G08 had the lowest $K_D$, additional variegated oligonucleotides coding for peptides based on the parental sequence of G08 were designed and added to the focused library. The oligonucleotide sequences that encoded G08-based peptides having the designed sequences Var6 and Var7 shown in Table 4, below.

TABLE 4

Designed Polypeptides for Expression in Display Library "Lib2"
X = any amino acid residue except Cys

| Encoded Peptides | Amino Acid Sequence | SEQ ID NO: |
| --- | --- | --- |
| A07 (parental) | DWVCENKKDQWTCNLL | 5 |
| Var1 | XXXCXXKKDQWTCNLL | 29 |
| Var2 | DWVCXXXXXQWTCNLL | 30 |
| Var3 | DWVCENKXXXXXCNLL | 31 |
| Var4 | DWVCENKKDQXXCXXX | 32 |
| Var5 | DWVCEXXKXQWXCNXL | 33 |
| G08 (parental) | NWVCNLFKNQWFCNSY | 4 |
| Var6 | NWVCXXXKXQWXCNSY | 34 |
| Var7 | XWXCNLFKNQWFCXXX | 35 |

The oligonucleotides encoding the peptides Var1 through Var7 were mixed in equal proportion and a secondary library ("Lib2"), allowing about $1.7 \times 10^7$ different sequences, was constructed. More than $5 \times 10^8$ transformants were obtained, so that all allowed sequences should be present.

EXAMPLE 8

Panning Lib2 and Isolates from Lib2

Lib2 was panned through 3 rounds using lower amounts of target and following two separate wash protocols: Wash protocol 1 (W1) was identical to the screening protocol utilized in example 2 (i.e., 10 washes with PBS/0.1% TWEEN-20, a non-ionic detergent), Wash protocol 2 (W2) comprised 5 washes in the PBS/0.1% TWEEN buffer, a one-hour soak in the same buffer, followed by 5 more washes. Bound phage were eluded following Factor X cleavage procedures and the two screened samples (W1 and W2) were propagated separately overnight (Round 1).

In the second round of screening the W1 sample, the target concentration was reduced to one third of the target concentration used in round 1; the second round of screening W2 was identical to round 1. The Wash protocol for W1 and W2 was the same as performed for each in round 1. Bound phage were recovered by elution under two conditions: first, by competitive binding with cT84.66 (added at 333 nM), followed by a Factor Xa cleavage elution (as in Example 2). Phage fractions of the competitive antibody elution (W1AbE and W2AbE) and the Factor X elution (W1FXE and W2FXE) were recovered and propagated separately overnight (Round 2).

The third round selection consisted of wash protocols identical to round 2 for each of the two wash protocols (W1 and W2), followed by either antibody elution (for W1AbE and W2 AbE) or Factor X elution (for W1FXE and W2FXE) and propagation (separately) overnight (Round 3).

An increase in the elution titer was observed following round 2 but leveled out at round 3, indicating that selection of phage that had an affinity for NA3 was occurring initially but could not increase due either to the high concentration of multiple high affinity binders in the library population or (more likely) equilibration to the concentration of target on the plate.

After the third round, 96 Isolates from each of the four treatment groups (W1AbE, W1FXE, W2AbE, and W2FXE) were tested by ELISA for binding to NA3. Seventy-two Isolates were ELISA positive and were sequenced. There were 71 distinct sequences, indicating that further screening may be needed to identify the very best sequences. The sequences are shown in Table 5, below. The seventy-one CEA binders of the Lib2 screen define a preferred family of binding moieties having a general formula:

$$X_1\text{-Trp-}X_2\text{-Cys-}X_3\text{-}X_4\text{-}X_5\text{-} \qquad \text{(SEQ ID NO:36)}$$
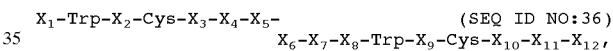

wherein:

$X_1$ is Asp, Asn, Ala, or Ile, with Asp most preferred;

$X_2$ is Val, Ile, Met, Tyr, Phe, Pro, or Asp, with Val most preferred;

$X_3$ is Asn, Glu, or Asp, with Asn and Glu most preferred;

$X_4$ is Leu, Phe, Tyr, Trp, Val, Met, Ile, or Asn, with Leu most preferred;

$X_5$ is Phe, Leu, Asp, Glu, Ala, Ile, Lys, Asn, Ser, Val, Trp, or Tyr, with Phe most preferred;

$X_6$ is Lys, Phe, Asp, Gly, Leu, Asn, or Trp, with Lys most preferred;

$X_7$ is Asn, Pro, Phe, Gly, Asp, Ala, Ser, Glu, Gln, or Trp, with Asn most preferred;

$X_8$ is Gln, or Lys, with Gln most preferred;

$X_9$ is Phe, Thr, Met, Ser, Ala, Asn, Val, His, Ile, Pro, Trp, or Tyr, with Phe most preferred;

$X_{10}$ is Asn, Asp, Glu, Pro, Gln, or Ser, with Asn and Asp most preferred;

$X_{11}$ is Val, Leu, Ile, Pro, Ala, Gln, Ser, Met, Glu, Thr, Lys, or Trp, with Val and Leu most preferred; and $X_{12}$ is Leu, Met, Val, Tyr, Ala, Ile, Trp, His, Pro, Gln, Glu, Phe, Lys, or Arg, with Leu most preferred.

TABLE 5

Sequenced CEA Binder Peptides from Lib2 Directed Library

| Peptide | \multicolumn{16}{c}{Amino Acid Position} | SEQ ID NO: |
|---|---|---|---|---|---|---|---|---|---|---|---|---|---|---|---|---|---|

| Peptide | 1 | 2 | 3 | 4 | 5 | 6 | 7 | 8 | 9 | 10 | 11 | 12 | 13 | 14 | 15 | 16 | SEQ ID NO: |
|---|---|---|---|---|---|---|---|---|---|---|---|---|---|---|---|---|---|
| 304A-11-A02 | D | W | M | C | N | L | F | K | N | Q | W | F | C | D | L | M | 37 |
| 304A-11-F02 | D | W | V | C | N | L | F | K | N | Q | W | F | C | D | L | M | 38 |
| 304A-11-E04 | D | W | I | C | N | L | F | K | N | Q | W | F | C | D | Q | M | 39 |
| 304A-11-D06 | N | W | I | C | N | L | F | K | N | Q | W | F | C | D | Q | E | 40 |
| 304A-11-B07 | D | W | I | C | N | L | F | K | N | Q | W | F | C | Q | V | K | 41 |
| 304A-11-H07 | D | W | V | C | N | L | F | K | N | Q | W | F | C | D | V | M | 42 |
| 304A-11-C09 | D | W | M | C | N | L | F | K | N | Q | W | F | C | D | Q | I | 43 |
| 304A-11-H10 | I | W | D | C | N | L | F | K | N | Q | W | F | C | P | A | P | 44 |
| 304A-11-A11 | D | W | I | C | N | L | F | K | N | Q | W | F | C | D | I | R | 45 |
| 304A-11-G11 | D | W | M | C | N | L | F | K | N | Q | W | F | C | D | V | V | 46 |
| 304A-11-C02 | D | W | M | C | N | L | F | K | N | Q | W | F | C | D | V | V | 46 |
| 304A-11-H11 | D | W | I | C | N | L | F | K | N | Q | W | F | C | D | A | I | 47 |
| 304A-11-A12 | D | W | I | C | N | L | F | K | N | Q | W | F | C | D | M | A | 48 |
| 304A-12-E01 | D | W | V | C | E | F | L | K | M | Q | W | A | C | N | V | L | 49 |
| 304A-12-A02 | D | W | V | C | N | L | F | K | N | Q | W | F | C | N | V | M | 50 |
| 304A-12-H02 | A | W | P | C | N | L | F | K | N | Q | W | F | C | P | P | Q | 51 |
| 304A-12-A05 | D | W | V | C | N | L | F | K | N | Q | W | F | C | D | V | L | 52 |
| 304A-12-C05 | D | W | V | C | N | L | F | K | N | Q | W | F | C | D | K | W | 53 |
| 304A-12-F05 | D | W | V | C | E | W | L | K | M | Q | W | A | C | N | M | L | 54 |
| 304A-12-C09 | D | W | V | C | D | F | F | F | N | Q | W | T | C | N | L | L | 55 |
| 304A-12-D09 | D | W | V | C | E | M | F | K | A | Q | W | F | C | N | A | L | 56 |
| 304A-12-E09 | D | W | I | C | N | L | F | K | N | Q | W | F | C | D | A | W | 57 |
| 304A-12-G12 | D | W | V | C | N | L | F | K | N | Q | W | F | C | D | V | W | 58 |
| 304A-12-H12 | D | W | V | C | E | Y | F | K | N | Q | W | F | C | N | V | L | 59 |
| 304A-13-C01 | D | W | V | C | E | I | D | K | G | Q | W | T | C | N | P | L | 60 |
| 304A-13-B02 | D | W | V | C | N | L | F | K | N | Q | W | F | C | N | P | F | 61 |
| 304A-13-A03 | D | W | V | C | N | L | F | K | N | Q | W | F | C | D | V | Q | 62 |
| 304A-13-A12 | D | W | I | C | N | L | F | K | N | Q | W | F | C | N | E | A | 108 |
| 304A-13-E04 | D | W | V | C | N | L | F | F | G | Q | W | T | C | N | L | L | 63 |
| 304A-13-F05 | D | W | I | C | N | L | F | K | N | Q | W | F | C | E | A | H | 64 |
| 304A-13-H07 | D | W | V | C | E | L | V | K | A | Q | W | Y | C | N | I | L | 65 |
| 304A-13-G08 | N | W | V | C | N | L | F | K | N | Q | W | F | C | D | T | V | 66 |
| 304A-13-C09 | D | W | V | C | E | F | Y | K | S | Q | W | N | C | N | I | L | 67 |
| 304A-13-A10 | D | W | V | C | E | W | F | K | P | Q | W | F | C | N | P | L | 68 |
| 304A-13-C10 | D | W | Y | C | N | L | F | K | N | Q | W | F | C | D | V | L | 69 |
| 304A-13-A11 | D | W | V | C | E | Y | N | D | E | Q | W | T | C | N | L | L | 70 |
| 304A-13-A12 | D | W | I | C | N | L | F | K | N | Q | W | F | C | N | E | A | 71 |
| 304A-14-C01 | D | W | V | C | N | W | E | L | F | Q | W | T | C | N | L | L | 72 |
| 304A-14-A02 | D | W | V | C | N | L | F | K | N | Q | W | F | C | D | Q | V | 73 |
| 304A-14-B02 | D | W | V | C | N | L | F | K | N | Q | W | F | C | D | V | P | 74 |
| 304A-14-G02 | D | W | V | C | E | F | F | K | Q | Q | W | F | C | N | V | L | 75 |
| 304A-14-H02 | D | W | V | C | E | F | F | K | D | Q | W | S | C | N | V | L | 76 |
| 304A-14-A03 | D | W | V | C | N | L | F | K | N | Q | W | F | C | D | S | L | 77 |
| 304A-14-H03 | D | W | V | C | E | F | M | K | H | Q | W | F | C | N | P | L | 78 |
| 304A-14-B06 | D | W | I | C | N | L | F | K | N | Q | W | F | C | Q | A | V | 79 |
| 304A-14-H08 | D | W | V | C | E | F | I | K | N | Q | W | M | C | N | V | L | 80 |
| 304A-14-A10 | D | W | V | C | N | L | F | K | N | Q | W | F | C | D | A | L | 81 |
| 304A-14-F10 | D | W | V | C | E | Y | E | K | D | Q | W | S | C | N | I | L | 82 |
| 304A-14-A12 | D | W | V | C | N | L | F | K | N | Q | W | F | C | D | T | L | 83 |
| 304A-15-E01 | D | W | Y | C | N | L | F | K | N | Q | W | F | C | D | V | Y | 84 |
| 304A-15-G01 | D | W | F | C | N | L | F | K | N | Q | W | F | C | S | P | I | 85 |
| 304A-15-A02 | D | W | V | C | E | F | F | K | K | Q | W | F | C | N | L | L | 86 |
| 304A-15-F02 | N | W | V | C | D | V | L | K | W | Q | W | P | C | N | S | Y | 87 |
| 304A-15-G02 | D | W | V | C | E | Y | D | K | G | Q | W | H | C | N | I | L | 88 |
| 304A-15-C03 | D | W | I | C | N | L | F | K | N | Q | W | F | C | Q | Q | H | 89 |
| 304A-15-H03 | D | W | V | C | N | W | L | W | G | Q | W | T | C | N | L | L | 90 |
| 304A-15-C04 | D | W | V | C | E | M | F | K | K | Q | W | V | C | N | P | L | 91 |
| 304A-15-E04 | D | W | I | C | N | L | F | K | N | Q | W | F | C | G | P | L | 92 |
| 304A-15-A05 | D | W | V | C | E | V | I | K | D | Q | W | V | C | N | P | L | 93 |
| 304A-15-E05 | D | W | V | C | E | N | K | N | F | K | W | F | C | N | L | L | 94 |
| 304A-15-G06 | D | W | V | C | E | Y | A | K | N | Q | W | N | C | N | P | L | 95 |
| 304A-15-A07 | N | W | V | C | N | L | F | K | N | Q | W | F | C | E | W | A | 96 |
| 304A-15-B07 | N | W | V | C | D | Y | W | K | P | Q | W | F | C | N | S | Y | 97 |
| 304A-15-E07 | D | W | Y | C | N | L | F | K | N | Q | W | F | C | D | L | V | 98 |
| 304A-15-G07 | N | W | V | C | N | L | F | K | N | Q | W | F | C | D | E | M | 99 |
| 304A-15-H07 | D | W | V | C | E | L | F | K | P | Q | W | F | C | N | I | L | 100 |
| 304A-15-B08 | D | W | V | C | E | W | S | K | M | Q | W | S | C | N | A | L | 101 |
| 304A-15-F08 | D | W | V | C | D | Y | K | F | F | Q | W | T | C | N | L | L | 102 |
| 304A-15-G08 | N | W | V | C | E | W | L | K | P | Q | W | W | C | N | S | Y | 103 |
| 304A-15-H09 | D | W | V | C | E | F | F | K | P | Q | W | M | C | N | I | L | 104 |
| 304A-15-G11 | D | W | V | C | E | Y | F | K | S | Q | W | M | C | N | M | L | 105 |

TABLE 5-continued

Sequenced CEA Binder Peptides from Lib2 Directed Library

| Peptide | Amino Acid Position | | | | | | | | | | | | | | | | SEQ ID NO: |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | |
| 304A-15-F12 | D | W | V | C | E | F | F | G | M | Q | W | T | C | N | L | L | 106 |
| 304A-15-H12 | D | W | V | C | E | Y | A | K | F | Q | W | I | C | N | I | L | 107 |

Figure 2:
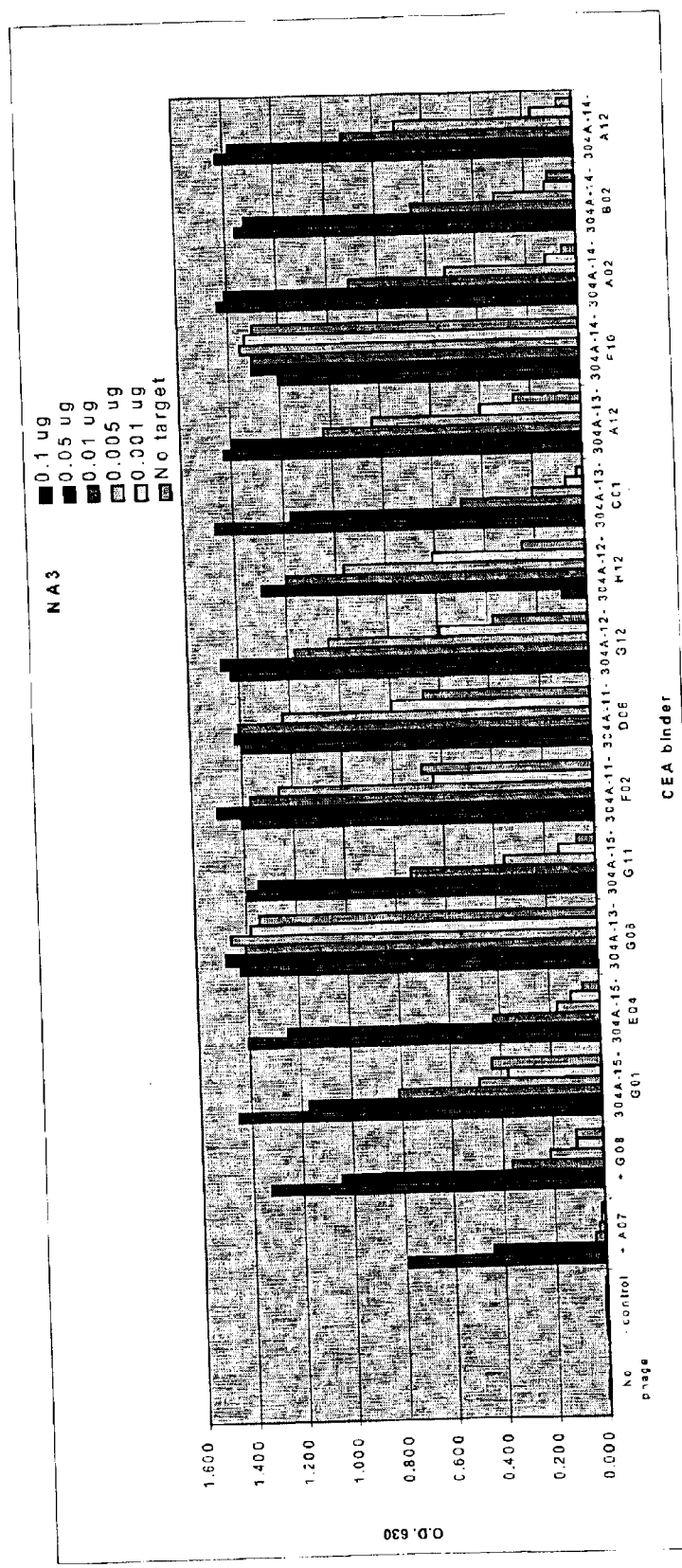
FIG. 2 shows ELISA scores for TN10/9 Isolates A07 and G08, in comparison to 14 different Lib2 Isolates. The first bar for each sample represents wells each having 100 ng CEA. Successive bars represent 50 ng, 10 ng, 5 ng, 1 ng, and 0 ng CEA per well.

Several Isolates gave especially strong ELISA signals and these were tested further. FIG. 2 shows the binding profile of 14 different CEA binder Isolates (in comparison to the earlier isolated CEA binders A07 and G08) to varying concentrations of NA3. For example, the binding of G08 and A07 drops off very quickly as the amount of NA3 drops below 50 ng per well. The binding of 304A-12-H12 and 304A-14-A12 do not drop off so quickly. The 304A-14-B02 and 304A-15-E04 show binding that is at least as good as G08 and A07.

Figure 3:
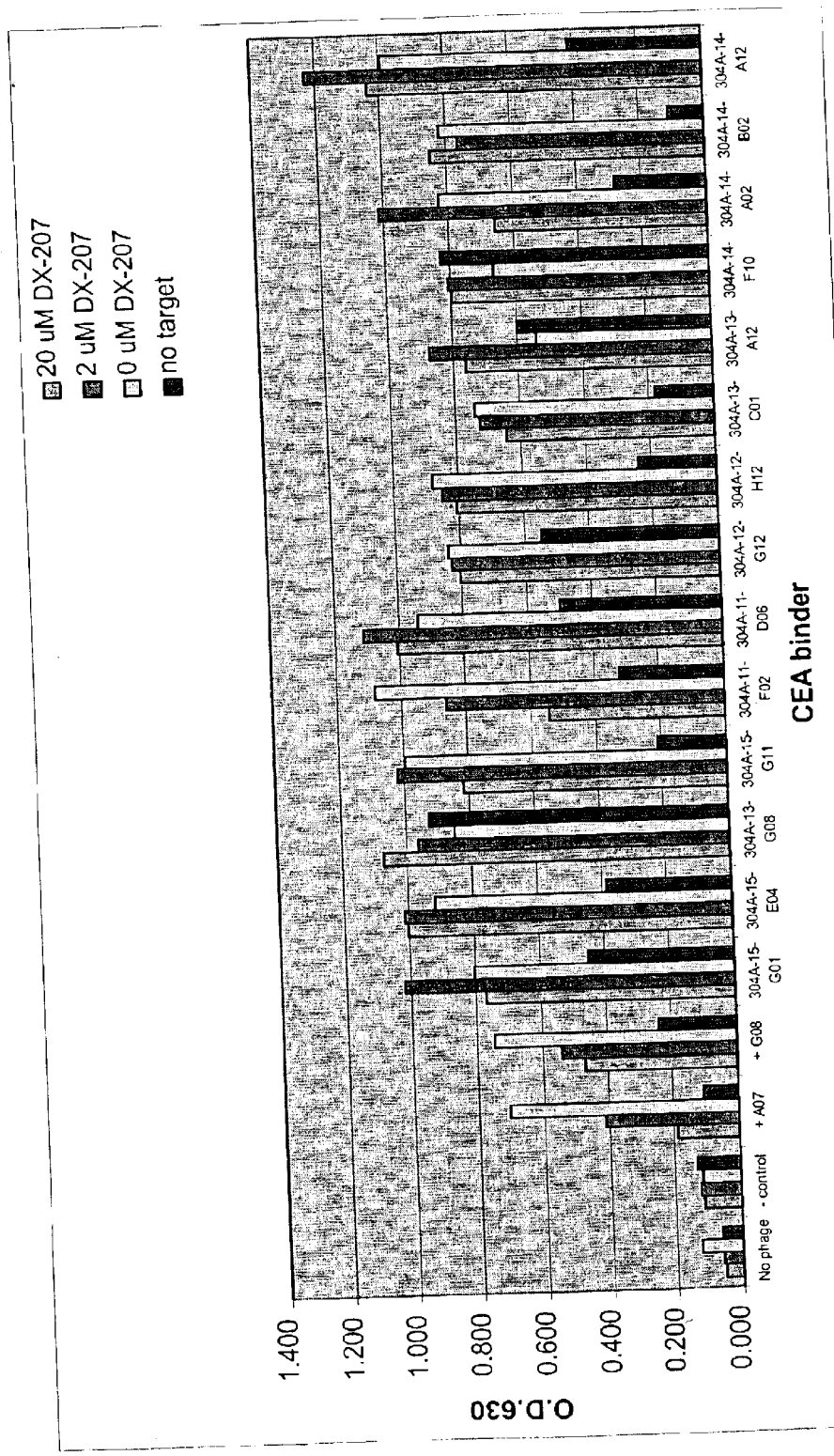
FIG. 3 shows competition ELISA scores for TN10/9 Isolates A07 and G08, in comparison to 14 different Lib2 Isolates. The amount of CEA in each well was constant at 0.1 µg/well. A soluble peptide having the CEA binder sequence of the G08 Isolate (SEQ ID NO:4), DX207, was added as an inhibitor to CEA binding. The first bar for each sample represents 20 µM of the G08 CEA binder. Successive bars represent 2 µM, 0 M, and no target.

FIG. 3 shows the binding profile of 14 different CEA binder Isolates to NA3 in a competition assay varying concentrations of a soluble peptide having the G08 sequence (inhibitor peptide, designated DX207). These data indicate the isolates from the Lib2 screen generally exhibit higher affinity for CEA domain A3 than do G08 or A07.

EXAMPLE 9

Lib2 Isolate Binding Studies

The affinity of select peptides displayed by phage Isolates from the Lib2 screening were further tested in direct binding studies (as in Example 6). Peptides including the binding domain of the CEA binder Isolates were synthesized by solid-phase synthesis.

In addition, a peptide of unique sequence was synthesized de novo based upon a "hybridization" construct of the sequence of Isolates 304A-12-H12 and 304A-14-A12, which differed from each other in two separate amino acid pairs. Table 6 illustrates the construct of this "Hybrid H12/A12" from the two "parental" sequences.

TABLE 6

Amino acid sequences of CEA-binding polypeptides for binding studies

| Isolate | CEA Binding Domain | | | | SEQ ID NO: |
|---|---|---|---|---|---|
| | 1 | 5 | 10 | 15 | |
| 304A-12-H12 | DWVCEYFKNQWFCNVL | | | | 59 |
| 304A-14-A12 | DWVCNLFKNQWFCDTL | | | | 83 |
| Hybrid H12/A12 | DWVCEYFKNQWFCDTL | | | | 109 |

Aliquots of each peptide were fluorescently labeled using NHS-fluorescein reacted with the ε-amino side group of the C-terminal lysine.

Dissociation constants were determined using fluorescence anisotropy, through direct binding measurements (see Example 6). The dissociation constants that describe binding of the synthetic peptides for H6NA3 are set forth in Table 7.

TABLE 7

Dissociation constants ($K_D$) for CEA binding peptides

| Isolate | SEQ ID NO: | $K_D$ ($\mu$M) direct binding |
|---|---|---|
| 304A-12-H12 | 59 | 0.24 ± 0.03 |
| 304A-14-A12 | 83 | 0.64 ± 0.1 |
| Hybrid H12/A12 | 109 | 2.8 ± 1.8 |

These experiments demonstrate that the 304A-12-H12 CEA binder (also designated DX306) showed an 8 fold increase in affinity compared to the Isolate G08 peptide (from Table 3). The CEA binder from Isolate 304A-14-A12, also showed a several fold increase in affinity. The synthetic peptide, Hybrid H12/A12, exhibiting CEA binding characteristics comparable to the Isolates obtained from the initial library screen, did not show the dramatically improved binding characteristics exhibited by the binders obtained from the Lib 2 screen. These results support the view that additional screening of a "pre-selected", biased library (e.g., Lib2) produces "improved" binders of higher affinity than those isolated from a "naïve" library.

EXAMPLE 10

High Stringency CEA Binder Screen of Naive and Pre-Selected Libraries

Because the Lib2 screen produced CEA binders of higher affinity than those isolated from the non-biased library, and because there was no apparent sequence convergence of the Lib2 screen Isolates, panning of the naïve library and the pre-selected library (i.e., Lib2) under high stringency wash conditions was performed to produce CEA binders of even higher affinity.

A high stringency CEA binder screen was preformed on three libraries separately. The amplified elutions produced from the third round of CEA biased library screen (Example 8) were combined to form two "pooled libraries": a pooled antibody eluted library, "pAb" (from W1AbE and W2AbE), and a pooled Factor X eluted library, "pFX" (from W1FXE and W2FXE). The third, naïve library was the original TN10/9 library of Example 2 (hereinafter denoted with the letters "CEA").

Each of the three libraries was screened following the same binding (0.1 μg NA3 target) and wash protocol. Five washes (PBS/0.1% TWEEN-20, a non-ionic detergent) were performed at 30 minute intervals with soaking in between followed by an additional four washes, aliquots from each of which were saved. Wash 1 (producing aliquots W1pAB, W1pFX, and W1CEA) was a 1 hour competitive elution using 10 uM DX306 in PBS/0.1% TWEEN. Wash 2 (producing aliquots W2pAB, W2pFX, and W2CEA) was identical to Wash 1. Wash 3 (producing aliquots W3pAB, W3pFX, and W3CEA) was an overnight (18 hour) elution in the same buffer. Wash 4 (producing aliquots W4pAB, W4pFX, and W4CEA) was a Factor X elution. W3CEA and W4CEA were propagated separately overnight and passed through a second round screen identical to the first round (producing W3CEA$_{R2}$, and W4CEA$_{R2}$ Isolates).

As expected, an increase in the elution titer was observed in the two pre-selected, pooled libraries compared to the naïve library. Also, the naïve library showed an increase in titer in the second round for the 18 hour wash but not the Factor X elution. Elution titer results of these screens (data not shown) indicate that selection of phage that had an affinity for NA3 was occurring in all the pools except the Factor X wash of the naïve library; perhaps due to the relatively small quantity of high affinity binders in the initial library being washed from the target during the 18 hour wash, whereas the pre-selected pools started with high titers of tight binders with a greater probability of still being present at the last (Factor X cleavage) elution.

Ninety-eight (98) Isolates from each of eight elution aliquots (W3pAb, W3pFX, W4pAb, W4pFX, W3CEA$_{R1}$, W4CEA$_{R1}$, W3CEA$_{R2}$ and W4CEA$_{R2}$) were randomly selected and tested by ELISA for binding to NA3. Table 8 discloses the amino acid sequence of CEA binders isolated from the high stringency screen of the naïve library. Table 9 discloses the amino acid sequence of CEA binders isolated from the high stringency screen of the pre-selected libraries.

The discovery of these high stringency CEA binders further define a CEA binding domain having a general formula:

(SEQ ID NO:110)
Cys-X$_4$-X$_5$-X$_6$-X$_7$-X$_8$-X$_9$-X$_{10}$-X$_{11}$-Cys, wherein:

X$_4$ is Asn, Glu, Asp, or Met;

X$_5$ is Leu, Phe, Tyr, Trp, Val, Met, Ile, or Asn;

X$_6$ is Phe, Leu, Asp, Glu, Ala, Ile, Lys, Asn, Ser, Val, Trp, Tyr, Gly, or Thr;

X$_7$ is Lys, Phe, Asp, Gly, Leu, Asn, Trp, Ala, Gln, or Thr;

X$_8$ is Asn, Pro, Phe, Gly, Asp, Ala, Ser, Glu, Gln, Trp, His, Arg, Met, Val, or Leu;

X$_9$ is Gln, Lys, Leu, or Gly;

X$_{10}$ is Trp, Ala, or Tyr; and

X$_{11}$ is Phe, Thr, Met, Ser, Ala, Asn, Val, His, Ile, Pro, Trp, Tyr, Gly, Leu, or Glu.

More particularly, these CEA binders define a preferred family of binding moieties having a general formula:

X$_1$-X$_2$-X$_3$-Cys-X$_4$-X$_5$- (SEQ ID NO: 111)
X$_6$-X$_7$-X$_8$-X$_9$-X$_{10}$-X$_{11}$-Cys-X$_{12}$-X$_{13}$-
X$_{14}$,
wherein:

X$_1$ is Asp, Asn, Ala, or Ile;

X$_2$ is Trp;

X$_3$ is Val, Ile, Met, Tyr, Phe, Pro, or Asp;

X$_4$ is Asn, Glu, Asp, or Met;

X$_5$ is Leu, Phe, Tyr, Trp, Val, Met, Ile, or Asn;

X$_6$ is Phe, Leu, Asp, Glu, Ala, Ile, Lys, Asn, Ser, Val, Trp, Tyr, Gly, or Thr;

X$_7$ is Lys, Phe, Asp, Gly, Leu, Asn, Trp, Ala, Gln, or Thr;

X$_8$ is Asn, Pro, Phe, Gly, Asp, Ala, Ser, Glu, Gln, Trp, His, Arg, Met, Val, or Leu;

X$_9$ is Gln, Lys, Leu, or Gly;

X$_{10}$ is Trp, Ala, or Tyr;

X$_{11}$ is Phe, Thr, Met, Set, Ala, Asn, Val, His, Ile, Pro, Trp, Tyr, Gly, Leu, or Glu;

X$_{12}$ is Asn, Asp, Glu, Pro, Gln, Set, Phe, or Val;

X$_{13}$ is Val, Leu, Ile, Pro, Ala, Gln, Ser, Met, Glu, Thr, Lys, Trp, or Arg; and X$_{14}$ is Leu, Met, Val, Tyr, Ala, Ile, Trp, His, Pro, Gln, Glu, Phe, Lys, Arg, or Ser.

TABLE 8

Sequenced CEA Binder Peptides from Naïve Library

| Peptide | Amino Acid Position | | | | | | | | | | | | | | | | SEQ ID NO: |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | |
| FX-G08 | N | W | V | C | N | L | F | K | N | Q | W | F | C | N | S | Y | 4 |
| 304A-12-H12 | D | W | V | C | E | Y | F | K | N | Q | W | F | C | N | V | L | 59 |
| Consensus | D | W | V | C | E | W | L | K | M | Q | W | A | C | N | I | L | 112 |
| 315A-19-A10 | D | W | V | C | E | Y | V | K | S | Q | W | S | C | N | P | L | 113 |
| 315A-16-C04 | D | W | V | C | E | F | S | K | V | Q | W | Y | C | N | P | L | 114 |
| 315A-22-B06 | D | W | V | C | E | W | F | K | P | Q | W | I | C | N | L | L | 115 |
| 315A-22-D06 | D | W | V | C | E | I | V | K | N | Q | W | H | C | N | V | L | 116 |
| 315A-22-E12 | D | W | V | C | E | W | G | K | N | Q | W | T | C | N | P | L | 117 |
| 315A-23-F10 | D | W | V | C | E | F | E | K | G | Q | W | T | C | N | V | L | 118 |

TABLE 9

Sequenced CEA Binder Peptides from Pre-selected Libraries

| Peptide | \multicolumn{16}{c}{Amino Acid Position} | SEQ ID NO. |
|---|---|---|---|---|---|---|---|---|---|---|---|---|---|---|---|---|---|

| Peptide | 1 | 2 | 3 | 4 | 5 | 6 | 7 | 8 | 9 | 10 | 11 | 12 | 13 | 14 | 15 | 16 | SEQ ID NO. |
|---|---|---|---|---|---|---|---|---|---|---|---|---|---|---|---|---|---|
| FX-G08 | N | W | V | C | N | L | F | K | N | Q | W | F | C | N | S | Y | 4 |
| 304A-12-H12 | D | W | V | C | E | Y | F | K | N | Q | W | F | C | N | V | L | 59 |
| Consensus | D | W | V | C | E | W | L | K | M | Q | W | A | C | N | I | L | 112 |
| 315A-20-A06 | D | W | V | C | N | L | F | K | N | Q | W | F | C | N | V | W | 119 |
| 315A-20-A12 | D | W | V | C | N | L | F | K | N | Q | W | F | C | D | V | H | 120 |
| 315A-20-B07 | D | W | I | C | N | L | F | K | N | Q | W | F | C | D | I | R | 121 |
| 315A-20-B08 | D | W | V | C | E | W | L | K | M | Q | W | A | C | N | I | L | 122 |
| 315A-20-B09 | D | W | V | C | E | F | I | K | D | Q | W | Y | C | D | L | A | 123 |
| 315A-20-C09 | D | W | V | C | N | L | F | K | N | Q | W | F | C | D | V | V | 124 |
| 315A-20-C10 | D | W | V | C | E | W | L | K | M | Q | W | A | C | N | V | L | 125 |
| 315A-20-D06 | D | W | V | C | E | W | L | K | N | Q | W | W | C | N | V | L | 126 |
| 315A-20-D07 | D | W | V | C | E | L | L | K | N | Q | W | F | C | N | V | L | 127 |
| 315A-20-F11 | D | W | V | C | N | L | F | K | N | Q | W | F | C | N | V | L | 128 |
| 315A-20-G10 | D | W | V | C | N | L | F | K | N | Q | W | F | C | D | V | M | 129 |
| 315A-20-G12 | D | W | V | C | E | W | F | K | A | Q | W | F | C | N | M | L | 130 |
| 315A-20-H06 | D | W | I | C | N | L | F | K | N | Q | W | F | C | D | Q | L | 131 |
| 315A-20-H07 | D | W | M | C | N | L | F | K | N | Q | W | F | C | D | V | Q | 132 |
| 315A-20-H09 | D | W | V | C | E | F | D | K | G | Q | W | N | C | N | I | L | 133 |
| 315A-21-A06 | D | W | I | C | N | L | F | K | N | Q | W | F | C | D | A | W | 134 |
| 315A-21-A12 | D | W | V | C | E | F | D | K | L | Q | W | V | C | N | V | L | 135 |
| 315A-21-E07 | D | W | V | C | N | L | F | K | N | Q | W | F | C | D | Q | M | 136 |
| 315A-21-F07 | D | W | V | C | E | F | F | K | S | Q | W | Y | C | N | I | L | 137 |
| 315A-21-H09 | D | W | V | C | E | W | L | K | M | Q | W | A | C | N | M | L | 138 |
| 315A-17-A06 | D | W | V | C | E | Y | F | K | N | Q | W | L | C | N | I | L | 139 |
| 315A-17-B01 | D | W | V | C | E | W | L | K | M | Q | W | A | C | N | I | L | 140 |
| 315A-17-B02 | D | W | V | C | E | W | L | K | M | Q | W | F | C | N | A | L | 141 |
| 315A-17-B05 | D | W | V | C | E | W | L | K | M | Q | W | A | C | N | V | L | 142 |
| 315A-17-B06 | D | W | V | C | E | W | L | K | M | Q | W | A | C | N | M | L | 143 |
| 315A-17-B12 | D | W | V | C | E | W | L | K | P | Q | W | Y | C | N | S | L | 144 |
| 315A-17-E12 | D | W | V | C | N | L | F | K | N | Q | W | F | C | D | L | S | 145 |
| 315A-17-F04 | D | W | V | C | E | W | L | K | S | Q | W | F | C | N | S | L | 146 |
| 315A-17-G08 | D | W | V | C | E | F | I | K | S | Q | W | F | C | N | V | L | 147 |
| 315A-18-B02 | D | W | V | C | E | W | L | K | H | Q | W | F | C | N | A | L | 148 |
| 315A-18-E01 | D | W | V | C | E | I | V | K | N | Q | W | I | C | N | P | L | 149 |
| 315A-18-E02 | D | W | V | C | E | F | F | K | D | Q | W | F | C | N | I | L | 150 |
| 315A-18-E04 | D | W | V | C | E | F | L | K | M | Q | W | A | C | N | V | L | 151 |

Figure 4:
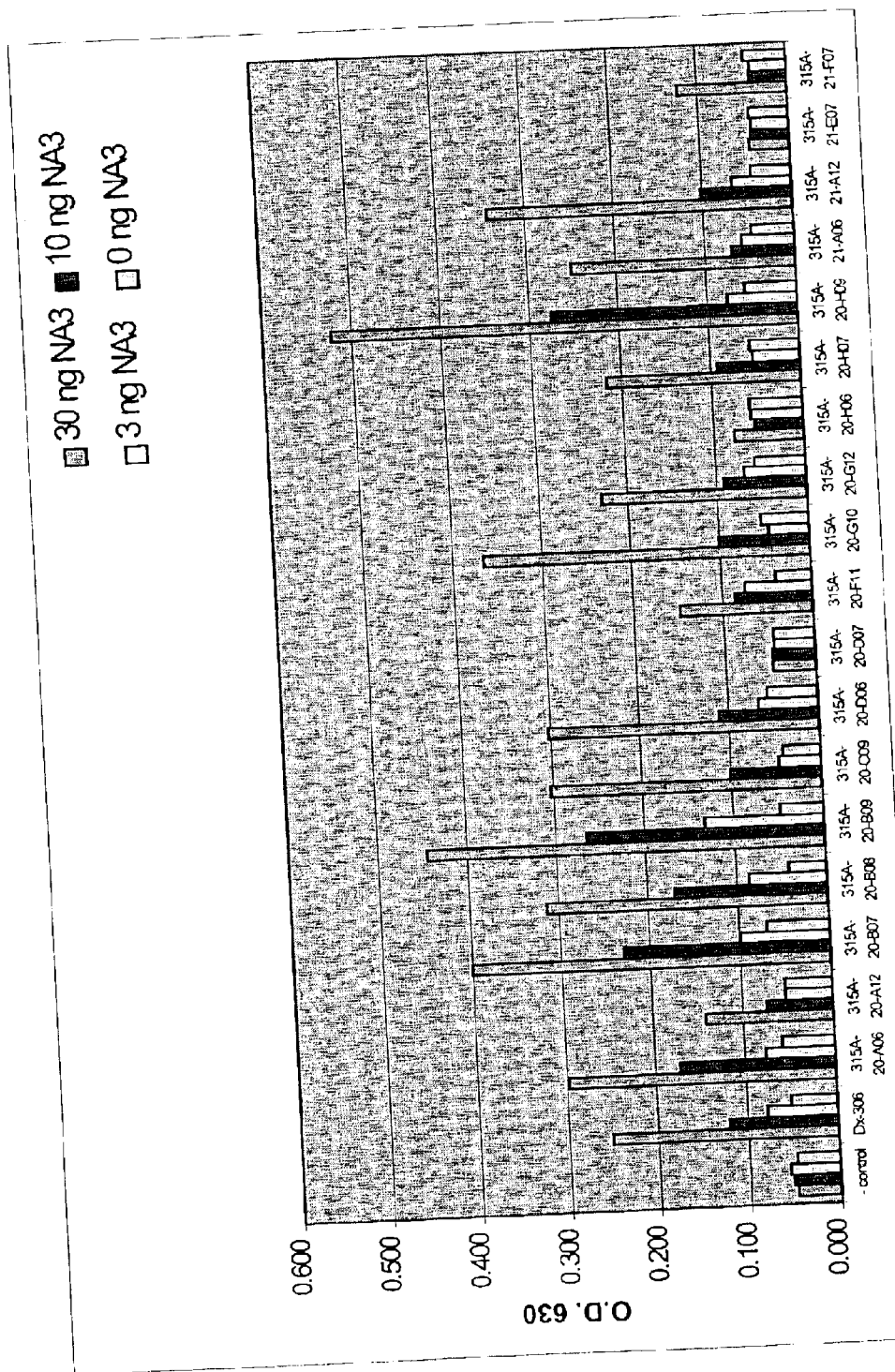
FIG. 4 shows ELISA scores for 18 different CEA-binding phage isolated following a high stringency, 18-hour elution of Lib2 (designated W3) to varying concentrations of NA3 as compared to peptide DX306, having the amino acid sequence of Isolate 304A-12-H12 (SEQ ID NO:59). The first bar for each sample represents wells each having 30 ng NA3. Successive bars represent 10 ng, 3 ng, and 0 ng NA3 per well.
Figure 5:
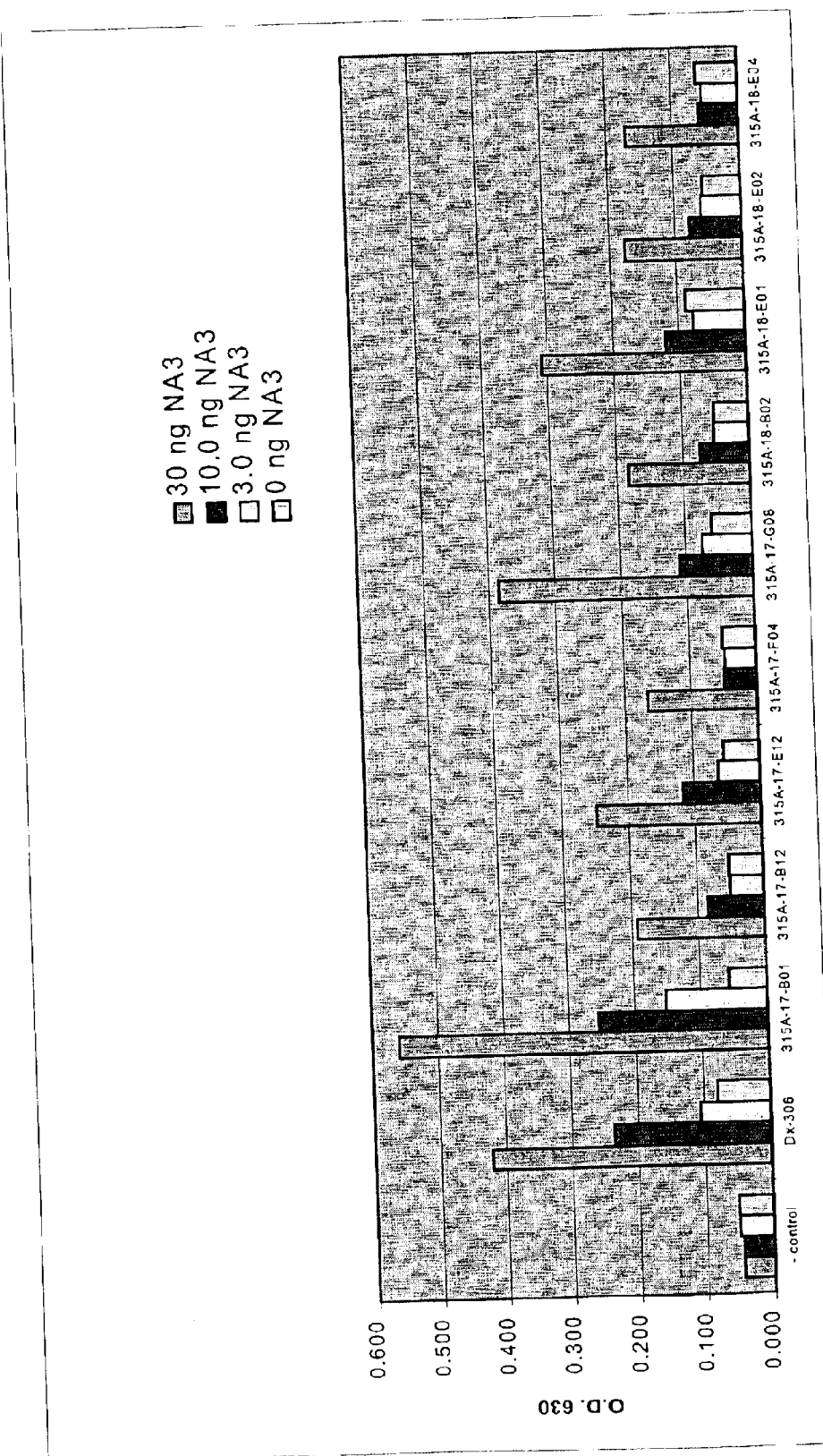
FIG. 5 shows ELISA scores for 18 different CEA-binding phage Isolated following a high stringency, Factor X elution of Lib2 (designated W4) to varying concentrations of NA3 as compared to peptide DX306, having the amino acid sequence of Isolate 304A-12-H12 (SEQ ID NO:59). The first bar for each sample represents wells each having 30 ng NA3. Successive bars represent 10 ng, 3 ng, and 0 ng NA3 per well.

Several Isolates gave especially strong ELISA signals and these were tested further. FIG. 4 shows the binding profile of 18 different CEA binders isolated from the 18-hour elution (W3) to varying concentrations of NA3. FIG. 5 shows the binding profile of nine (9) different CEA binders isolated from the Factor X elution (W4) to varying concentrations of NA3. Isolate 304A-12-H12 (designated DX306) was assayed in parallel as a basis for comparison.

Figure 6A:
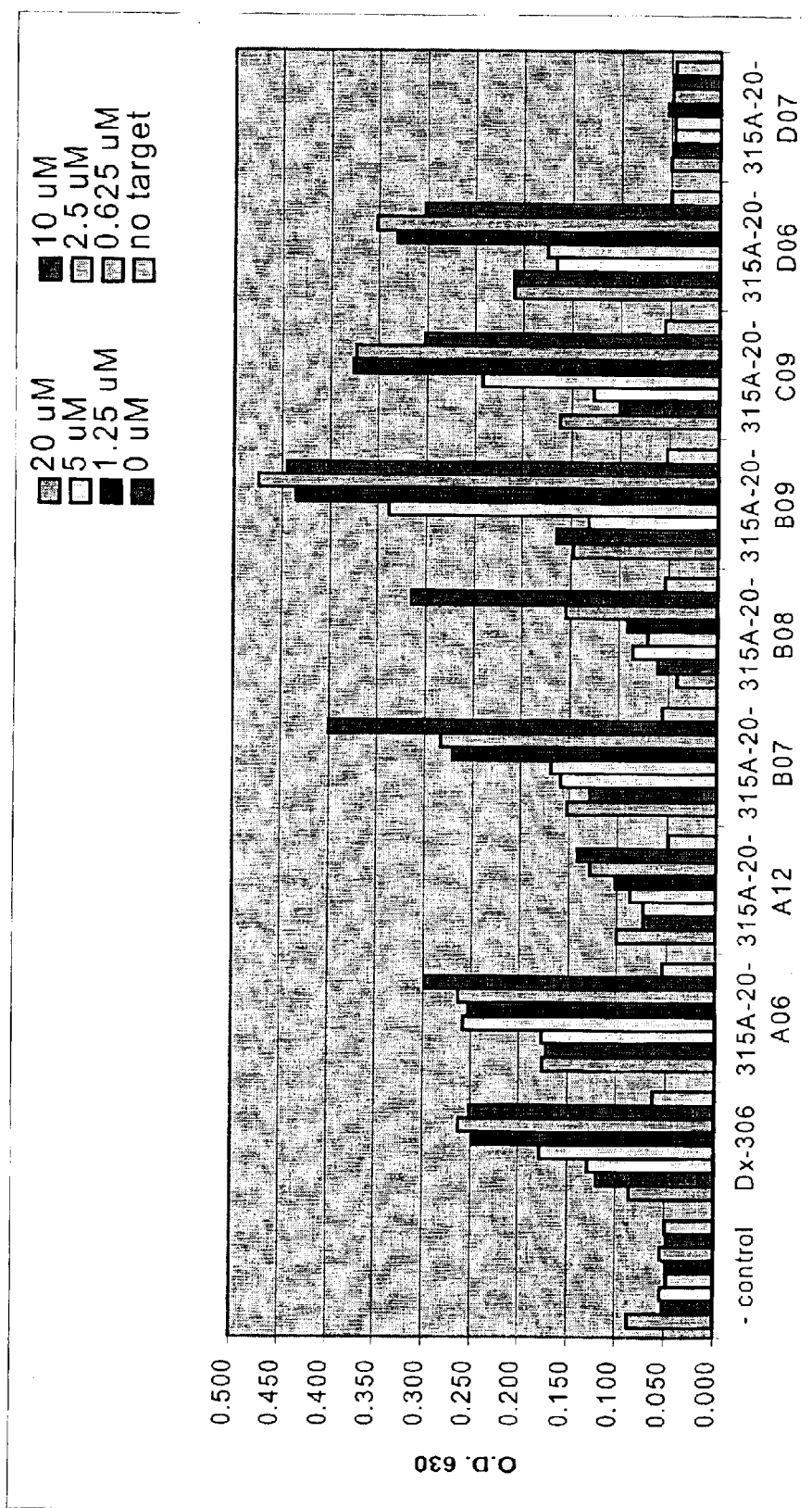
FIGS. 6(a)&(b) show competition ELISA scores for 18 different CEA-binding phage isolated following a high stringency, 18-hour elution of Lib2 (designated W3) to NA3 target with varying concentrations of soluble peptide DX306, having the amino acid sequence of Isolate 304A-12-H12 (SEQ ID NO:59). The first bar for each sample represents wells each having 20 $\mu$M of the DX306 binder, having the amino acid sequence of Isolate 304A-12-H12 (SEQ ID NO:59). Successive bars represent 10 $\mu$M, 5 $\mu$M, 2.5 $\mu$M, 1.25 $\mu$M, 0.625 $\mu$M, 0 M, and no target.
Figure 6B:
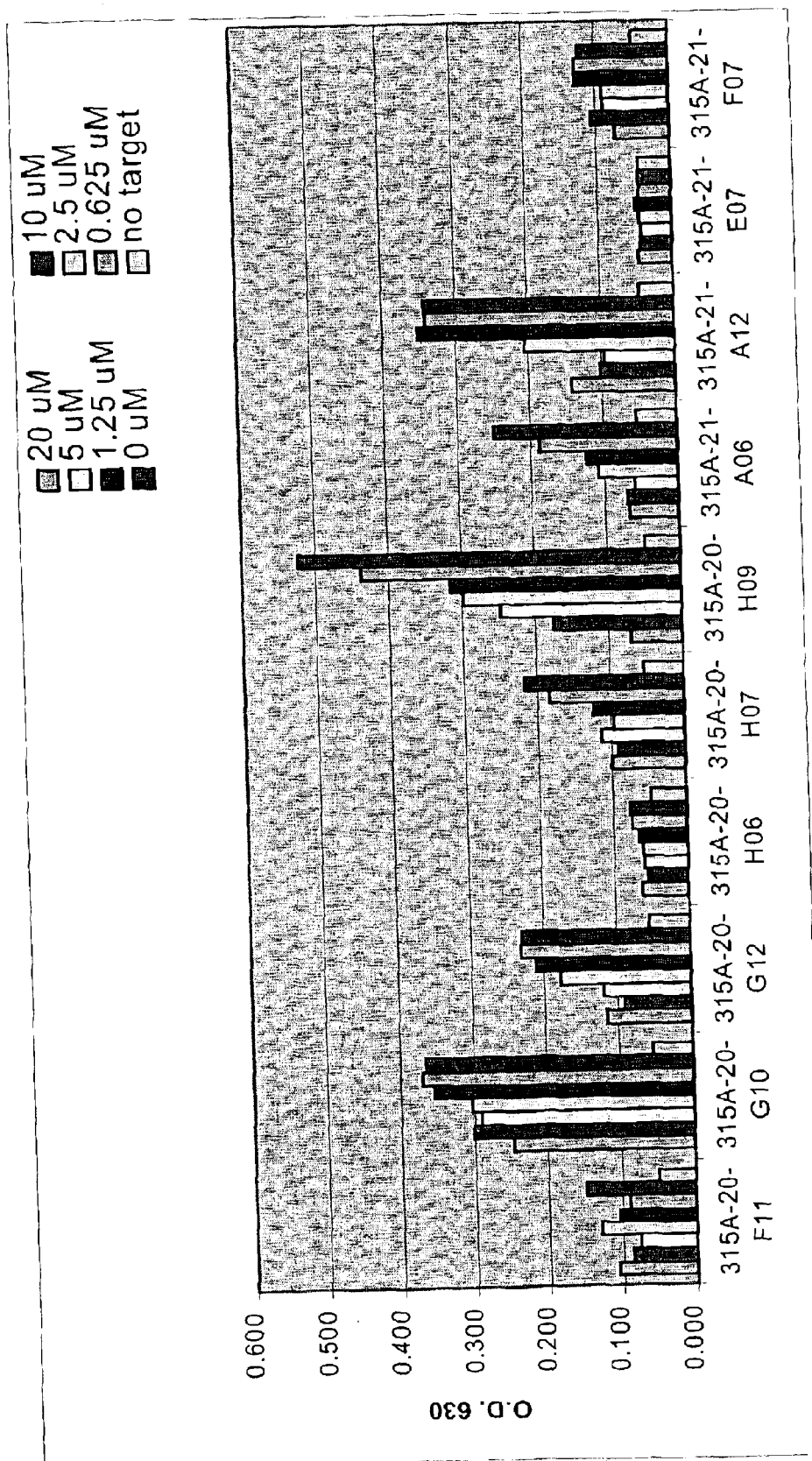
Figure 7:
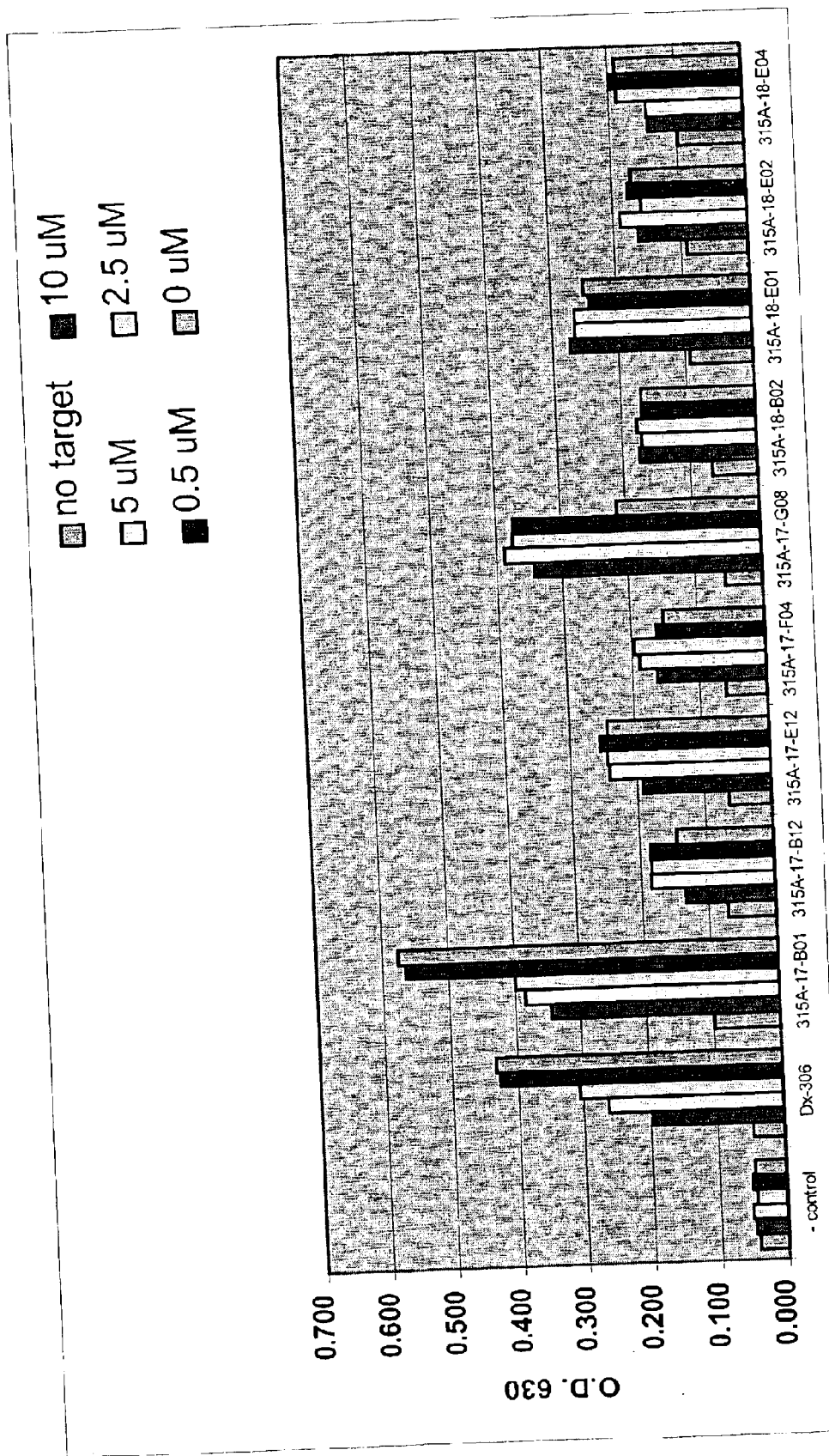
FIG. 7 shows competition ELISA scores for 9 different CEA-binding phage isolated following a high stringency, Factor X elution of Lib2 (designated W4) to NA3 target with varying concentrations of soluble peptide DX306, having the amino acid sequence of Isolate 304A-12-H12 (SEQ ID NO:59). The first bar for each sample represents wells each having no target. Successive bars represent 10 $\mu$M, 5 $\mu$M, 2.5 $\mu$M, 0.5 $\mu$M, and 0 M of the DX306 binder, having the amino acid sequence of Isolate 304A-12-H12 (SEQ ID NO:59).

FIGS. 6($a$)&6($b$) show the binding profile of the same 18 CEA binders isolated from the 18-hour elution (W3) to NA3 in a competition assay varying concentrations of a soluble peptide having the 304A-12-H12 sequence (DX306). FIG. 7 shows the binding profile of the nine (9) CEA binders isolated from the Factor X elution (W4) to NA3 in a competition assay varying concentrations of a soluble peptide having the 304A-12-H12 sequence (DX306).

EXAMPLE 11

High Stringency Isolate Binding Studies

The affinity of select peptides displayed by phage Isolates from the high stringency Lib2 screen were further tested in direct and competition binding studies (as in Examples 6 & 9). Peptides including the binding domain of the CEA binder Isolates were synthesized by solid-phase synthesis. Each peptide was also provided with a C-terminal amide-functional linker useful for immobilizing peptides to various chromatographic substrates: -$Ala_{18}$-$Pro_{19}$-$Gly_{20}$-Gly-Glu-Gly-Gly-Gly-Ser-Lys-$CONH_2$ (SEQ ID NO:28). The tripeptide -$Ala_{18}$-$Pro_{19}$-$Gly_{20}$- replicates part of the context of the phage-displayed peptides, and the remainder of the C-terminus is a synthetic linker for immobilization. Aliquots of each peptide were fluorescently labeled using NHS-fluorescein reacted with the $\epsilon$-amino side group of the C-terminal lysine.

Dissociation constants were determined using fluorescence anisotropy, through direct binding measurements to either NA-3 or CEA in PBS with 0.01% TWEEN 20. In direct binding assays, the concentration of the fluorescein-labeled peptide is held constant and the concentration of NA3 is varied. In the competition experiment, the concentration of the fluorescein-labeled peptide and the NA3 target are held constant and the concentration of competitor peptide (from Isolate 12-H12) is varied. The change in anisotropy is fit to the appropriate equation via nonlinear regression to obtain the apparent $K_d$. Isolate 304A-12-H12, previously isolated from Lib2 and assayed for binding, was analyzed in parallel as a control. Replicate analyses were run for certain binders and are reported to confirm accuracy and precision of measurements. $K_D$ standard error values are calculated from the nonlinear regression (SIGMAPLOT, SPSS Science, Chicago, Ill.). The dissociation constants that describe binding of the synthetic peptides for each of these targets are set forth in Table 10.

TABLE 10

Dissociation constants ($K_D$) for CEA binding peptides

| Isolate | SEQ ID NO: | NA3 $K_D$ ($\mu$M) direct binding | $K_D$ ($\mu$M) competition | CEA $K_D$ ($\mu$M) direct binding |
|---|---|---|---|---|
| 304A-12-H12 (DX306) | 59 | 0.30 ± 0.07<br>0.22 ± 0.04 | 0.34 ± 0.13<br>0.24 ± 0.09 | 3.7 ± 3.9 |
| 315A-17-B01 | 140 | 0.95 ± 0.16 | 0.90 ± 0.30<br>1.20 ± 0.29 | (not done) |
| 315A-17-B12 | 144 | 1.8 ± 1 | 0.65 ± 0.36 | (no binding) |
| 315A-17-G08 | 147 | 0.27 ± 0.07 | 0.16 ± 0.05<br>0.16 ± 0.09 | 1.6 ± 0.1 |
| 315A-18-E01 | 149 | 0.87 ± 0.21 | 0.23 ± 0.06<br>0.49 ± 0.21<br>0.17 ± 0.06 | (not done) |
| 315A-18-E02 | 150 | 0.38 ± 0.13 | 0.31 ± 0.19<br>0.29 ± 0.09<br>0.22 ± 0.09<br>0.14 ± 0.04 | 2.6 ± 1.7 |

The DX306 peptide was previously measured to bind NA3 with a $K_D$ of 0.24±0.03 $\mu$M; within the standard error of the present measurement. The data indicate that these high stringency CEA binders bind NA-3 with approximately the same affinity as DX306 (the control peptide).

304A-12-H12, 315A-17-G08, and 315A-18-E02 also effectively bound CEA, but not as strongly as they bound NA3. 315A-17-B12 did not appear to bind CEA. Decreased affinity for CEA binding may be attributable to a structural difference in the proteins, affecting peptide binding, or the presence of a significant concentration of nonfunctional (inactive) CEA in the commercial preparation.

Although a number of embodiments and features have been described above, it will be understood by those skilled in the art that modifications and variations of the described embodiments and features may be made without departing from the present disclosure or the invention as defined in the appended claims. The publications cited herein are incorporated by reference.

What is claimed is:

1. A polypeptide having the ability to bind CEA comprising the amino acid sequence:

$$Cys-X_4-X_5-X_6-X_7-X_8-X_9-X_{10}-X_{11}-Cys,$$ (SEQ ID NO:110)

wherein:

$X_4$ is Asn, Glu, Asp, or Met;

$X_5$ is Leu, Phe, Tyr, Trp, Val, Met, Ile, or Asn;

$X_6$ is Phe, Leu, Asp, Glu, Ala, Ile, Lys, Asn, Ser, Val, Trp, Tyr, Gly, or Thr;

$X_7$ is Lys, Phe, Asp, Gly, Leu, Asn, Trp, Ala, Gln, or Thr;

$X_8$ is Asn, Pro, Phe, Gly, Asp, Ala, Ser, Glu, Gln, Trp, His, Arg, Met, Val, or Leu;

$X_9$ is Gln, Lys, Leu, or Gly;

$X_{10}$ is Trp, Ala, or Tyr; and $X_{11}$ is Phe, Thr, Met, Ser, Ala, Asn, Val, His, Ile, Pro, Trp, Tyr, Gly, Leu, or Glu.

2. A polypeptide having the ability to bind CEA comprising the amino acid sequence:

$$X_1-X_2-X_3-Cys-X_4-X_5-X_6-X_7-X_8-X_9-X_{10}-X_{11}-Cys-X_{12}-X_{13}-X_{14},$$ (SEQ ID NO:19)

wherein:

$X_1$ is Asp, Asn, Ala, or Ile;

$X_2$ is Trp;

$X_3$ is Val, Ile, Met, Tyr, Phe, Pro, or Asp;

$X_4$ is Asn, Glu, Asp, or Met;

$X_5$ is Leu, Phe, Tyr, Trp, Val, Met, Ile, or Asn;

$X_6$ is Phe, Leu, Asp, Glu, Ala, Ile, Lys, Asn, Ser, Val, Trp, Tyr, Gly, or Thr;

$X_7$ is Lys, Phe, Asp, Gly, Leu, Asn, Trp, Ala, Gln, or Thr;

$X_8$ is Asn, Pro, Phe, Gly, Asp, Ala, Ser, Glu, Gln, Trp, His, Arg, Met, Val, or Leu;

$X_9$ is Gln, Lys, Leu, or Gly;

$X_{10}$ is Trp, Ala, or Tyr;

$X_{11}$ is Phe, Thr, Met, Ser, Ala, Asn, Val, His, Ile, Pro, Trp, Tyr, Gly, Leu, or Glu;

$X_{12}$ is Asn, Asp, Glu, Pro, Gln, Ser, Phe, or Val;

$X_{13}$ is Val, Leu, Ile, Pro, Ala, Gln, Ser, Met, Glu, Thr, Lys, Trp, or Arg; and $X_{14}$ is Leu, Met, Val, Tyr, Ala, Ile, Trp, His, Pro, Gln, Glu, Phe, Lys, Arg, or Ser.

3. A polypeptide having the ability to bind CEA comprising the amino acid sequence:

$$Cys-X_4-X_5-X_6-X_7-X_8-X_9-X_{10}-X_{11}-Cys,$$ (SEQ ID NO:3)

wherein:

$X_4$ is Asn, Glu, or Met;

$X_5$ is Asn, Leu, Met or Phe;

$X_6$ is Asp, Gly, Ile, Lys Phe or Thr;

$X_7$ is Ala, Gln, Gly, Lys or Thr;

$X_8$ is Arg, Asn, Asp, Glu or Gly;

$X_9$ is Gln, Gly or Leu;

$X_{10}$ is Ala, Trp or Tyr;

$X_{11}$ is Ala, Gly, His, Phe, Thr or Val;

4. The polypeptide according to claim 3, wherein:

$X_4$ is Glu;

$X_5$ is Asn, Leu, Met or Phe;

$X_6$ is Asp, Gly, Ile, Lys, Phe or Thr;

$X_7$ is Lys;

$X_8$ is Arg, Asn, Asp, Glu or Gly;

$X_9$ is Gln;

$X_{10}$ is Trp; and $X_{11}$ is Ala, Gly, His, Phe, Thr or Val.

5. The polypeptide according to claim 3, comprising the amino acid sequence:

$X_1-X_2-X_3-Cys-X_4-X_5-X_6-X_7-X_8-X_9-X_{10}-X_{11}-Cys-X_{12}-X_{13}-X_{14}$, (SEQ ID NO:1)

wherein:

$X_1$ is Asn or Asp;

$X_2$ is Trp;

$X_3$ is Asp, Phe or Val;

$X_4$ is Asn, Glu or Met;

$X_5$ is Asn, Leu, Met or Phe;

$X_6$ is Asp, Gly, Ile, Lys, Phe or Thr;

$X_7$ is Ala, Gln, Gly, Lys or Thr;

$X_8$ is Arg, Asn, Asp, Glu or Gly;

$X_9$ is Gln, Gly or Leu;

$X_{10}$ is Ala, Trp or Tyr;

$X_{11}$ is Ala, Gly, His, Phe, Thr or Val;

$X_{12}$ is Asn, Gln, Phe, Ser or Val;

$X_{13}$ is Arg, Leu, Pro or Ser; and $X_{14}$ is Leu, Ser, Trp or Tyr.

6. The polypeptide according to claim 5, having the amino acid sequence:

$X_1-Trp-Val-Cys-Glu-X_5-X_6-Lys-X_8-Gln-Trp-X_{11}-Cys-Asn-X_{13}-X_{14}$, (SEQ ID NO:2)

wherein:

$X_1$ is Asn or Asp;

$X_5$ is Asn, Leu, Met or Phe;

$X_6$ is Asp, Gly, Ile, Lys, Phe or Thr;

$X_8$ is Arg, Asn, Asp, Glu or Gly;

$X_{11}$ is Ala, Gly, His, Phe, Thr or Val;

$X_{13}$ is Arg, Leu, Pro or Ser; and $X_{14}$ is Leu or Tyr.

7. The polypeptide according to claim 5, comprising an amino acid sequence selected from the group consisting of:

Asn-Trp-Val-Cys-Asn-Leu-Phe-Lys-Asn-Gln-Trp-Phe-Cys-Asn-Ser-Tyr; (SEQ ID NO:4)

Asp-Trp-Val-Cys-Glu-Asn-Lys-Lys-Asp-Gln-Trp-Thr-Cys-Asn-Leu-Leu; (SEQ ID NO:5)

Asn-Trp-Asp-Cys-Met-Phe-Gly-Ala-Glu-Gly-Trp-Ala-Cys-Ser-Pro-Trp; (SEQ ID NO:6)

Asp-Trp-Val-Cys-Glu-Lys-Thr-Thr-Gly-Gly-Tyr-Val-Cys-Gln-Pro-Leu; (SEQ ID NO:7)

Asn-Trp-Phe-Cys-Glu-Met-Ile-Gly-Arg-Gln-Trp-Gly-Cys-Val-Pro-Ser; and (SEQ ID NO:8)

Asp-Trp-Val-Cys-Asn-Phe-Asp-Gln-Gly-Leu-Ala-His-Cys-Phe-Pro-Ser. (SEQ ID NO:9)

8. A polypeptide having the ability to bind CEA comprising the amino acid sequence:

$X_1-X_2-X_3-Cys-X_4-X_5-X_6-X_7-X_8-X_9-X_{10}-X_{11}-Cys-X_{12}-X_{13}-X_{14}$, wherein: (SEQ ID NO:1)

$X_1$ is Asp, Asn, Ala, or Ile;

$X_2$ is Trp;

$X_3$ is Val, Ile, Met, Tyr, Phe, Pro, or Asp;

$X_4$ is Asn, Glu, or Asp;

$X_5$ is Leu, Phe, Tyr, Trp, Val, Met, Ile, or Asn;

$X_6$ is Phe, Leu, Asp, Glu, Ala, Ile, Lys, Asn, Ser, Val, Trp, or Tyr;

$X_7$ is Lys, Phe, Asp, Gly, Leu, Asn, or Trp;

$X_8$ is Asn, Pro, Phe, Gly, Asp, Ala, Ser, Glu, Gln, or Trp;

$X_9$ is Gln, or Lys;

$X_{10}$ is Trp;

$X_{11}$ is Phe, Thr, Met, Ser, Ala, Asn, Val, His, Ile, Pro, Trp, or Tyr;

$X_{12}$ is Asn, Asp, Glu, Pro, Gln, or Ser;

$X_{13}$ is Val, Leu, Ile, Pro, Ala, Gln, Ser, Met, Glu, Thr, Lys, or Trp; and $X_{14}$ is Leu, Met, Val, Tyr, Ala, Ile, Trp, His, Pro, Gln, Glu, Phe, Lys, or Arg.

9. The polypeptide of claim 1, wherein:

$X_4$ is Asn, or Glu;

$X_5$ is Leu, Phe, Tyr, Trp, or Ile;

$X_6$ is Phe, Leu, Asp, Glu, Ile, Ser, Val, or Gly;

$X_7$ is Lys;

$X_8$ is Asn, Pro, Gly, Asp, Ala, Ser, His, Met, Val, or Leu;

$X_9$ is Gln;

$X_{10}$ is Trp;

$X_{11}$ is Phe, Thr, Ser, Ala, Asn, Val, His, Ile, Trp, Tyr, Leu, or Glu;

10. The polypeptide of claim 2, wherein:

$X_1$ is Asp, or Asn;

$X_2$ is Trp;

$X_3$ is Val, Ile, or Met;

$X_4$ is Asn, or Glu;

$X_5$ is Leu, Phe, Tyr, Trp, or Ile;

$X_6$ is Phe, Leu, Asp, Glu, Ile, Ser, Val, or Gly;

$X_7$ is Lys;

$X_8$ is Asn, Pro, Gly, Asp, Ala, Ser, His, Met, Val, or Leu;

$X_9$ is Gln;

-continued $X_{10}$ is Trp;

$X_{11}$ is Phe, Thr, Ser, Ala, Asn, Val, His, Ile, Trp, Tyr, Leu, or Glu;

$X_{12}$ is Asn, or Asp;

$X_{13}$ is Val, Leu, Ile, Pro, Ala, Gln, Ser, or Met; and $X_{14}$ is Leu, Met, Val, Tyr, Trp, His, Gln, Arg, or Ser.

11. The polypeptide according to claim 2, comprising an amino acid sequence selected from the group consisting of SEQ ID NOs: 37–109 and 113–151.

12. The polypeptide according to claim 1, 2, 3, 5, 8, 9, or 10, wherein said polypeptide binds to CEA but does not bind to NCA.

13. The polypeptide according to claim 1, 2, 3, 5, 8, 9, or 10, wherein said polypeptide has a $K_d$ for CEA which less than 7 $\mu$M.

* * * * *

UNITED STATES PATENT AND TRADEMARK OFFICE
CERTIFICATE OF CORRECTION

PATENT NO.        : 6,919,424 B2
APPLICATION NO. : 09/825517
DATED              : July 19, 2005
INVENTOR(S)      : Rondon et al.

Page 1 of 1

It is certified that error appears in the above-identified patent and that said Letters Patent is hereby corrected as shown below:

Cover Page – Patent 5,872,215, replace "Osbourne" with --Osborne--;

Cover Page – "Imbach" reference publication, replace "Mutatuion" with --Mutation--;

Cover Page – "Mach" reference publication, replace "239-349" with --239-249--;

Col. 101, line 46, between "$X_5$-$X_6$" move "(SEQ ID NO: 19)" to the right as done in claims 1 and 3;

Col. 101, line 63, after "Glu," replace "Gln" with --Gin--;

Col. 102, line 21, after "Tyr;" insert --and--;

Col. 102, line 51, after "Val" replace ";" with --.--;

Col. 102, line 64, after "Trp;" delete "and";

Col. 104, line 49, after "Glu" replace ";" with --.--.

Signed and Sealed this

Twenty-ninth Day of August, 2006

JON W. DUDAS
*Director of the United States Patent and Trademark Office*

SEQUENCE LISTING

```
<160> NUMBER OF SEQ ID NOS: 151

<210> SEQ ID NO 1
<211> LENGTH: 16
<212> TYPE: PRT
<213> ORGANISM: Artificial Sequence
<220> FEATURE:
<223> OTHER INFORMATION: CEA binding polypeptide
<220> FEATURE:
<221> NAME/KEY: VARIANT
<222> LOCATION: 1
<223> OTHER INFORMATION: Xaa is Asn, Asp or is absent
<220> FEATURE:
<221> NAME/KEY: VARIANT
<222> LOCATION: 2
<223> OTHER INFORMATION: Xaa is Trp
<220> FEATURE:
<221> NAME/KEY: VARIANT
<222> LOCATION: 3
<223> OTHER INFORMATION: Xaa is Asp, Phe or Val
<220> FEATURE:
<221> NAME/KEY: VARIANT
<222> LOCATION: 5
<223> OTHER INFORMATION: Xaa is Asn, Glu or Met
<220> FEATURE:
<221> NAME/KEY: VARIANT
<222> LOCATION: 6
<223> OTHER INFORMATION: Xaa is Asn, Leu, Met or Phe
<220> FEATURE:
<221> NAME/KEY: VARIANT
<222> LOCATION: (7)...(7)
<223> OTHER INFORMATION: Xaa is Asp, Gly, Ile, Lys, Phe or Thr
<220> FEATURE:
<221> NAME/KEY: VARIANT
<222> LOCATION: (8)...(8)
<223> OTHER INFORMATION: Xaa is Ala, Gln, Gly, Lys or Thr
<220> FEATURE:
<221> NAME/KEY: VARIANT
<222> LOCATION: (9)...(9)
<223> OTHER INFORMATION: Xaa is Arg, Asn, Asp, Glu or Gly
<220> FEATURE:
<221> NAME/KEY: VARIANT
<222> LOCATION: (10)...(10)
<223> OTHER INFORMATION: Xaa is Gln, Leu or Gly
<220> FEATURE:
<221> NAME/KEY: VARIANT
<222> LOCATION: (11)...(11)
<223> OTHER INFORMATION: Xaa is Ala, Trp or Tyr
<220> FEATURE:
```

```
<221> NAME/KEY: VARIANT
<222> LOCATION: (12)...(12)
<223> OTHER INFORMATION: Xaa is Ala, Gly, His, Phe, Thr or Val
<220> FEATURE:
<221> NAME/KEY: VARIANT
<222> LOCATION: (14)...(14)
<223> OTHER INFORMATION: Xaa is Asn, Gln, Phe, Ser or Val
<220> FEATURE:
<221> NAME/KEY: VARIANT
<222> LOCATION: (15)...(15)
<223> OTHER INFORMATION: Xaa is Arg, Leu, Pro or Ser
<220> FEATURE:
<221> NAME/KEY: VARIANT
<222> LOCATION: (16)...(16)
<223> OTHER INFORMATION: Xaa is Leu, Ser, Trp or Tyr

<400> SEQUENCE: 1

Xaa Xaa Xaa Cys Xaa Xaa Xaa Xaa Xaa Xaa Xaa Xaa Cys Xaa Xaa Xaa
 1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Family of preferred CEA binding moieties
<220> FEATURE:
<221> NAME/KEY: VARIANT
<222> LOCATION: 1
<223> OTHER INFORMATION: Xaa is Asn or Asp
<220> FEATURE:
<221> NAME/KEY: VARIANT
<222> LOCATION: 6
<223> OTHER INFORMATION: Xaa is Phe, Met, Leu or Asn
<220> FEATURE:
<221> NAME/KEY: VARIANT
<222> LOCATION: 7
<223> OTHER INFORMATION: Xaa is Asp, Gly, Ile, Lys, Phe or Thr
<220> FEATURE:
<221> NAME/KEY: VARIANT
<222> LOCATION: 9
<223> OTHER INFORMATION: Xaa is Arg, Asn, Asp, Glu, Gly or Trp
<220> FEATURE:
<221> NAME/KEY: VARIANT
<222> LOCATION: 12
<223> OTHER INFORMATION: Xaa is Ala, Gly, His, Phe, Thr, Tyr or Val
<220> FEATURE:
<221> NAME/KEY: VARIANT
<222> LOCATION: (15)...(15)
<223> OTHER INFORMATION: Xaa is Arg, Leu, Pro or Ser
<220> FEATURE:
<221> NAME/KEY: VARIANT
<222> LOCATION: (16)...(16)
<223> OTHER INFORMATION: Xaa is Leu, Ser, Trp or Tyr

<400> SEQUENCE: 2

Xaa Trp Val Cys Glu Xaa Xaa Lys Xaa Gln Trp Xaa Cys Asn Xaa Xaa
 1               5                   10                  15

<210> SEQ ID NO 3
<211> LENGTH: 10
<212> TYPE: PRT
<213> ORGANISM: Artificial Sequence
<220> FEATURE:
<223> OTHER INFORMATION: CEA binding loop
<220> FEATURE:
<221> NAME/KEY: VARIANT
<222> LOCATION: 2
<223> OTHER INFORMATION: Xaa is Asn, Glu or Met
<220> FEATURE:
<221> NAME/KEY: VARIANT
<222> LOCATION: 3
<223> OTHER INFORMATION: Xaa is Asn, Leu, Met or Phe
<220> FEATURE:
<221> NAME/KEY: VARIANT
```

```
<222> LOCATION: 4
<223> OTHER INFORMATION: Xaa is Asp, Gly, Ile, Lys, Phe or Thr
<220> FEATURE:
<221> NAME/KEY: VARIANT
<222> LOCATION: 5
<223> OTHER INFORMATION: Xaa is Ala, Gln, Gly, Lys or Thr
<220> FEATURE:
<221> NAME/KEY: VARIANT
<222> LOCATION: 6
<223> OTHER INFORMATION: Xaa is Arg, Asn, Asp, Glu or Gly
<220> FEATURE:
<221> NAME/KEY: VARIANT
<222> LOCATION: (7)...(7)
<223> OTHER INFORMATION: Xaa is Gln, Gly or Leu
<220> FEATURE:
<221> NAME/KEY: VARIANT
<222> LOCATION: (8)...(8)
<223> OTHER INFORMATION: Xaa is Ala, Trp or Tyr
<220> FEATURE:
<221> NAME/KEY: VARIANT
<222> LOCATION: (9)...(9)
<223> OTHER INFORMATION: Xaa is Ala, Gly, His, Phe, Thr or Val

<400> SEQUENCE: 3

Cys Xaa Xaa Xaa Xaa Xaa Xaa Xaa Cys
1               5                   10

<210> SEQ ID NO 4
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 4

Asn Trp Val Cys Asn Leu Phe Lys Asn Gln Trp Phe Cys Asn Ser Tyr
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 5

Asp Trp Val Cys Glu Asn Lys Lys Asp Gln Trp Thr Cys Asn Leu Leu
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 6

Asn Trp Asp Cys Met Phe Gly Ala Glu Gly Trp Ala Cys Ser Pro Trp
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 7

Asp Trp Val Cys Glu Lys Thr Thr Gly Gly Tyr Val Cys Gln Pro Leu
1               5                   10                  15
```

<210> SEQ ID NO 8
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 8

Asn Trp Phe Cys Glu Met Ile Gly Arg Gln Trp Gly Cys Val Pro Ser
 1               5                  10                  15

<210> SEQ ID NO 9
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 9

Asp Trp Val Cys Asn Phe Asp Gln Gly Leu Ala His Cys Phe Pro Ser
 1               5                  10                  15

<210> SEQ ID NO 10
<211> LENGTH: 12
<212> TYPE: PRT
<213> ORGANISM: Artificial Sequence
<220> FEATURE:
<223> OTHER INFORMATION: Parental domain for design of microprotein
      display library
<220> FEATURE:
<221> NAME/KEY: VARIANT
<222> LOCATION: (1)...(12)
<223> OTHER INFORMATION: amino acid positions 4 and 9 are invariant Cys;
      all other positions Xaa are varied but not Cys, to
      provide a library of 2x10(8) different peptides
      based on the template sequence
<220> FEATURE:
<221> NAME/KEY: VARIANT
<222> LOCATION: 1, 2, 3, 5, 6, 7, 8, 10, 11, 12
<223> OTHER INFORMATION: Xaa = Any Amino Acid except Cys

<400> SEQUENCE: 10

Xaa Xaa Xaa Cys Xaa Xaa Xaa Xaa Cys Xaa Xaa Xaa
 1               5                  10

<210> SEQ ID NO 11
<211> LENGTH: 11
<212> TYPE: PRT
<213> ORGANISM: Artificial Sequence
<220> FEATURE:
<223> OTHER INFORMATION: Parental domain for design of microprotein
      display library
<220> FEATURE:
<221> NAME/KEY: VARIANT
<222> LOCATION: (1)...(11)
<223> OTHER INFORMATION: amino acid positions 3 and 9 are invariant Cys;
      all other positions Xaa are varied but not Cys, to
      provide a library of 1x10(9) different peptides
      based on the template sequence
<220> FEATURE:
<221> NAME/KEY: VARIANT
<222> LOCATION: 1, 2, 4, 5, 6, 7, 8, 10, 11
<223> OTHER INFORMATION: Xaa = Any Amino Acid except Cys

<400> SEQUENCE: 11

Xaa Xaa Cys Xaa Xaa Xaa Xaa Xaa Cys Xaa Xaa
 1               5                  10

<210> SEQ ID NO 12

```
<211> LENGTH: 12
<212> TYPE: PRT
<213> ORGANISM: Artificial Sequence
<220> FEATURE:
<223> OTHER INFORMATION: Parental domain for design of microprotein
      display library
<220> FEATURE:
<221> NAME/KEY: VARIANT
<222> LOCATION: (1)...(12)
<223> OTHER INFORMATION: amino acid positions 3 and 10 are invariant
      Cys; all other positions Xaa are varied but not Cys, to
      provide a library of 1x10(9) different peptides
      based on the template sequence
<220> FEATURE:
<221> NAME/KEY: VARIANT
<222> LOCATION: 1, 2, 4, 5, 6, 7, 8, 9, 11, 12
<223> OTHER INFORMATION: Xaa = Any Amino Acid except Cys

<400> SEQUENCE: 12

Xaa Xaa Cys Xaa Xaa Xaa Xaa Xaa Xaa Cys Xaa Xaa
 1               5                  10

<210> SEQ ID NO 13
<211> LENGTH: 16
<212> TYPE: PRT
<213> ORGANISM: Artificial Sequence
<220> FEATURE:
<223> OTHER INFORMATION: Parental domain for design of microprotein
      display library
<220> FEATURE:
<221> NAME/KEY: VARIANT
<222> LOCATION: (1)...(16)
<223> OTHER INFORMATION: amino acid positions 4 and 13 are invariant
      Cys; all other positions Xaa are varied but not Cys, to
      provide a library of 2.5x10(8) different peptides
      based on the template sequence
<220> FEATURE:
<221> NAME/KEY: VARIANT
<222> LOCATION: 1, 2, 3, 5, 6, 7, 8, 9, 10, 11, 12, 14, 15, 16
<223> OTHER INFORMATION: Xaa = Any Amino Acid except Cys

<400> SEQUENCE: 13

Xaa Xaa Xaa Cys Xaa Xaa Xaa Xaa Xaa Xaa Xaa Xaa Cys Xaa Xaa Xaa
 1               5                  10                  15

<210> SEQ ID NO 14
<211> LENGTH: 16
<212> TYPE: PRT
<213> ORGANISM: Artificial Sequence
<220> FEATURE:
<223> OTHER INFORMATION: Variable sublibrary sequence used in designing
      focused secondary library
<220> FEATURE:
<221> NAME/KEY: VARIANT
<222> LOCATION: (1)...(3)
<223> OTHER INFORMATION: Xaa is any amino acid except Cys
<220> FEATURE:
<221> NAME/KEY: VARIANT
<222> LOCATION: (5)...(6)
<223> OTHER INFORMATION: Xaa is any amino acid except Cys
<220> FEATURE:
<221> NAME/KEY: VARIANT
<222> LOCATION: 1, 2, 3, 5, 6
<223> OTHER INFORMATION: Xaa = Any Amino Acid except Cys

<400> SEQUENCE: 14

Xaa Xaa Xaa Cys Xaa Xaa Lys Lys Asp Gln Trp Thr Cys Asn Leu Leu
 1               5                  10                  15

<210> SEQ ID NO 15
<211> LENGTH: 16
<212> TYPE: PRT
<213> ORGANISM: Artificial Sequence
```

```
<220> FEATURE:
<223> OTHER INFORMATION: Variable sublibrary sequence used in designing
      focused secondary library
<220> FEATURE:
<221> NAME/KEY: VARIANT
<222> LOCATION: (5)...(9)
<223> OTHER INFORMATION: Xaa is any amino acid except Cys
<220> FEATURE:
<221> NAME/KEY: VARIANT
<222> LOCATION: 5, 6, 7, 8, 9
<223> OTHER INFORMATION: Xaa = Any Amino Acid except Cys

<400> SEQUENCE: 15

Asp Trp Val Cys Xaa Xaa Xaa Xaa Xaa Gln Trp Thr Cys Asn Leu Leu
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Variable sublibrary sequence used in designing
      focused secondary library
<220> FEATURE:
<221> NAME/KEY: VARIANT
<222> LOCATION: (8)...(12)
<223> OTHER INFORMATION: Xaa is any amino acid except Cys
<220> FEATURE:
<221> NAME/KEY: VARIANT
<222> LOCATION: 8, 9, 10, 11, 12
<223> OTHER INFORMATION: Xaa = Any Amino Acid except Cys

<400> SEQUENCE: 16

Asp Trp Val Cys Glu Asn Lys Xaa Xaa Xaa Xaa Xaa Cys Asn Leu Leu
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Variable sublibrary sequence used in designing
      focused secondary library
<220> FEATURE:
<221> NAME/KEY: VARIANT
<222> LOCATION: (11)...(12)
<223> OTHER INFORMATION: Xaa is any amino acid except Cys
<220> FEATURE:
<221> NAME/KEY: VARIANT
<222> LOCATION: (14)...(16)
<223> OTHER INFORMATION: Xaa is any amino acid except Cys
<220> FEATURE:
<221> NAME/KEY: VARIANT
<222> LOCATION: 11, 12, 14, 15, 16
<223> OTHER INFORMATION: Xaa = Any Amino Acid except Cys

<400> SEQUENCE: 17

Asp Trp Val Cys Glu Asn Lys Lys Asp Gln Xaa Xaa Cys Xaa Xaa Xaa
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Variable sublibrary sequence used in designing
      focused secondary library
<220> FEATURE:
<221> NAME/KEY: VARIANT
<222> LOCATION: (6)...(7)
<223> OTHER INFORMATION: Xaa is any amino acid except Cys
<220> FEATURE:
<221> NAME/KEY: VARIANT
```

```
<222> LOCATION: 9
<223> OTHER INFORMATION: Xaa is any amino acid except Cys
<220> FEATURE:
<221> NAME/KEY: VARIANT
<222> LOCATION: 12
<223> OTHER INFORMATION: Xaa is any amino acid except Cys
<220> FEATURE:
<221> NAME/KEY: VARIANT
<222> LOCATION: 15
<223> OTHER INFORMATION: Xaa is any amino acid except Cys
<220> FEATURE:
<221> NAME/KEY: VARIANT
<222> LOCATION: 6, 7, 9, 12, 15
<223> OTHER INFORMATION: Xaa = Any Amino Acid except Cys

<400> SEQUENCE: 18

Asp Trp Val Cys Glu Xaa Xaa Lys Xaa Gln Trp Xaa Cys Asn Xaa Leu
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Variable sublibrary sequence used in designing
      focused secondary library
<220> FEATURE:
<221> NAME/KEY: VARIANT
<222> LOCATION: (5)...(7)
<223> OTHER INFORMATION: Xaa is any amino acid except Cys
<220> FEATURE:
<221> NAME/KEY: VARIANT
<222> LOCATION: 9
<223> OTHER INFORMATION: Xaa is any amino acid except Cys
<220> FEATURE:
<221> NAME/KEY: VARIANT
<222> LOCATION: 12
<223> OTHER INFORMATION: Xaa is any amino acid except Cys
<220> FEATURE:
<221> NAME/KEY: VARIANT
<222> LOCATION: 5, 6, 7, 9, 12
<223> OTHER INFORMATION: Xaa = Any Amino Acid except Cys

<400> SEQUENCE: 19

Asn Trp Val Cys Xaa Xaa Xaa Lys Xaa Gln Trp Xaa Cys Asn Ser Tyr
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Variable sublibrary sequence used in designing
      focused secondary library
<220> FEATURE:
<221> NAME/KEY: VARIANT
<222> LOCATION: 1
<223> OTHER INFORMATION: Xaa is any amino acid except Cys
<220> FEATURE:
<221> NAME/KEY: VARIANT
<222> LOCATION: 3
<223> OTHER INFORMATION: Xaa is any amino acid except Cys
<220> FEATURE:
<221> NAME/KEY: VARIANT
<222> LOCATION: (14)...(16)
<223> OTHER INFORMATION: Xaa is any amino acid except Cys
<220> FEATURE:
<221> NAME/KEY: VARIANT
<222> LOCATION: 1, 3, 14, 15, 16
<223> OTHER INFORMATION: Xaa = Any Amino Acid except Cys

<400> SEQUENCE: 20

Xaa Trp Xaa Cys Asn Leu Phe Lys Asn Gln Trp Phe Cys Xaa Xaa Xaa
1               5                   10                  15
```

```
<210> SEQ ID NO 21
<211> LENGTH: 16
<212> TYPE: PRT
<213> ORGANISM: Artificial Sequence
<220> FEATURE:
<223> OTHER INFORMATION: Isolate of TN10/9 library found not to bind CEA

<400> SEQUENCE: 21

Asn Trp Arg Cys Lys Leu Phe Pro Arg Tyr Pro Tyr Cys Ser Ser Trp
 1               5                  10                  15

<210> SEQ ID NO 22
<211> LENGTH: 15
<212> TYPE: PRT
<213> ORGANISM: Artificial Sequence
<220> FEATURE:
<223> OTHER INFORMATION: Isolate of TN10/9 library found not to bind CEA

<400> SEQUENCE: 22

Arg Tyr Cys Glu Phe Phe Pro Trp Ser Leu His Cys Gly Arg Pro
 1               5                  10                  15

<210> SEQ ID NO 23
<211> LENGTH: 16
<212> TYPE: PRT
<213> ORGANISM: Artificial Sequence
<220> FEATURE:
<223> OTHER INFORMATION: Conserved amino acid positions in first family
      of CEA binding peptides
<220> FEATURE:
<221> NAME/KEY: VARIANT
<222> LOCATION: 6
<223> OTHER INFORMATION: X is Asn, Leu, Met or Phe
<220> FEATURE:
<221> NAME/KEY: VARIANT
<222> LOCATION: 7
<223> OTHER INFORMATION: X is Asp, Gly, Ile, Lys, Phe or Thr
<220> FEATURE:
<221> NAME/KEY: VARIANT
<222> LOCATION: 9
<223> OTHER INFORMATION: X is Arg, Asn, Asp, Glu or Gly
<220> FEATURE:
<221> NAME/KEY: VARIANT
<222> LOCATION: 12
<223> OTHER INFORMATION: X is Ala, Gly, His, Phe, Thr or Val
<220> FEATURE:
<221> NAME/KEY: VARIANT
<222> LOCATION: 15
<223> OTHER INFORMATION: X is Arg, Leu, Pro or Ser

<400> SEQUENCE: 23

Asp Trp Val Cys Glu Xaa Xaa Lys Xaa Gln Trp Xaa Cys Asn Xaa Leu
 1               5                  10                  15

<210> SEQ ID NO 24
<211> LENGTH: 27
<212> TYPE: PRT
<213> ORGANISM: Artificial Sequence
<220> FEATURE:
<223> OTHER INFORMATION: Synthetic CEA binding peptide with C-terminal
      immobilization sequence

<400> SEQUENCE: 24

Ser Asn Trp Val Cys Asn Leu Phe Lys Asn Gln Trp Phe Cys Asn Ser
 1               5                  10                  15

Tyr Ala Pro Gly Gly Glu Gly Gly Gly Ser Lys
                20                  25
```

<210> SEQ ID NO 25
<211> LENGTH: 27
<212> TYPE: PRT
<213> ORGANISM: Artificial Sequence
<220> FEATURE:
<223> OTHER INFORMATION: Synthetic CEA binding peptide with C-terminal
      immobilization sequence

<400> SEQUENCE: 25

Ser Asp Trp Val Cys Glu Asn Lys Lys Asp Gln Trp Thr Cys Asn Leu
1               5                   10                  15

Leu Ala Pro Gly Gly Glu Gly Gly Gly Ser Lys
            20                  25

<210> SEQ ID NO 26
<211> LENGTH: 27
<212> TYPE: PRT
<213> ORGANISM: Artificial Sequence
<220> FEATURE:
<223> OTHER INFORMATION: Synthetic CEA binding peptide with C-terminal
      immobilization sequence

<400> SEQUENCE: 26

Ser Asn Trp Asp Cys Met Phe Gly Ala Glu Gly Trp Ala Cys Ser Pro
1               5                   10                  15

Trp Ala Pro Gly Gly Glu Gly Gly Gly Ser Lys
            20                  25

<210> SEQ ID NO 27
<211> LENGTH: 27
<212> TYPE: PRT
<213> ORGANISM: Artificial Sequence
<220> FEATURE:
<223> OTHER INFORMATION: Synthetic CEA binding peptide with C-terminal
      immobilization sequence

<400> SEQUENCE: 27

Ser Asp Trp Val Cys Glu Leu Thr Thr Gly Gly Tyr Val Cys Gln Pro
1               5                   10                  15

Leu Ala Pro Gly Gly Glu Gly Gly Gly Ser Lys
            20                  25

<210> SEQ ID NO 28
<211> LENGTH: 10
<212> TYPE: PRT
<213> ORGANISM: Artificial Sequence
<220> FEATURE:
<223> OTHER INFORMATION: C-terminal sequence for immobilizing  peptides

<400> SEQUENCE: 28

Ala Pro Gly Gly Glu Gly Gly Gly Ser Lys
1               5                   10

<210> SEQ ID NO 29
<211> LENGTH: 16
<212> TYPE: PRT
<213> ORGANISM: Artificial Sequence
<220> FEATURE:
<223> OTHER INFORMATION: Template sequence for sublibrary used in
      construction of focused secondary display library
<220> FEATURE:
<221> NAME/KEY: VARIANT
<222> LOCATION: (1)...(3)
<223> OTHER INFORMATION: X is any amino acid except Cys
<220> FEATURE:
<221> NAME/KEY: VARIANT
<222> LOCATION: (5)...(6)
<223> OTHER INFORMATION: X is any amino acid except Cys

```
<220> FEATURE:
<221> NAME/KEY: VARIANT
<222> LOCATION: 1, 2, 3, 5, 6
<223> OTHER INFORMATION: Xaa = Any Amino Acid except Cys

<400> SEQUENCE: 29

Xaa Xaa Xaa Cys Xaa Xaa Lys Lys Asp Gln Trp Thr Cys Asn Leu Leu
 1               5                  10                  15

<210> SEQ ID NO 30
<211> LENGTH: 16
<212> TYPE: PRT
<213> ORGANISM: Artificial Sequence
<220> FEATURE:
<223> OTHER INFORMATION: Template sequence for sublibrary used in
      construction of focused secondary display library
<220> FEATURE:
<221> NAME/KEY: VARIANT
<222> LOCATION: (5)...(9)
<223> OTHER INFORMATION: X is any amino acid except Cys
<220> FEATURE:
<221> NAME/KEY: VARIANT
<222> LOCATION: 5, 6, 7, 8, 9
<223> OTHER INFORMATION: Xaa = Any Amino Acid except Cys

<400> SEQUENCE: 30

Asp Trp Val Cys Xaa Xaa Xaa Xaa Xaa Gln Trp Thr Cys Asn Leu Leu
 1               5                  10                  15

<210> SEQ ID NO 31
<211> LENGTH: 16
<212> TYPE: PRT
<213> ORGANISM: Artificial Sequence
<220> FEATURE:
<223> OTHER INFORMATION: Template sequence for sublibrary used in
      construction of focused secondary display library
<220> FEATURE:
<221> NAME/KEY: VARIANT
<222> LOCATION: (8)...(12)
<223> OTHER INFORMATION: X is any amino acid except Cys
<220> FEATURE:
<221> NAME/KEY: VARIANT
<222> LOCATION: 8, 9, 10, 11, 12
<223> OTHER INFORMATION: Xaa = Any Amino Acid except Cys

<400> SEQUENCE: 31

Asp Trp Val Cys Glu Asn Lys Xaa Xaa Xaa Xaa Xaa Cys Asn Leu Leu
 1               5                  10                  15

<210> SEQ ID NO 32
<211> LENGTH: 16
<212> TYPE: PRT
<213> ORGANISM: Artificial Sequence
<220> FEATURE:
<223> OTHER INFORMATION: Template sequence for sublibrary used in
      construction of focused secondary display library
<220> FEATURE:
<221> NAME/KEY: VARIANT
<222> LOCATION: (11)...(12)
<223> OTHER INFORMATION: X is any amino acid except Cys
<220> FEATURE:
<221> NAME/KEY: VARIANT
<222> LOCATION: (14)...(16)
<223> OTHER INFORMATION: X is any amino acid except Cys
<220> FEATURE:
<221> NAME/KEY: VARIANT
<222> LOCATION: 11, 12, 14, 15, 16
<223> OTHER INFORMATION: Xaa = Any Amino Acid except Cys

<400> SEQUENCE: 32

Asp Trp Val Cys Glu Asn Lys Lys Asp Gln Xaa Xaa Cys Xaa Xaa Xaa
 1               5                  10                  15
```

<210> SEQ ID NO 33
<211> LENGTH: 16
<212> TYPE: PRT
<213> ORGANISM: Artificial Sequence
<220> FEATURE:
<223> OTHER INFORMATION: Template sequence for sublibrary used in
      construction of focused secondary display library
<220> FEATURE:
<221> NAME/KEY: VARIANT
<222> LOCATION: (6)...(7)
<223> OTHER INFORMATION: X is any amino acid except Cys
<220> FEATURE:
<221> NAME/KEY: VARIANT
<222> LOCATION: 9
<223> OTHER INFORMATION: X is any amino acid except Cys
<220> FEATURE:
<221> NAME/KEY: VARIANT
<222> LOCATION: 12
<223> OTHER INFORMATION: X is any amino acid except Cys
<220> FEATURE:
<221> NAME/KEY: VARIANT
<222> LOCATION: 15
<223> OTHER INFORMATION: X is any amino acid except Cys
<220> FEATURE:
<221> NAME/KEY: VARIANT
<222> LOCATION: 6, 7, 9, 12, 15
<223> OTHER INFORMATION: Xaa = Any Amino Acid except Cys

<400> SEQUENCE: 33

Asp Trp Val Cys Glu Xaa Xaa Lys Xaa Gln Trp Xaa Cys Asn Xaa Leu
 1               5                  10                  15

<210> SEQ ID NO 34
<211> LENGTH: 16
<212> TYPE: PRT
<213> ORGANISM: Artificial Sequence
<220> FEATURE:
<223> OTHER INFORMATION: Template sequence for sublibrary used in
      construction of focused secondary display library
<220> FEATURE:
<221> NAME/KEY: VARIANT
<222> LOCATION: (5)...(7)
<223> OTHER INFORMATION: X is any amino acid except Cys
<220> FEATURE:
<221> NAME/KEY: VARIANT
<222> LOCATION: 9
<223> OTHER INFORMATION: X is any amino acid except Cys
<220> FEATURE:
<221> NAME/KEY: VARIANT
<222> LOCATION: 12
<223> OTHER INFORMATION: X is any amino acid except Cys
<220> FEATURE:
<221> NAME/KEY: VARIANT
<222> LOCATION: 5, 6, 7, 9, 12
<223> OTHER INFORMATION: Xaa = Any Amino Acid except Cys

<400> SEQUENCE: 34

Asn Trp Val Cys Xaa Xaa Xaa Lys Xaa Gln Trp Xaa Cys Asn Ser Tyr
 1               5                  10                  15

<210> SEQ ID NO 35
<211> LENGTH: 16
<212> TYPE: PRT
<213> ORGANISM: Artificial Sequence
<220> FEATURE:
<223> OTHER INFORMATION: Template sequence for sublibrary used in
      construction of focused secondary display library
<220> FEATURE:
<221> NAME/KEY: VARIANT
<222> LOCATION: 1
<223> OTHER INFORMATION: X is any amino acid except Cys
<220> FEATURE:
<221> NAME/KEY: VARIANT

```
<222> LOCATION: 3
<223> OTHER INFORMATION: X is any amino acid except Cys
<220> FEATURE:
<221> NAME/KEY: VARIANT
<222> LOCATION: (14)...(16)
<223> OTHER INFORMATION: X is any amino acid except Cys
<220> FEATURE:
<221> NAME/KEY: VARIANT
<222> LOCATION: 1, 3, 14, 15, 16
<223> OTHER INFORMATION: Xaa = Any Amino Acid except Cys

<400> SEQUENCE: 35

Xaa Trp Xaa Cys Asn Leu Phe Lys Asn Gln Trp Phe Cys Xaa Xaa Xaa
 1               5                  10                  15

<210> SEQ ID NO 36
<211> LENGTH: 16
<212> TYPE: PRT
<213> ORGANISM: Artificial Sequence
<220> FEATURE:
<223> OTHER INFORMATION: Family of CEA binding polypeptides
<220> FEATURE:
<221> NAME/KEY: VARIANT
<222> LOCATION: 1
<223> OTHER INFORMATION: Xaa is Asp, Asn, Ala or Ile
<220> FEATURE:
<221> NAME/KEY: VARIANT
<222> LOCATION: 3
<223> OTHER INFORMATION: Xaa is Val, Ile, Met, Tyr, Phe, Pro or Asp
<220> FEATURE:
<221> NAME/KEY: VARIANT
<222> LOCATION: 5
<223> OTHER INFORMATION: Xaa is Asn, Glu or Asp
<220> FEATURE:
<221> NAME/KEY: VARIANT
<222> LOCATION: 6
<223> OTHER INFORMATION: Xaa is Leu, Phe, Tyr, Trp, Val, Met, Ile or Asn
<220> FEATURE:
<221> NAME/KEY: VARIANT
<222> LOCATION: 7
<223> OTHER INFORMATION: Xaa is Phe, Leu, Asp, Glu, Ala, Ile, Lys, Asn,
      Ser, Val, Trp or Tyr
<220> FEATURE:
<221> NAME/KEY: VARIANT
<222> LOCATION: (8)...(8)
<223> OTHER INFORMATION: Xaa is Lys, Phe, Asp, Gly, Leu, Asn or Trp
<220> FEATURE:
<221> NAME/KEY: VARIANT
<222> LOCATION: (9)...(9)
<223> OTHER INFORMATION: Xaa is Asn, Pro, Phe, Gly, Asp, Ala, Ser, Glu,
      Gln or Trp
<220> FEATURE:
<221> NAME/KEY: VARIANT
<222> LOCATION: (10)...(10)
<223> OTHER INFORMATION: Xaa is Gln or Lys
<220> FEATURE:
<221> NAME/KEY: VARIANT
<222> LOCATION: (12)...(12)
<223> OTHER INFORMATION: Xaa is Phe, Thr, Met, Ser, Ala, Asn, Val, His,
      Ile, Pro, Trp or Tyr
<220> FEATURE:
<221> NAME/KEY: VARIANT
<222> LOCATION: (14)...(14)
<223> OTHER INFORMATION: Xaa is Asn, Asp, Glu, Pro, Gln or Ser
<220> FEATURE:
<221> NAME/KEY: VARIANT
<222> LOCATION: (15)...(15)
<223> OTHER INFORMATION: Xaa is Val, Leu, Ile, Pro, Ala, Gln, Ser, Met,
      Glu, Thr, Lys or Trp
<220> FEATURE:
<221> NAME/KEY: VARIANT
<222> LOCATION: (16)...(16)
<223> OTHER INFORMATION: Xaa is Leu, Met, Val, Tyr, Ala, Ile, Trp, His,
      Pro, Gln, Glu, Phe, Lys or Arg

<400> SEQUENCE: 36
```

Xaa Trp Xaa Cys Xaa Xaa Xaa Xaa Xaa Xaa Trp Xaa Cys Xaa Xaa Xaa
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 37

Asp Trp Met Cys Asn Leu Phe Lys Asn Gln Trp Phe Cys Asp Leu Met
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 38

Asp Trp Val Cys Asn Leu Phe Lys Asn Gln Trp Phe Cys Asp Leu Met
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 39

Asp Trp Ile Cys Asn Leu Phe Lys Asn Gln Trp Phe Cys Asp Gln Met
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 40

Asn Trp Ile Cys Asn Leu Phe Lys Asn Gln Trp Phe Cys Asp Gln Glu
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 41

Asp Trp Ile Cys Asn Leu Phe Lys Asn Gln Trp Phe Cys Gln Val Lys
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 42

Asp Trp Val Cys Asn Leu Phe Lys Asn Gln Trp Phe Cys Asp Val Met

```
<210> SEQ ID NO 43
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 43

Asp Trp Met Cys Asn Leu Phe Lys Asn Gln Trp Phe Cys Asp Gln Ile
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 44

Ile Trp Asp Cys Asn Leu Phe Lys Asn Gln Trp Phe Cys Pro Ala Pro
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 45

Asp Trp Ile Cys Asn Leu Phe Lys Asn Gln Trp Phe Cys Asp Ile Arg
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 46

Asp Trp Met Cys Asn Leu Phe Lys Asn Gln Trp Phe Cys Asp Val Val
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 47

Asp Trp Ile Cys Asn Leu Phe Lys Asn Gln Trp Phe Cys Asp Ala Ile
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 48

Asp Trp Ile Cys Asn Leu Phe Lys Asn Gln Trp Phe Cys Asp Met Ala
1               5                   10                  15
```

<210> SEQ ID NO 49
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 49

Asp Trp Val Cys Glu Phe Leu Lys Met Gln Trp Ala Cys Asn Val Leu
 1               5                  10                  15

<210> SEQ ID NO 50
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 50

Asp Trp Val Cys Asn Leu Phe Lys Asn Gln Trp Phe Cys Asn Val Met
 1               5                  10                  15

<210> SEQ ID NO 51
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 51

Ala Trp Pro Cys Asn Leu Phe Lys Asn Gln Trp Phe Cys Pro Pro Gln
 1               5                  10                  15

<210> SEQ ID NO 52
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 52

Asp Trp Val Cys Asn Leu Phe Lys Asn Gln Trp Phe Cys Asp Val Leu
 1               5                  10                  15

<210> SEQ ID NO 53
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 53

Asp Trp Val Cys Asn Leu Phe Lys Asn Gln Trp Phe Cys Asp Lys Trp
 1               5                  10                  15

<210> SEQ ID NO 54
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 54

Asp Trp Val Cys Glu Trp Leu Lys Met Gln Trp Ala Cys Asn Met Leu
 1               5                  10                  15

```
<210> SEQ ID NO 55
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 55

Asp Trp Val Cys Asp Phe Phe Phe Asn Gln Trp Thr Cys Asn Leu Leu
 1               5                  10                  15

<210> SEQ ID NO 56
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 56

Asp Trp Val Cys Glu Met Phe Lys Ala Gln Trp Phe Cys Asn Ala Leu
 1               5                  10                  15

<210> SEQ ID NO 57
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 57

Asp Trp Ile Cys Asn Leu Phe Lys Asn Gln Trp Phe Cys Asp Ala Trp
 1               5                  10                  15

<210> SEQ ID NO 58
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 58

Asp Trp Val Cys Asn Leu Phe Lys Asn Gln Trp Phe Cys Asp Val Trp
 1               5                  10                  15

<210> SEQ ID NO 59
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 59

Asp Trp Val Cys Glu Tyr Phe Lys Asn Gln Trp Phe Cys Asn Val Leu
 1               5                  10                  15

<210> SEQ ID NO 60
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 60

Asp Trp Val Cys Glu Ile Asp Lys Gly Gln Trp Thr Cys Asn Pro Leu
 1               5                  10                  15
```

```
<210> SEQ ID NO 61
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 61

Asp Trp Val Cys Asn Leu Phe Lys Asn Gln Trp Phe Cys Asn Pro Phe
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 62

Asp Trp Val Cys Asn Leu Phe Lys Asn Gln Trp Phe Cys Asp Val Gln
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 63

Asp Trp Val Cys Asn Leu Phe Phe Gly Gln Trp Thr Cys Asn Leu Leu
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 64

Asp Trp Ile Cys Asn Leu Phe Lys Asn Gln Trp Phe Cys Glu Ala His
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 65

Asp Trp Val Cys Glu Leu Val Lys Ala Gln Trp Tyr Cys Asn Ile Leu
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 66

Asn Trp Val Cys Asn Leu Phe Lys Asn Gln Trp Phe Cys Asp Thr Val
1               5                   10                  15

<210> SEQ ID NO 67
```

```
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 67

Asp Trp Val Cys Glu Phe Tyr Lys Ser Gln Trp Asn Cys Asn Ile Leu
 1               5                  10                  15

<210> SEQ ID NO 68
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 68

Asp Trp Val Cys Glu Trp Phe Lys Pro Gln Trp Phe Cys Asn Pro Leu
 1               5                  10                  15

<210> SEQ ID NO 69
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 69

Asp Trp Tyr Cys Asn Leu Phe Lys Asn Gln Trp Phe Cys Asp Val Leu
 1               5                  10                  15

<210> SEQ ID NO 70
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 70

Asp Trp Val Cys Glu Tyr Asn Asp Glu Gln Trp Thr Cys Asn Leu Leu
 1               5                  10                  15

<210> SEQ ID NO 71
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 71

Asp Trp Ile Cys Asn Leu Phe Lys Asn Gln Trp Phe Cys Asn Glu Ala
 1               5                  10                  15

<210> SEQ ID NO 72
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 72

Asp Trp Val Cys Asn Trp Glu Leu Phe Gln Trp Thr Cys Asn Leu Leu
 1               5                  10                  15

<210> SEQ ID NO 73
<211> LENGTH: 16
```

```
<212> TYPE: PRT
<213> ORGANISM: Artificial Sequence
<220> FEATURE:
<223> OTHER INFORMATION: CEA binding polypeptide

<400> SEQUENCE: 73

Asp Trp Val Cys Asn Leu Phe Lys Asn Gln Trp Phe Cys Asp Gln Val
 1               5                  10                  15

<210> SEQ ID NO 74
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 74

Asp Trp Val Cys Asn Leu Phe Lys Asn Gln Trp Phe Cys Asp Val Pro
 1               5                  10                  15

<210> SEQ ID NO 75
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 75

Asp Trp Val Cys Glu Phe Phe Lys Gln Gln Trp Phe Cys Asn Val Leu
 1               5                  10                  15

<210> SEQ ID NO 76
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 76

Asp Trp Val Cys Glu Phe Phe Lys Asp Gln Trp Ser Cys Asn Val Leu
 1               5                  10                  15

<210> SEQ ID NO 77
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 77

Asp Trp Val Cys Asn Leu Phe Lys Asn Gln Trp Phe Cys Asp Ser Leu
 1               5                  10                  15

<210> SEQ ID NO 78
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 78

Asp Trp Val Cys Glu Phe Met Lys His Gln Trp Phe Cys Asn Pro Leu
 1               5                  10                  15

<210> SEQ ID NO 79
<211> LENGTH: 16
<212> TYPE: PRT
```

```
<213> ORGANISM: Artificial Sequence
<220> FEATURE:
<223> OTHER INFORMATION: CEA binding polypeptide

<400> SEQUENCE: 79

Asp Trp Ile Cys Asn Leu Phe Lys Asn Gln Trp Phe Cys Gln Ala Val
1               5                   10                  15

<210> SEQ ID NO 80
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 80

Asp Trp Val Cys Glu Phe Ile Lys Asn Gln Trp Met Cys Asn Val Leu
1               5                   10                  15

<210> SEQ ID NO 81
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 81

Asp Trp Val Cys Asn Leu Phe Lys Asn Gln Trp Phe Cys Asp Ala Leu
1               5                   10                  15

<210> SEQ ID NO 82
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 82

Asp Trp Val Cys Glu Tyr Glu Lys Asp Gln Trp Ser Cys Asn Ile Leu
1               5                   10                  15

<210> SEQ ID NO 83
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 83

Asp Trp Val Cys Asn Leu Phe Lys Asn Gln Trp Phe Cys Asp Thr Leu
1               5                   10                  15

<210> SEQ ID NO 84
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 84

Asp Trp Tyr Cys Asn Leu Phe Lys Asn Gln Trp Phe Cys Asp Val Tyr
1               5                   10                  15

<210> SEQ ID NO 85
<211> LENGTH: 16
<212> TYPE: PRT
<213> ORGANISM: Artificial Sequence
```

```
<220> FEATURE:
<223> OTHER INFORMATION: CEA binding polypeptide

<400> SEQUENCE: 85

Asp Trp Phe Cys Asn Leu Phe Lys Asn Gln Trp Phe Cys Ser Pro Ile
 1               5                  10                  15

<210> SEQ ID NO 86
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 86

Asp Trp Val Cys Glu Phe Phe Lys Lys Gln Trp Phe Cys Asn Leu Leu
 1               5                  10                  15

<210> SEQ ID NO 87
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 87

Asn Trp Val Cys Asp Val Leu Lys Trp Gln Trp Pro Cys Asn Ser Tyr
 1               5                  10                  15

<210> SEQ ID NO 88
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 88

Asp Trp Val Cys Glu Tyr Asp Lys Gly Gln Trp His Cys Asn Ile Leu
 1               5                  10                  15

<210> SEQ ID NO 89
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 89

Asp Trp Ile Cys Asn Leu Phe Lys Asn Gln Trp Phe Cys Gln Gln His
 1               5                  10                  15

<210> SEQ ID NO 90
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 90

Asp Trp Val Cys Asn Trp Leu Trp Gly Gln Trp Thr Cys Asn Leu Leu
 1               5                  10                  15

<210> SEQ ID NO 91
<211> LENGTH: 16
<212> TYPE: PRT
<213> ORGANISM: Artificial Sequence
<220> FEATURE:
```

<223> OTHER INFORMATION: CEA binding polypeptide

<400> SEQUENCE: 91

Asp Trp Val Cys Glu Met Phe Lys Lys Gln Trp Val Cys Asn Pro Leu
1               5                   10                  15

<210> SEQ ID NO 92
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 92

Asp Trp Ile Cys Asn Leu Phe Lys Asn Gln Trp Phe Cys Gly Pro Leu
1               5                   10                  15

<210> SEQ ID NO 93
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 93

Asp Trp Val Cys Glu Val Ile Lys Asp Gln Trp Val Cys Asn Pro Leu
1               5                   10                  15

<210> SEQ ID NO 94
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 94

Asp Trp Val Cys Glu Asn Lys Asn Phe Lys Trp Phe Cys Asn Leu Leu
1               5                   10                  15

<210> SEQ ID NO 95
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 95

Asp Trp Val Cys Glu Tyr Ala Lys Asn Gln Trp Asn Cys Asn Pro Leu
1               5                   10                  15

<210> SEQ ID NO 96
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 96

Asn Trp Val Cys Asn Leu Phe Lys Asn Gln Trp Phe Cys Glu Trp Ala
1               5                   10                  15

<210> SEQ ID NO 97
<211> LENGTH: 16
<212> TYPE: PRT
<213> ORGANISM: Artificial Sequence
<220> FEATURE:
<223> OTHER INFORMATION: CEA binding polypeptide

```
<400> SEQUENCE: 97

Asn Trp Val Cys Asp Tyr Trp Lys Pro Gln Trp Phe Cys Asn Ser Tyr
 1               5                  10                  15

<210> SEQ ID NO 98
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 98

Asp Trp Tyr Cys Asn Leu Phe Lys Asn Gln Trp Phe Cys Asp Leu Val
 1               5                  10                  15

<210> SEQ ID NO 99
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 99

Asn Trp Val Cys Asn Leu Phe Lys Asn Gln Trp Phe Cys Asp Glu Met
 1               5                  10                  15

<210> SEQ ID NO 100
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 100

Asp Trp Val Cys Glu Leu Phe Lys Pro Gln Trp Phe Cys Asn Ile Leu
 1               5                  10                  15

<210> SEQ ID NO 101
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 101

Asp Trp Val Cys Glu Trp Ser Lys Met Gln Trp Ser Cys Asn Ala Leu
 1               5                  10                  15

<210> SEQ ID NO 102
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 102

Asp Trp Val Cys Asp Tyr Lys Phe Phe Gln Trp Thr Cys Asn Leu Leu
 1               5                  10                  15

<210> SEQ ID NO 103
<211> LENGTH: 16
<212> TYPE: PRT
<213> ORGANISM: Artificial Sequence
<220> FEATURE:
<223> OTHER INFORMATION: CEA binding polypeptide
```

```
<400> SEQUENCE: 103

Asn Trp Val Cys Glu Trp Leu Lys Pro Gln Trp Trp Cys Asn Ser Tyr
 1               5                  10                  15

<210> SEQ ID NO 104
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 104

Asp Trp Val Cys Glu Phe Phe Lys Pro Gln Trp Met Cys Asn Ile Leu
 1               5                  10                  15

<210> SEQ ID NO 105
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 105

Asp Trp Val Cys Glu Tyr Phe Lys Ser Gln Trp Met Cys Asn Met Leu
 1               5                  10                  15

<210> SEQ ID NO 106
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 106

Asp Trp Val Cys Glu Phe Phe Gly Met Gln Trp Thr Cys Asn Leu Leu
 1               5                  10                  15

<210> SEQ ID NO 107
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 107

Asp Trp Val Cys Glu Tyr Ala Lys Phe Gln Trp Ile Cys Asn Ile Leu
 1               5                  10                  15

<210> SEQ ID NO 108
<211> LENGTH: 16
<212> TYPE: PRT
<213> ORGANISM: Artificial Sequence
<220> FEATURE:
<223> OTHER INFORMATION: CEA binding polypeptide

<400> SEQUENCE: 108

Asp Trp Ile Cys Asn Leu Phe Lys Asn Gln Trp Phe Cys Asn Glu Ala
 1               5                  10                  15

<210> SEQ ID NO 109
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 109
```

Asp Trp Val Cys Glu Tyr Phe Lys Asn Gln Trp Phe Cys Asp Thr Leu
1               5                   10                  15

<210> SEQ ID NO 110
<211> LENGTH: 10
<212> TYPE: PRT
<213> ORGANISM: Artificial Sequence
<220> FEATURE:
<223> OTHER INFORMATION: Synthetic 16-mer microprotein analogue
<220> FEATURE:
<221> NAME/KEY: VARIANT
<222> LOCATION: 2
<223> OTHER INFORMATION: X is Asn, Glu, Asp or Met
<220> FEATURE:
<221> NAME/KEY: VARIANT
<222> LOCATION: 3
<223> OTHER INFORMATION: X is Leu, Phe, Tyr, Trp, Val, Met, Ile or Asn
<220> FEATURE:
<221> NAME/KEY: VARIANT
<222> LOCATION: 4
<223> OTHER INFORMATION: X is Phe, Leu, Asp, Glu, Ala, Ile, Lys, Asn,
      Ser, Val, Trp, Tyr, Gly or Thr
<220> FEATURE:
<221> NAME/KEY: VARIANT
<222> LOCATION: 5
<223> OTHER INFORMATION: X is Lys, Phe, Asp, Gly, Leu, Asn, Trp, Ala,
      Gln or Thr
<220> FEATURE:
<221> NAME/KEY: VARIANT
<222> LOCATION: 6
<223> OTHER INFORMATION: X is Asn, Pro, Phe, Gly, Asp, Ala, Ser, Glu,
      Gln, Trp, His, Arg, Met, Val or Leu
<220> FEATURE:
<221> NAME/KEY: VARIANT
<222> LOCATION: (7)...(7)
<223> OTHER INFORMATION: X is Gln, Lys, Leu or Gly
<220> FEATURE:
<221> NAME/KEY: VARIANT
<222> LOCATION: (8)...(8)
<223> OTHER INFORMATION: X is Tyr, Trp or Ala
<220> FEATURE:
<221> NAME/KEY: VARIANT
<222> LOCATION: (9)...(9)
<223> OTHER INFORMATION: X is Phe, Thr, Met, Ser, Ala, Asn, Val, His,
      Ile, Pro, Trp, Tyr, Gly, Leu or Glu

<400> SEQUENCE: 110

Cys Xaa Xaa Xaa Xaa Xaa Xaa Xaa Xaa Cys
1               5                   10

<210> SEQ ID NO 111
<211> LENGTH: 16
<212> TYPE: PRT
<213> ORGANISM: Artificial Sequence
<220> FEATURE:
<223> OTHER INFORMATION: Synthetic 16-mer microprotein analogue
<220> FEATURE:
<221> NAME/KEY: VARIANT
<222> LOCATION: 1
<223> OTHER INFORMATION: X is Asp, Asn, Ala or Ile
<220> FEATURE:
<221> NAME/KEY: VARIANT
<222> LOCATION: 2
<223> OTHER INFORMATION: X is Trp
<220> FEATURE:
<221> NAME/KEY: VARIANT
<222> LOCATION: 3
<223> OTHER INFORMATION: X is Val, Ile, Met, Tyr, Phe, Pro or Asp
<220> FEATURE:
<221> NAME/KEY: VARIANT
<222> LOCATION: 5
<223> OTHER INFORMATION: X is Asn, Glu, Asp or Met
<220> FEATURE:
<221> NAME/KEY: VARIANT
<222> LOCATION: 6

```
<223> OTHER INFORMATION: X is Leu, Phe, Tyr, Trp, Val, Met, Ile, or Asn
<220> FEATURE:
<221> NAME/KEY: VARIANT
<222> LOCATION: (7)...(7)
<223> OTHER INFORMATION: X is Phe, Leu, Asp, Glu, Ala, Ile, Lys, Asn,
      Ser, Val, Trp, Tyr, Gly or Thr
<220> FEATURE:
<221> NAME/KEY: VARIANT
<222> LOCATION: (8)...(8)
<223> OTHER INFORMATION: X is Lys, Phe, Asp, Gly, Leu, Asn, Trp, Ala,
      Gln, or Thr
<220> FEATURE:
<221> NAME/KEY: VARIANT
<222> LOCATION: (9)...(9)
<223> OTHER INFORMATION: X is Asn, Pro, Phe, Gly, Asp, Ala, Ser, Glu,
      Gln, Trp, His, Arg, Met, Val, or Leu
<220> FEATURE:
<221> NAME/KEY: VARIANT
<222> LOCATION: (10)...(10)
<223> OTHER INFORMATION: X is Gln, Lys, Leu or Gly
<220> FEATURE:
<221> NAME/KEY: VARIANT
<222> LOCATION: (11)...(11)
<223> OTHER INFORMATION: X is Trp, Tyr or Ala
<220> FEATURE:
<221> NAME/KEY: VARIANT
<222> LOCATION: (12)...(12)
<223> OTHER INFORMATION: X is Phe, Thr, Met, Ser, Ala, Asn, Val, His,
      Ile, Pro, Trp, Tyr, Gly, Leu or Glu
<220> FEATURE:
<221> NAME/KEY: VARIANT
<222> LOCATION: (14)...(14)
<223> OTHER INFORMATION: X is Asn, Asp, Glu, Pro, Gln, Ser, Phe, or Val
<220> FEATURE:
<221> NAME/KEY: VARIANT
<222> LOCATION: (15)...(15)
<223> OTHER INFORMATION: X is Val, Leu, Ile, Pro, Ala, Gln, Ser, Met,
      Glu,Thr, Lys, Trp or Arg
<220> FEATURE:
<221> NAME/KEY: VARIANT
<222> LOCATION: (16)...(16)
<223> OTHER INFORMATION: X is Leu, Met, Val, Tyr, Ala, Ile, Trp, His,
      Pro, Gln, Glu, Phe, Lys, Arg or Ser

<400> SEQUENCE: 111

Xaa Xaa Xaa Cys Xaa Xaa Xaa Xaa Xaa Xaa Xaa Xaa Cys Xaa Xaa Xaa
 1               5                  10                  15

<210> SEQ ID NO 112
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 112

Asp Trp Val Cys Glu Trp Leu Lys Met Gln Trp Ala Cys Asn Ile Leu
 1               5                  10                  15

<210> SEQ ID NO 113
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 113

Asp Trp Val Cys Glu Tyr Val Lys Ser Gln Trp Ser Cys Asn Pro Leu
 1               5                  10                  15

<210> SEQ ID NO 114
<211> LENGTH: 16
<212> TYPE: PRT
```

```
<213> ORGANISM: Artificial Sequence
<220> FEATURE:
<223> OTHER INFORMATION: Synthetic 16-mer microprotein analogue

<400> SEQUENCE: 114

Asp Trp Val Cys Glu Phe Ser Lys Val Gln Trp Tyr Cys Asn Pro Leu
 1               5                  10                  15

<210> SEQ ID NO 115
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 115

Asp Trp Val Cys Glu Trp Phe Lys Pro Gln Trp Ile Cys Asn Leu Leu
 1               5                  10                  15

<210> SEQ ID NO 116
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 116

Asp Trp Val Cys Glu Ile Val Lys Asn Gln Trp His Cys Asn Val Leu
 1               5                  10                  15

<210> SEQ ID NO 117
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 117

Asp Trp Val Cys Glu Trp Gly Lys Asn Gln Trp Thr Cys Asn Pro Leu
 1               5                  10                  15

<210> SEQ ID NO 118
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 118

Asp Trp Val Cys Glu Phe Glu Lys Gly Gln Trp Thr Cys Asn Val Leu
 1               5                  10                  15

<210> SEQ ID NO 119
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 119

Asp Trp Val Cys Asn Leu Phe Lys Asn Gln Trp Phe Cys Asn Val Trp
 1               5                  10                  15

<210> SEQ ID NO 120
<211> LENGTH: 16
<212> TYPE: PRT
<213> ORGANISM: Artificial Sequence
```

```
<220> FEATURE:
<223> OTHER INFORMATION: Synthetic 16-mer microprotein analogue

<400> SEQUENCE: 120

Asp Trp Val Cys Asn Leu Phe Lys Asn Gln Trp Phe Cys Asp Val His
 1               5                  10                  15

<210> SEQ ID NO 121
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 121

Asp Trp Ile Cys Asn Leu Phe Lys Asn Gln Trp Phe Cys Asp Ile Arg
 1               5                  10                  15

<210> SEQ ID NO 122
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 122

Asp Trp Val Cys Glu Trp Leu Lys Met Gln Trp Ala Cys Asn Ile Leu
 1               5                  10                  15

<210> SEQ ID NO 123
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 123

Asp Trp Val Cys Glu Phe Ile Lys Asp Gln Trp Tyr Cys Asp Leu Ala
 1               5                  10                  15

<210> SEQ ID NO 124
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 124

Asp Trp Val Cys Asn Leu Phe Lys Asn Gln Trp Phe Cys Asp Val Val
 1               5                  10                  15

<210> SEQ ID NO 125
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 125

Asp Trp Val Cys Glu Trp Leu Lys Met Gln Trp Ala Cys Asn Val Leu
 1               5                  10                  15

<210> SEQ ID NO 126
<211> LENGTH: 16
<212> TYPE: PRT
<213> ORGANISM: Artificial Sequence
<220> FEATURE:
```

<223> OTHER INFORMATION: Synthetic 16-mer microprotein analogue

<400> SEQUENCE: 126

Asp Trp Val Cys Glu Trp Leu Lys Asn Gln Trp Trp Cys Asn Val Leu
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 127

Asp Trp Val Cys Glu Leu Leu Lys Asn Gln Trp Phe Cys Asn Val Leu
1               5                   10                  15

<210> SEQ ID NO 128
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 128

Asp Trp Val Cys Asn Leu Phe Lys Asn Gln Trp Phe Cys Asn Val Leu
1               5                   10                  15

<210> SEQ ID NO 129
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 129

Asp Trp Val Cys Asn Leu Phe Lys Asn Gln Trp Phe Cys Asp Val Met
1               5                   10                  15

<210> SEQ ID NO 130
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 130

Asp Trp Val Cys Glu Trp Phe Lys Ala Gln Trp Phe Cys Asn Met Leu
1               5                   10                  15

<210> SEQ ID NO 131
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 131

Asp Trp Ile Cys Asn Leu Phe Lys Asn Gln Trp Phe Cys Asp Gln Leu
1               5                   10                  15

<210> SEQ ID NO 132
<211> LENGTH: 16
<212> TYPE: PRT
<213> ORGANISM: Artificial Sequence
<220> FEATURE:
<223> OTHER INFORMATION: Synthetic 16-mer microprotein analogue

```
<400> SEQUENCE: 132

Asp Trp Met Cys Asn Leu Phe Lys Asn Gln Trp Phe Cys Asp Val Gln
 1               5                  10                  15

<210> SEQ ID NO 133
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 133

Asp Trp Val Cys Glu Phe Asp Lys Gly Gln Trp Asn Cys Asn Ile Leu
 1               5                  10                  15

<210> SEQ ID NO 134
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 134

Asp Trp Ile Cys Asn Leu Phe Lys Asn Gln Trp Phe Cys Asp Ala Trp
 1               5                  10                  15

<210> SEQ ID NO 135
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 135

Asp Trp Val Cys Glu Phe Asp Lys Leu Gln Trp Val Cys Asn Val Leu
 1               5                  10                  15

<210> SEQ ID NO 136
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 136

Asp Trp Val Cys Asn Leu Phe Lys Asn Gln Trp Phe Cys Asp Gln Met
 1               5                  10                  15

<210> SEQ ID NO 137
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 137

Asp Trp Val Cys Glu Phe Phe Lys Ser Gln Trp Tyr Cys Asn Ile Leu
 1               5                  10                  15

<210> SEQ ID NO 138
<211> LENGTH: 16
<212> TYPE: PRT
<213> ORGANISM: Artificial Sequence
<220> FEATURE:
<223> OTHER INFORMATION: Synthetic 16-mer microprotein analogue
```

```
<400> SEQUENCE: 138

Asp Trp Val Cys Glu Trp Leu Lys Met Gln Trp Ala Cys Asn Met Leu
1               5                   10                  15

<210> SEQ ID NO 139
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 139

Asp Trp Val Cys Glu Tyr Phe Lys Asn Gln Trp Leu Cys Asn Ile Leu
1               5                   10                  15

<210> SEQ ID NO 140
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 140

Asp Trp Val Cys Glu Trp Leu Lys Met Gln Trp Ala Cys Asn Ile Leu
1               5                   10                  15

<210> SEQ ID NO 141
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 141

Asp Trp Val Cys Glu Trp Leu Lys Met Gln Trp Phe Cys Asn Ala Leu
1               5                   10                  15

<210> SEQ ID NO 142
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 142

Asp Trp Val Cys Glu Trp Leu Lys Met Gln Trp Ala Cys Asn Val Leu
1               5                   10                  15

<210> SEQ ID NO 143
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 143

Asp Trp Val Cys Glu Trp Leu Lys Met Gln Trp Ala Cys Asn Met Leu
1               5                   10                  15

<210> SEQ ID NO 144
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 144
```

```
Asp Trp Val Cys Glu Trp Leu Lys Pro Gln Trp Tyr Cys Asn Ser Leu
 1               5                  10                  15
```

<210> SEQ ID NO 145
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 145

```
Asp Trp Val Cys Asn Leu Phe Lys Asn Gln Trp Phe Cys Asp Leu Ser
 1               5                  10                  15
```

<210> SEQ ID NO 146
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 146

```
Asp Trp Val Cys Glu Trp Leu Lys Ser Gln Trp Phe Cys Asn Ser Leu
 1               5                  10                  15
```

<210> SEQ ID NO 147
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 147

```
Asp Trp Val Cys Glu Phe Ile Lys Ser Gln Trp Phe Cys Asn Val Leu
 1               5                  10                  15
```

<210> SEQ ID NO 148
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 148

```
Asp Trp Val Cys Glu Trp Leu Lys His Gln Trp Phe Cys Asn Ala Leu
 1               5                  10                  15
```

<210> SEQ ID NO 149
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 149

```
Asp Trp Val Cys Glu Ile Val Lys Asn Gln Trp Ile Cys Asn Pro Leu
 1               5                  10                  15
```

<210> SEQ ID NO 150
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 150

-continued

Asp Trp Val Cys Glu Phe Phe Lys Asp Gln Trp Phe Cys Asn Ile Leu
 1               5                   10                  15

<210> SEQ ID NO 151
<211> LENGTH: 16
<212> TYPE: PRT
<213> ORGANISM: Artificial Sequence
<220> FEATURE:
<223> OTHER INFORMATION: Synthetic 16-mer microprotein analogue

<400> SEQUENCE: 151

Asp Trp Val Cys Glu Phe Leu Lys Met Gln Trp Ala Cys Asn Val Leu
 1               5                   10                  15